United States Patent [19]

Hachiya et al.

[11] Patent Number: 5,190,687
[45] Date of Patent: Mar. 2, 1993

[54] LIQUID-CRYSTALLINE POLYMERS AND COPOLYMERS

[75] Inventors: Satoshi Hachiya; Hiroyuki Endo, both of Chiba; Shunji Uchida, Tokyo, all of Japan

[73] Assignee: Idemitsu Kosan Co., Ltd., Tokyo, Japan

[21] Appl. No.: 413,625

[22] Filed: Sep. 28, 1989

[30] Foreign Application Priority Data

Oct. 5, 1988 [JP] Japan .................. 63-249966

[51] Int. Cl.$^5$ .................. C09K 19/52; C09K 19/10
[52] U.S. Cl. .................. 252/299.01; 252/299.62; 252/299.64; 252/299.65; 252/299.66; 526/320; 526/326
[58] Field of Search .................. 526/320, 326; 252/299.01, 299.62, 299.64, 299.65, 299.66

[56] References Cited

U.S. PATENT DOCUMENTS 4,923,633 5/1990 Gray et al. .................. 252/299.01
5,034,153 7/1991 Uchida et al. .................. 252/299.01

Primary Examiner—Paul R. Michl
Assistant Examiner—Tae H. Yoon
Attorney, Agent, or Firm—Antonelli, Terry, Stout & Kraus

[57] ABSTRACT

A liquid-crystalline polymer having the repeating units represented by the following general formula (II):

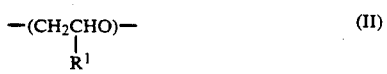

wherein
R$^1$ is wherein
a is an integer having a value of 1 to 10,
b is an integer having a value of 0 or 1,
c is an integer having a value of 1 to 30,
X$^1$ is —COO—, —O— or a single bond,
M$^1$ is

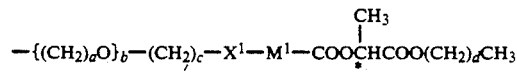

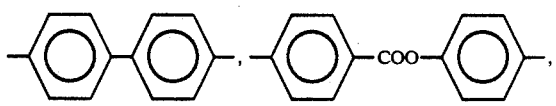

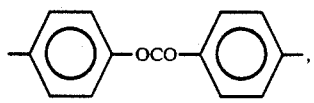

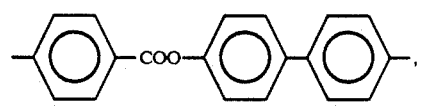

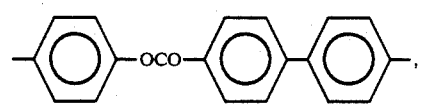

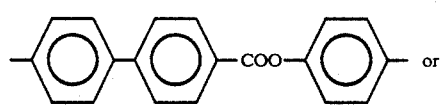

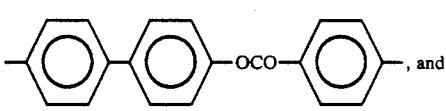

d is an integer having a value of 1 to 5.

The liquid-crystalline polymer exhibits ferroelectricity in a wide temperature range including room temperature and has a high speed of response to electric field.

10 Claims, 25 Drawing Sheets

LIQUID-CRYSTALLINE POLYMERS AND COPOLYMERS

BACKGROUND OF THE INVENTION (a) Field of the Invention

The present invention relates to liquid-crystalline polymers and to liquid-crystalline compounds to be used for preparation of the liquid-crystalline polymers.

More particularly, the present invention relates to liquid-crystalline polymers and liquid-crystalline compounds to be used for preparation of the liquid-crystalline polymers, which liquid-crystalline polymers exhibit ferroelectricity even at temperatures around room temperature, have such high speeds of response to external factors as to enable display of motion pictures. Such liquid-crystalline polymers are useful in optoelectronics fields as various kinds of optical elements, particularly, as those for display devices for desk calculators, clocks and watches, etc., and as those for various electronic optical devices for electronic optical shutters, electronic optical diaphragms, optical modulators, optical-path transfer switches in optical communication systems, memories, liquid crystal printer heads, varifocal lenses, etc. In addition to the above-described advantages, the liquid-crystalline polymers of the present invention have also high practicality in their use as the display elements for large display screens or curved display screens.

(b) Description of the Related Art

Display devices in which low molecular weight liquid crystals are used as their display elements have been widely used for digital display of desk calculators, clocks and watches, etc. In these fields of utilization, the conventional low molecular weight liquid crystals are generally supported between a couple of glass substrates spaced from each other in microns. However, such an adjustment of the space has been practically impossible in production of large display screens or curved display screens. In order to solve the problem, some attempts have been made to develop polymeric liquid crystals so as to render moldability to the liquid crystals themselves. For example, in Japanese Patent Application Kokai Koho (Laid-open) No. 55-21479, Japanese Patent Application Kokai Koho (Laid-open) No. 63-99204, and EP-0184482 disclosed are various kinds of polyacrylate-type ferroelectric, polymeric liquid crystals. Nevertheless, these conventional polymeric liquid crystals have hardly been satisfactory for practical use because of their high temperature ranges where ferroelectricity is exhibited. Further, these polymeric liquid crystals have deficiencies in that their speeds of response in the changes of their transmission intensity to the changes of external factors such as electric field are generally slow.

In Japanese Patent Application Kokai Koho (Laid-open) No. 1-131234 disclosed are polyether-type ferroelectric, polymeric liquid crystals having particular chemical structures which are colorless, exhibit ferroelectricity even at temperatures around room temperature, and have high speed of response to electric field. In spite of their high speed of response to electric field, they still have a problem in that they hardly take bistable state because of their short helical pitches. Further, polymers having two-cyclic skeleton in their mesogenic groups generally have low temperature ranges of SmC* phase (ferroelectric, chiral smetic C phase), and those of polymers having three-cyclic skeleton in their mesogenic radicals are generally high, and therefore, there is a difficulty in their use at temperatures around room temperature.

SUMMARY OF THE INVENTION

An object of the present invention is to provide a liquid-crystalline polymer which exhibits ferroelectricity in a wide temperature range including temperatures around room temperature, has such a high speed of response to external factors as to enable display of motion pictures, and can be advantageously used as display elements for large display screens or curved display screens.

Another object of the present invention is to provide a liquid-crystalline compound which can be suitably used for synthesis of the above-described liquid-crystalline polymer.

More another object of the present invention is to improve the SmC* temperature range and helical pitches of ferroelectric liquid-crystalline homopolymers having high response speed, by copolymerizing liquid-crystalline monomers to be used for the liquid-crystalline homopolymers or by copolymerizing the liquid-crystalline monomers with non-liquid-crystalline monomers, thereby providing liquid-crystalline copolymers which exhibit high speed of response to electric field around room temperature and have longer helical pitches (i.e., by which bistable state can be easily attained,).

As the result of repeated researches for solving the above problems, we found that polyether-type polymers having specified repeating units exhibit SmC* phase in a wide temperature range including temperatures around room temperature and have high response speeds to electric field. Also, we found that copolymers obtainable by copolymerizing the above-described polyether-type polymers with specified monomers have ferroelectricity temperature ranges closer to room temperature than those of homopolymers and have longer helical pitches than those of homopolymers. On the basis of these knowledges, we have completed the present invention.

That is, the present invention provides a liquid-crystalline compound having the structure represented by the following general formula (I):

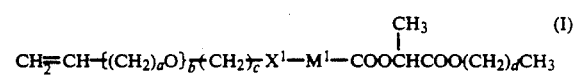

wherein
a is an integer having a value of 1 to 10,
b is an integer having a value of 0 or 1,
c is an integer having a value of 1 to 30,
$X^1$ is —COO—, —O— or a single bond,
$M^1$ is

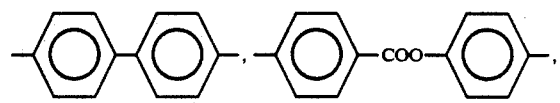

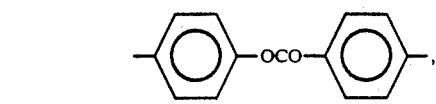

d is an integer having a value of 1 to 5.

Further, the present invention provides a liquid-crystalline polymer obtainable by polymerizing a monomer whose precursor is the above-described liquid-crystalline compounds, i.e. a liquid-crystalline polymer having the repeating units represented by the following general formula (II):

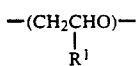 (II)

wherein
$R^1$ is

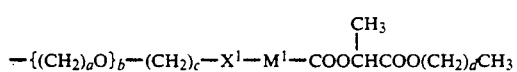

wherein
a is an integer having a value of 1 to 10,
b is an integer having a value of 0 or 1,
c is an integer having a value of 1 to 30,
$X^1$ is —COO, —O— or a single bond,
$M^1$ is

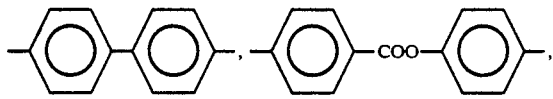

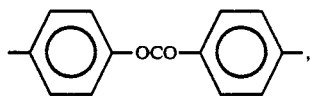

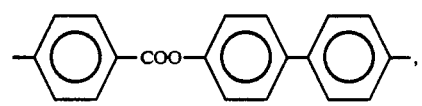

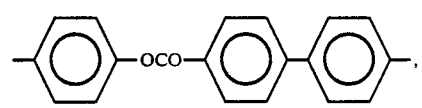

d is an integer having a value of 1 to 5.

Further, the present invention provides a liquid-crystalline copolymer comprising the repeating units (II) of the above-described liquid-crystalline homopolymer as an essential constituent unit, i.e., a liquid-crystalline copolymer having the repeating units represented by the following general formula (II) and the repeating units represented by the following general formula (III), the molar ratio between the repeating units (II) and the repeating units (III), m:n, is from 99:1 to 1:99,

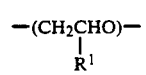 (II)

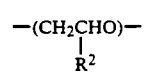 (III)

wherein
$R^1$ is

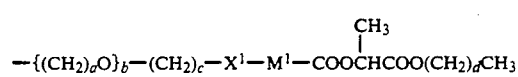

$R^2$ is

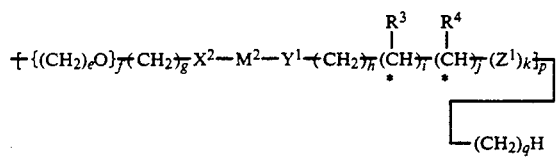

wherein
$X^1$ is —COO, —O— or a single bond,
$X^2$ and $Y^1$ are each independently —COO—, —OCO—, —O— or a single bond,
$M^1$ and $M^2$ are each independently

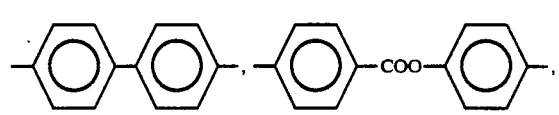

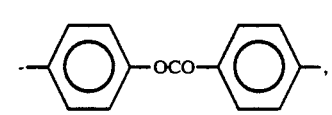

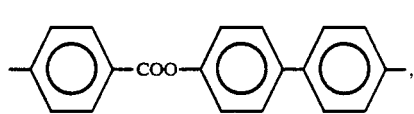

-continued

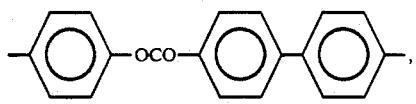

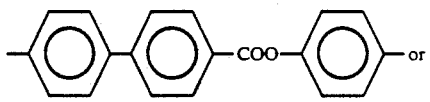  or

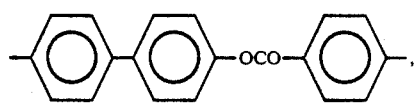, $Z^1$ is —COO—, —OCO— or —O—,
$R^3$ and $R^4$ are each independently —CH$_3$, —CF$_3$, —CN or a halogen group,
a and e are each independently an integer having a value of 1 to 10,
q is an integer having a value of 0 to 10,
c and g are each independently an integer having a value of 1 to 30,
d is an integer having a value of 1 to 5,
h is an integer having a value of 0 to 5, and
b, f, i, j, k, and p are each independently an integer having a value of 0 or 1, with the proviso that $M^1 \neq M^2$ when a=e and b=f and k=p=1 and $Z^1$=—COO—.

More further, the present invention provides a terpolymer having the repeating units (II) of the above-described liquid-crystalline homopolymer as an essential constituent unit, i.e., a liquid-crystalline copolymer having the repeating units represented by the following general formula (II), the repeating units represented by the following general formula (IV), and the repeating units represented by the following general formula (V), the molar ratio between the repeating units (II), the repeating units (IV), and the repeating units (V), s:t:u, is 98:1:1–1:98:1–1:1:98, $$-(CH_2CHO)- \quad (II)$$
$$\quad | \quad$$
$$\quad R^1$$

$$-(CH_2CHO)- \quad (IV)$$
$$\quad | \quad$$
$$\quad R^5$$

$$-(CH_2CHO)- \quad (V)$$
$$\quad | \quad$$
$$\quad R^6$$

wherein
$R^1$ is

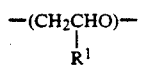

$R^5$ is

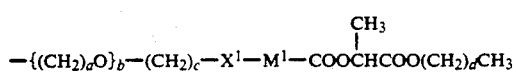

$R^6$ is

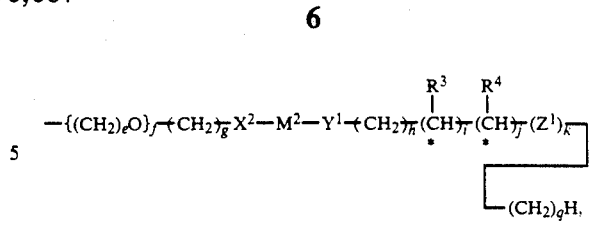

wherein
$X^1$ is —COO, —O— or a single bond,
$X^2$, $X^3$, $Y^1$, and $Y^2$ are each independently —COO—, —OCO—, —O— or a single bond,
$M^1$, $M^2$, and $M^3$ are each independently

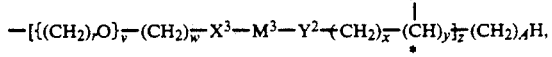

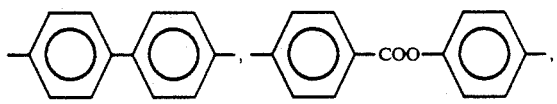

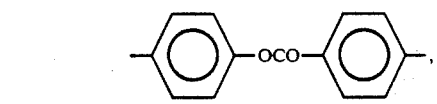

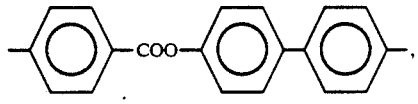

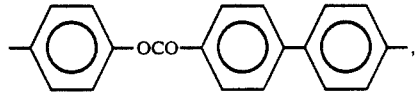

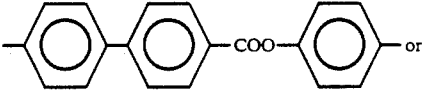

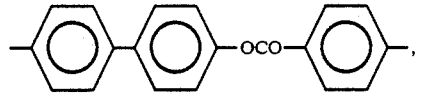

$Z^1$ is —COO—, —OCO— or —O—,
$R^3$, $R^4$, and $R^7$ are each independently —CH$_3$, —CF$_3$, —CN or a halogen group,
a, e, and r are each independently an integer having a value of 1 to 10,
q and A are each independently an integer having a value of 0 to 10,
c, g, and w are each independently an integer having a value of 1 to 30,
d is an integer having a value of 1 to 5,
h and x are each independently are an integer having a value of 0 to 5, and
b, f, v, i, j, k, y, and z are each independently an integer having a value of 0 to 1, with the proviso that $M^1 \neq M^2$ when a=e and b=f and k=1 and $Z^1$=—COO—, and that $(h+q) \neq (x+A)$ when e=r and f=v and k=0 and z=1.

DESCRIPTION OF THE PREFERRED EMBODIMENTS

Figure 1:
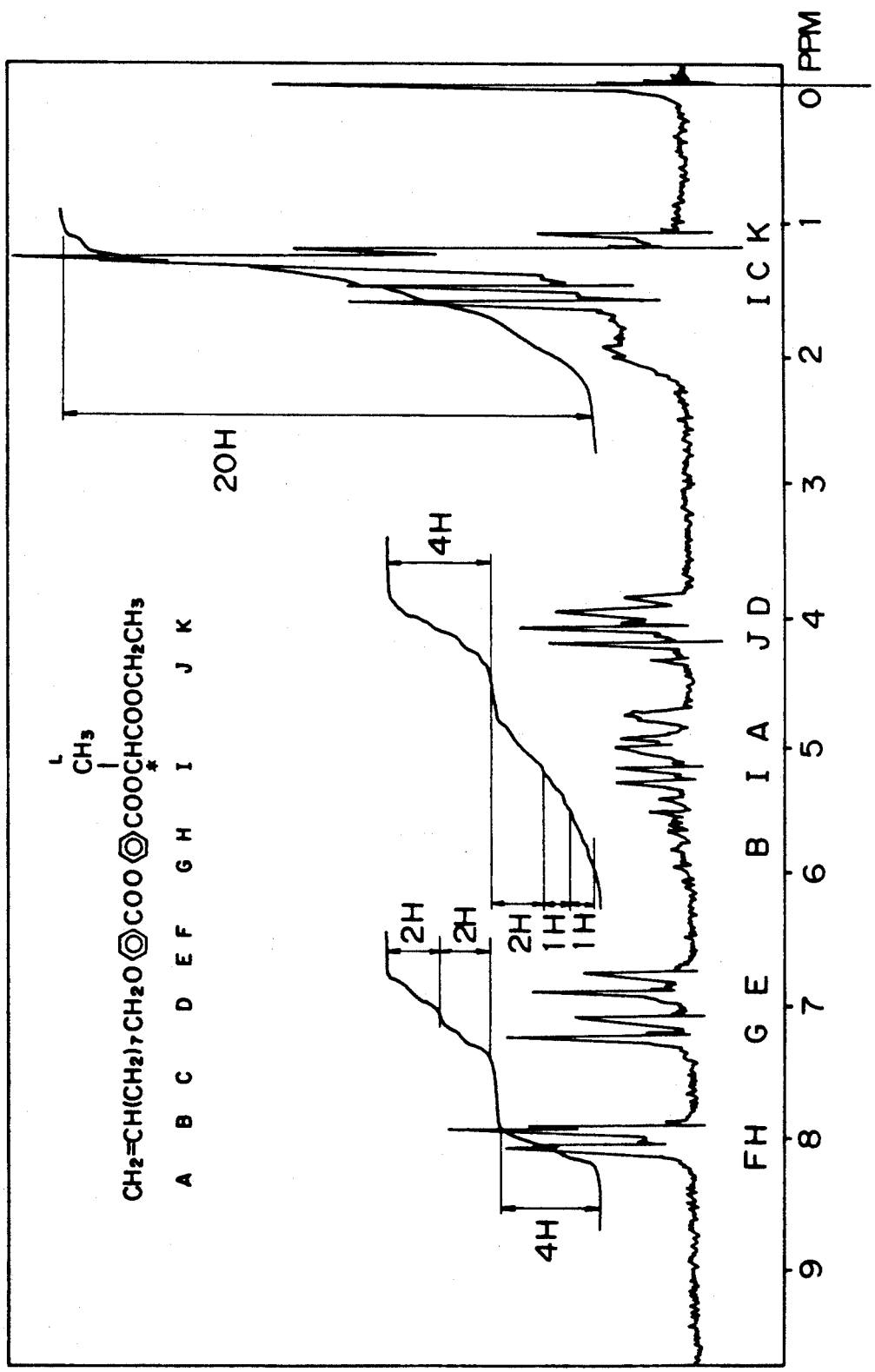
FIGS. 1 to 3 are charts showing $^1$H-NMR spectrum of the liquid-crystalline compounds obtained in Examples 1 to 3, respectively.

The preferred number average molecular weight of the liquid-crystalline polymers of the present invention is from 1,000 to 500,000. If the number average molecular weight is less than 1,000, the moldability of the liquid-crystalline polymers into film or coated film may be occasionally deteriorated. If it is more than 500,000, there may occasionally appear undesirable effects such as lowered response speed. The particularly preferred range of the number average molecular weight is generally from 1,000 to 100,000.

In the above general formulas (I) and (II), a, e, and r are each independently an integer having a value of 1 to 10, preferably 1 to 5.

In the above general formulas (I), (II), (III), and (IV), c, g, and w are each independently an integer having a value of 1 to 30, preferably 6 to 12.

In the liquid-crystalline copolymers having the repeating units represented by the general formulas (II) and (III), the copolymerization ratio of the repeating units (II) to the repeating units (III), i.e., the molar ratio m:n, is from 99:1 to 1:99, preferably from 90:10 to 10:90.

In the liquid-crystalline copolymers having the repeating units represented by the general furmulas (II), (IV), and (V), the copolymerization ratio between the repeating units (II), (IV), and (V), i.e., the molar ratio s:t:u, is 98:1:1–1:98:1–1:1:98, preferably 90:5:5–5:90:5–5:5:90.

The liquid-crystalline polymer of the present invention having the repeating units represented by the formula (II) may be obtained by polymerizing an epoxide represented by the following general formula (II'):

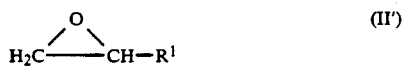

(II')

wherein R$^1$ is as defined above.

The liquid-crystalline copolymer of the present invention having the repeating units represented by the formula (II) and (III) may be obtained by copolymerizing the epoxides each represented by the following general formulas (II') and (III') respectively:

(II')

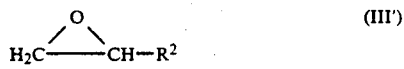

(III')

wherein R$^1$ and R$^2$ are as defined above.

The liquid-crystalline copolymer of the present invention having the repeating units represented by the formula (II), (IV), and (V) may be obtained by copolymerizing the epoxides each represented by the following general formulas (II'), (IV'), and (V') respectively:

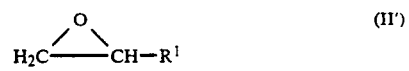

(II')

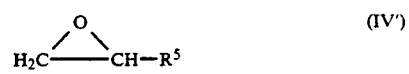

(IV')

(V')

wherein R$^1$, R$^5$, and R$^6$ are as defined above.

Among the liquid-crystalline polymers of the present invention, the above-described copolymers and terpolymers may be prepared by copolymerizing two epoxides both of which are monomers of the homopolymers of the present invention having the repeating units represented by the formula (II), or by copolymerizing the epoxides with epoxides which are monomers of non-liquid-crystalline polymers and/or epoxides which are monomers of known liquid-crystalline polymers having high response speeds, etc., whereby adjusting the SmC* phase temperature ranges of the resulting liquid-crystalline copolymers to temperatures around room temperature and elongating helical pitches to facilitate attainment of bistable state.

For instance, copolymerization of a two-cyclic skeleton-type epoxide and a three-cyclic skeleton-type epoxide produces a copolymer having a wide SmC* phase temperature including room temperature.

Copolymerization of two epoxides whose structure molecules are opposite in twisting direction of helix to each other makes the helical properties of the epoxides compensate each other in the produced copolymer, resulting in an extended helical pitch of the copolymer. Also, copolymerization of an epoxide having a helical structure with an epoxide without helical structure provides a copolymer wherein the helical property of the epoxide unit having a helical structure is weakened by the dilution effect of the epoxide unit without helical structure, resulting in an extended helical pitch of the obtained copolymer.

The epoxide (II') to be used for preparation of the liquid-crystalline polymers of the present invention is polymerized to form the liquid-crystalline homopolymers of the present invention or are copolymerized with other epoxides to construct the basic structure of the liquid-crystalline copolymers of the present invention, and the epoxides (II') have a substituent R$^1$ which comprises a spacer and a mesogenic group having at its end a specified optically active group.

The epoxide (III') is an epoxide different from the epoxide (II'), and its substituent R$^2$ may, in common with the substituent R$^1$ of the epoxide (II'), consist of a spacer and a mesogenic group having at its end an optically active group so far as the R$^2$ is different from the R$^1$, or may have a mesogenic group having no optically active end group, and further, may have no spacer nor mesogenic group, i.e., may be hydrogen or an alkyl group such as methyl group.

The epoxide (IV') is an epoxide different from the epoxide (II'), and the substituent R$^5$ may consist of a spacer and a mesogenic group having no optically active group at its end, or may consist of a spacer and a mesogenic group having at its end an optically active group so far as the $R^5$ is different from the $R^1$.

The epoxide (V') is an epoxide different from both the epoxides (II') and (IV'), and the substituent $R^6$ may, in common with the substituents $R^1$ and $R^5$ of the epoxides (II') and (IV'), consist of a spacer and a mesogenic group, and the mesogenic group may have at its end an optically active group, and further, the $R^6$ may also be a group having no spacer nor mesogenic group, i.e., hydrogen or an alkyl group such as methyl group.

For example, the liquid-crystalline compound (I) of the present invention may be synthesized by the following method.

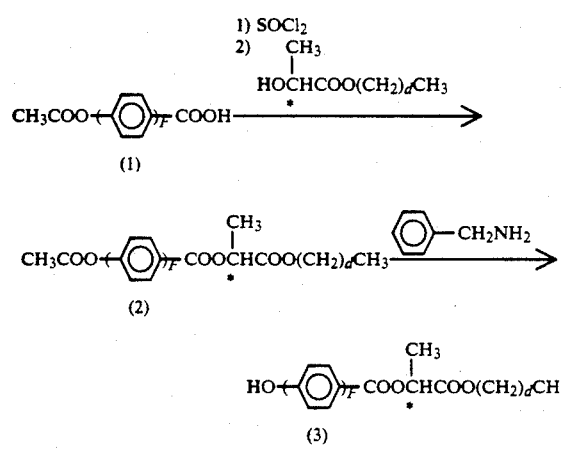

As shown by the above reaction formula, acetoxy(aromatic carboxylic acid)(1) (F is 1 or 2.) is halogenized with a halogenizing agent, such as thionyl chloride, to form an acid chloride, and the acid chloride is allowed to react with an alkyl lactate to obtain an ester compound (2). The ester compound (2) is allowed to reacted with benzylamine or the like to form a hydroxy compound (3).

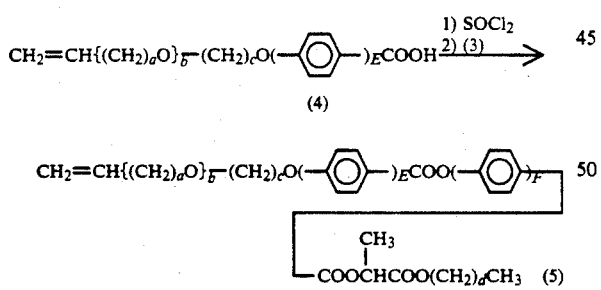

Subsequently, as shown by the above reaction formula, an aromatic carboxylic acid (4) having a terminal double bond (E is 1 or 2, but "E=2" and "F=2" are incompatible with each other.) is allowed to react with the above-described hydroxy compound (3), to obtain the objective liquid-crystalline compound (5).

The methods of preparing the epoxides represented by the general formulas (III'), (IV'), and (V') to be used for the preparation of the liquid-crystalline copolymers of the present invention will be described below, with priority given to the epoxide of the general formula (IV').

<1> In case where $R^5$ is

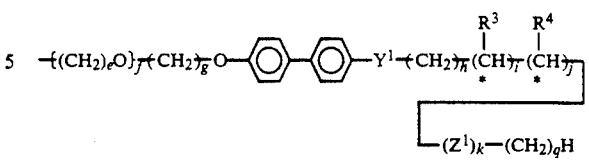

Hereinafter, the group

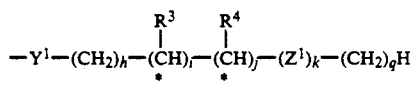

will be represented by "D".

As shown by the following reaction formula, an alkenol (6) is halogenized with a halogenizing agent, such as thionyl chloride, in the presence of pyridine, to obtain an alkene halide (7). The alkene halide (7) is allowed to react with a compound (8) in an appropriate solvent, such as 2-butanone, in the presence of an alkali, such as potassium carbonate, to obtain an ether compound (9). The ether compound (9) is then epoxidized with a peracid, such as m-chloroperbenzoic acid, in an appropriate solvent, such as dichloromethane, to obtain the objective epoxide (10).

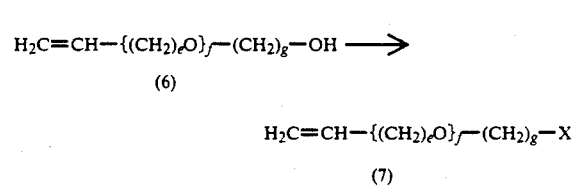

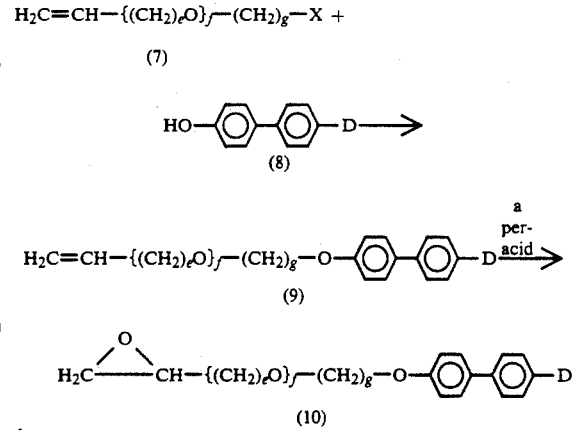

(In the above formula, X represents a halogen.)

The preferred alkenol (6) to be used includes, for example, 9-decene-1-ol, 11-dodecene-1-ol, 7-octene-1-ol, and 5-hexene-1-ol.

The above-mentioned compound (8),

may be synthesized as follows.
Hereinafter, the group

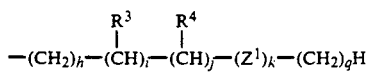

will be represented by "R".

Synthesis of

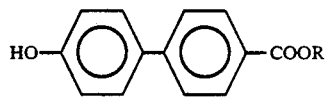

As shown by the following reaction formula, 4'-hydroxybiphenyl-4-carboxylic acid is allowed to react with an alcohol (11) in an appropriate solvent, such as benzene, in the presence of an esterification catalyst, such as concentrated sulfuric acid or p-toluenesulfonic acid, at a desired temperature, to obtain the ester compound (12).

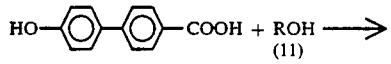

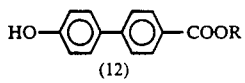

In case where an optically active group is to be introduced into the ester compound (12), an optically active alcohol is used as the alcohol (11). Some examples of the optically active alcohol to be used include, for example, (+)-2-methylbutanol, (−)-2-methylbutanol, (+)-2-chlorobutanol, (−)-2-chlorobutanol, (+)-2-chloropentanol, (−)-2-chloropentanol, (+)-2-methylpentanol, (−)-2-methylpentanol, (+)-3-methylpentanol, (−)-3-methylpentanol, (+)-4-methylhexanol, (−)-4-methylhexanol, (+)-2-chloropropanol, (−)-2-chloropropanol, (+)-1-methylheptanol, (−)-1-methylheptanol, (+)-6-methyloctanol, (−)-6-methyloctanol, (+)-2-cyanobutanol, (−)-2-cyanobutanol, (+)-2-butanol, (−)-2-butanol, (+)-2-pentanol, (−)-2-pentanol, (+)-2-octanol, (−)-2-octanol, (+)-2-fluorooctanol, (−)-2-fluorooctanol, (+)-2-fluorohexanol, (−)-2-fluorohexanol, (+)-2-fluorononanol, (−)-2-fluorononano, and (+)-2-chloro-3-methylpentanol, (−)-2-chloro-3-methylpentanol. Among these, the preferred are (−)-2-methylbutanol, (+)-2-butanol, (−)-2-pentanol, (−)-2-octanol, (−)-2-fluorooctanol, (−)-2-chloro-3-methylpentanol, and the like.

Some other examples of the optically active alcohol which may be used in the present invention include alkyl 2-hydroxypropionates (alkyl lactate), alkyl 2-chlroo-3-hydroxybutanoates, alkyl 3-hydroxy-2-methyl-4,4,4-trifluorobutanoates, ω-(2-methylbutoxy)-1-alkanols, 2-alkoxy-1-propanols, alkyl 2-fluoro-2-methyl-3-hydroxypropionates, alkyl 3-hydroxy-4,4,4-trifluorobutanoates, ω-(2-alkoxypropyloxy)-1-alkanols, ω-(2-chloropropyloxy)-1-alkanols, 2,3-dimethoxy-1-pentanol, and 2-alkoxy-1-methylethanols.

In case of preparing the epoxides (III'), (IV'), and (V') which have no optically active group in $R^2$, $R^5$, and $R^6$, an alcohol having no optically active group is used in place of optically active alcohols. Some examples of such alcohol which may be used include, for example, n-butyl alcohol, n-pentyl alcohol, n-hexyl alcohol, cyclohexyl alcohol, n-heptyl alcohol, n-octyl alcohol, n-nonyl alcohol, sec-butyl alcohol, and t-butyl alcohol.

Synthesis of

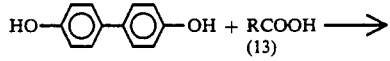

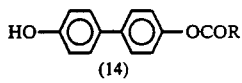

As shown by the following reaction formula, biphenyl-4,4'-diol is allowed to react with a carboxylic acid (13), to obtain the ester compound (14).

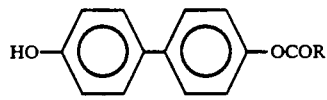

In case of introducing an optically active group, an optically active carboxylic acid is used as the carboxylic acid (14).

Some illustrative examples of the optically active carboxylic acid include, for example, (+)-2-methylbutanoic acid, (−)-2-methylbutanoic acid, (+)-2-chlorobutanoic acid, (−)-2-chlorobutanoic acid, (+)-2-methylpentanoic acid, (−)-2-methylpentanoic acid, (+)-3-methylpentanoic acid, (−)-3-methylpentanoic acid, (+)-4-methylhexanoic acid, (−)-4-methylhexanoic acid, (+)-2-chloropropanoic acid, (−)-2-chloropropanoic acid, (+)-6-methyloctanoic acid, (−)-6-methyloctanoic acid, (+)-2-cyanobutanoic acid, (−)-2-cyanobutanoic acid, (+)-2-flurooctanoic acid, (−)-2-fluorooctanoic acid, (+)-2-fluorohexanoic acid, (−)-2-fluorohexanoic acid, (+)-2-fluorononanoic acid, (−)-2-fluorononanoic acid, (+)-2-chloro-3-methylpentanoic acid, (−)-2-chloro-3-methylpentanoic acid, and 2-alkoxypropionic acids.

In case where the substituents of the epoxides have no optically active group, carboxylic acid having no optically active group is used in place of optically active carboxylic acids. Some examples of such carboxylic acid include, for example, n-butanoic acid, n-pentanoic acid, and n-hexanoic acid.

Synthesis of

As shown by the following reaction formula, the above-described alcohol (11) is tosylated, and the tosylated product is then allowed to react with bipheny-4,4'-diol, to obtain the ether compound (15).

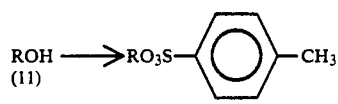

-continued

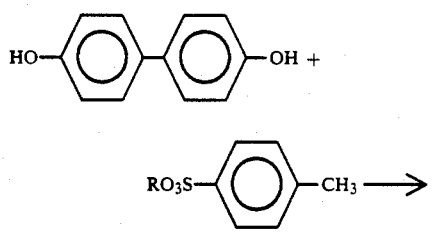

aqueous potassium hydroxide solution, hydrochloric acid or the like, to form a carboxylic acid compound. A halogenizing agent, such as thionyl chloride, is then added to the carboxylic acid compound, and the mixture is heated in a solvent, such as toluene, to form an acid halide. The acid halide is then allowed to react with the above-described compound (8) in a solvent, such as toluene, in the presence of pyridine, to obtain an ester compound (16). The ester compound (16) is epoxidized with a peracid, such as m-chloroperbenzoic acid, in a proper solvent, such as dichloromethane, to obtain the objective epoxide (17)

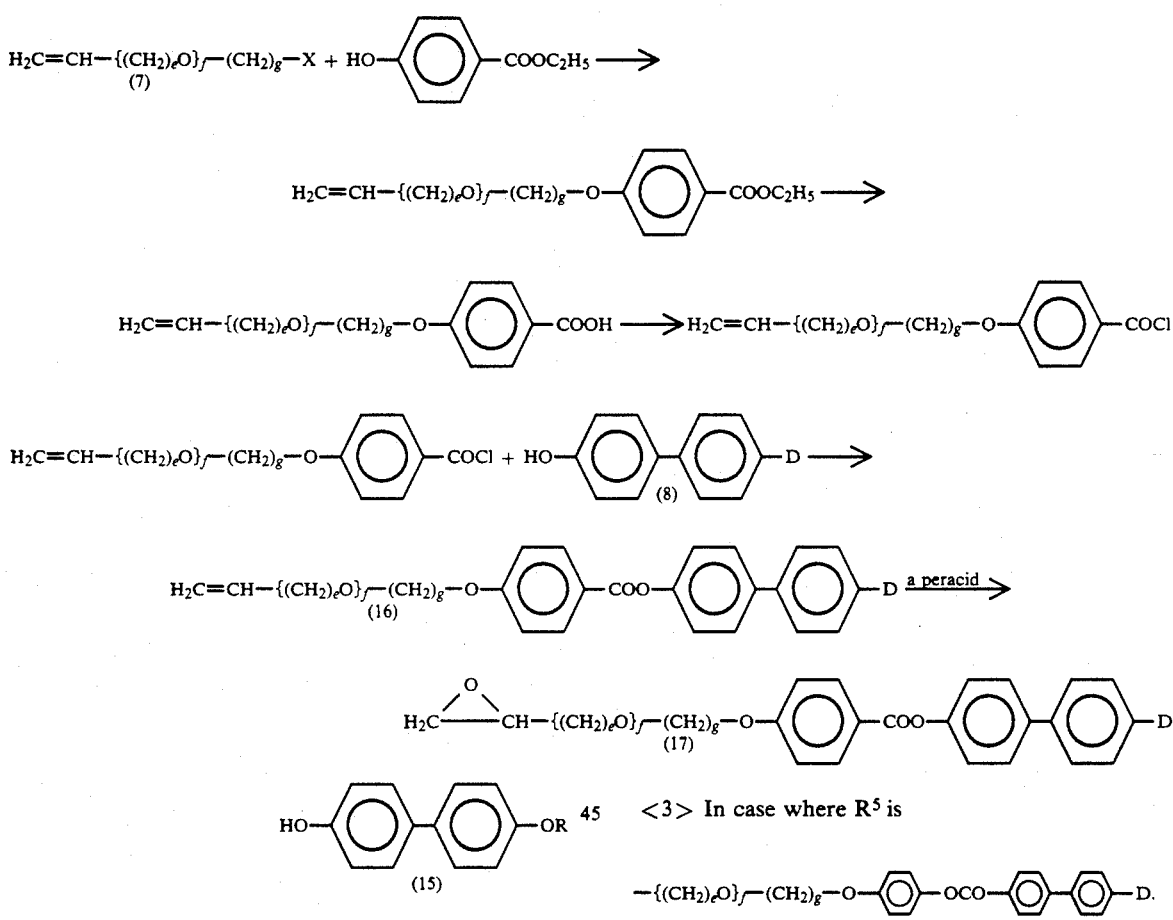

<2> In case where $R^5$ is

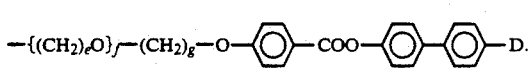

As shown by the following reaction formula, an alkene halide (7) is allowed to react with ethyl p-hydroxybenzoate in a proper solvent, such as acetone, in the presence of an alkali, such as potassium carbonate, to obtain an ether compound. Subsequently, the group protecting the carboxylic group of the ether compound is eliminated from the ether compound by using an <3> In case where $R^5$ is $-\{(CH_2)_eO\}_f-(CH_2)_g-O-\langle\bigcirc\rangle-OCO-\langle\bigcirc\rangle-\langle\bigcirc\rangle-D.$ As shown by the following reaction formula, an alkene halide (7) is allowed to react with hydroquinone in the presence of an alkali, such as potassium carbonate, to obtain an ether compound (18).

The following compound (19) is converted into an acid chloride by using thionyl chloride or the like. The obtained acid chloride is allowed to react with the ether compound (18) in the presence of pyridine, to obtain an ester compound (20). Thereafter, epoxidation is carried out in the same manner as in <1>, to obtain the objective epoxide (21).

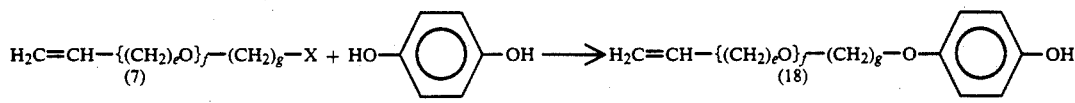

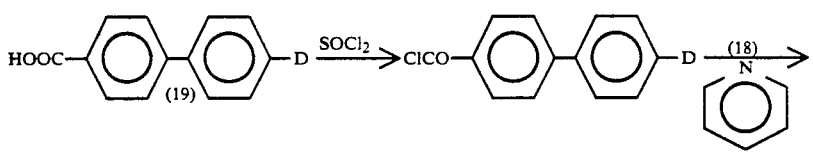

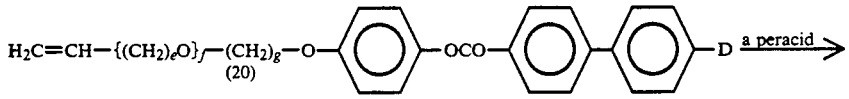

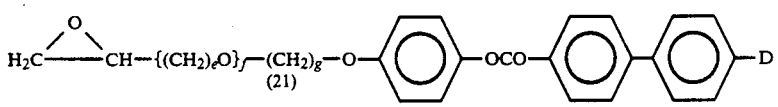

The above-described compound (19),

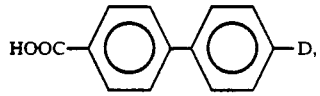

may be prepared as follows.

Synthesis of

An alcohol (11) is allowed to react with biphenyl-4,4'-dicarboxylic acid in a solvent, such as toluene, in the presence of an esterification catalyst, to obtain the objective ester compound (22).

Synthesis of

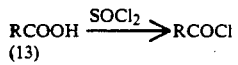

A carboxylic acid (13) is converted into an acid chloride by using thionyl chloride or the like, and the acid chloride is then allowed to react with 4'-hydroxybiphenyl-4-carboxylic acid in the presence of pyridine, to obtain the objective ester compound (23).

$$RCOOH \xrightarrow{SOCl_2} RCOCl$$
(13)

-continued

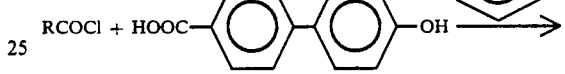

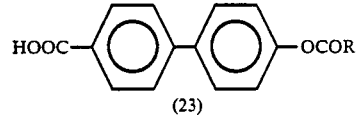

Synthesis of

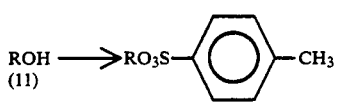

Ethyl 4'-hydroxybiphenyl-4-carboxylate is allowed to react with an ester of p-toluenesulfonic acid prepared by tosylating an alcohol (11), in the presence of potassium carbonate or the like, to obtain an ether compound. The ether compound is allowed to react with an aqueous alkali solution to hydrolyze the ester portion of the protecting group, to obtain the objective compound (24).

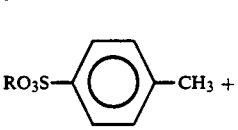

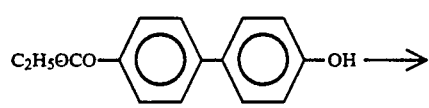

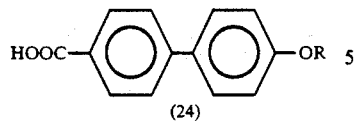

(24)

<4> In case where $R^5$ is

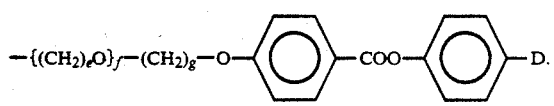

The objective epoxide (26) may be prepared by employing the method <2> for preparing the epoxide where $R^5$ is

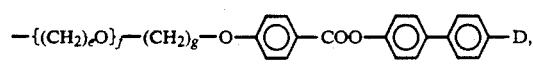

with the proviso a compound (25),

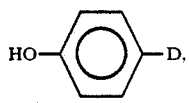

is used in place of the compound (8),

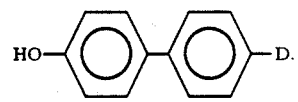

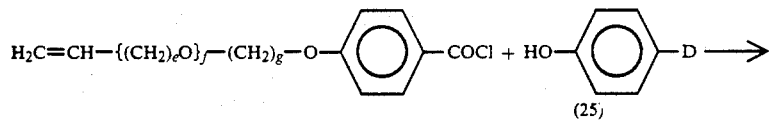

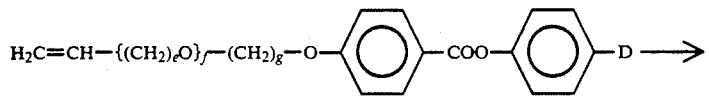

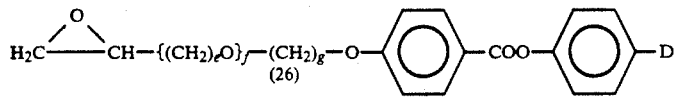

The above-described compound (25) may be prepared as follows.

Synthesis of

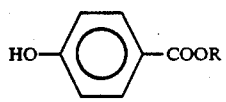

The objective ester compound (27) may be prepared by using the method for synthesis of the compound (12) in <1>, with the proviso p-hydroxybenzoic acid is used in place of 4'-hydroxybiphenyl-4-carboxylic acid.

Synthesis of

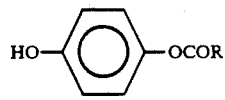

The objective ester compound (28) may be prepared by using the method for synthesis of the compound (14) in <1>, with the proviso hydroquinone is used in place of biphenyl-4,4'-diol.

Synthesis of

The objective ether compound (29) may be prepared by using the method for synthesis of the compound (15) in <1>, with the proviso hydroquinone is used in place of biphenyl-4,4'-diol.

<5> In case where $R^5$ is

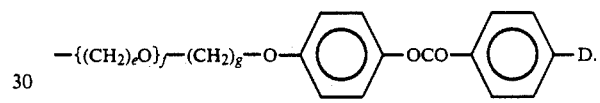

The objective epoxide represented by the following general formula (31) may be prepared by using the method <3> for synthesis of the epoxide wherein $R^5$ is

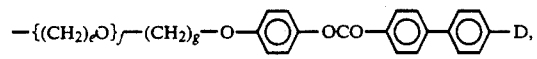

with the proviso a compound (30),

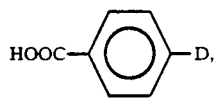

is used in place of the compound (19),

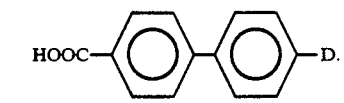

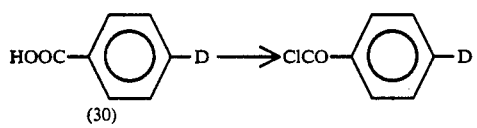
(30)

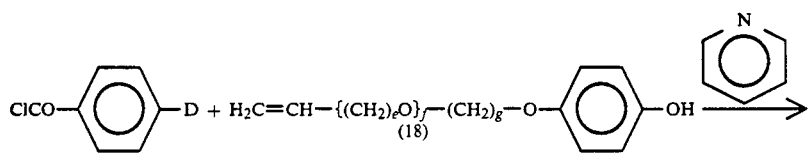

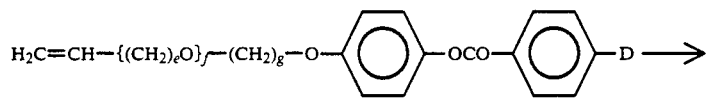

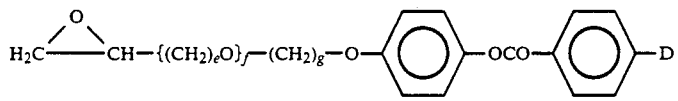

The above compound (30) may be prepared as follows.

Synthesis of

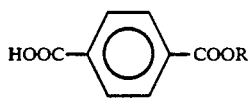

The objective ester compound (32) may be prepared by the method for synthesis of the compound (22) in the above <3>, with the proviso terephthalic acid is used in place of biphenyl-4,4'-dicarboxylic acid.

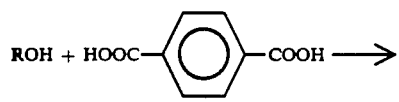

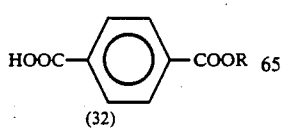
(32)

Synthesis of

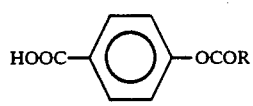

The objective ester compound (33) may be prepared by the method for synthesis of the compound (23) in the above <3>, with the proviso p-hydroxybenzoic acid is used in place of 4'-hydroxybiphenyl-4-carboxylic acid.

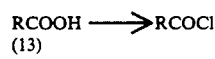
(13)

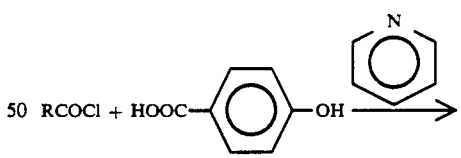

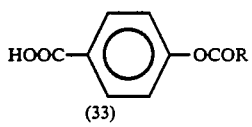
(33)

Synthesis of

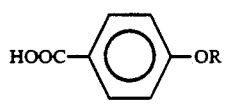

The objective ether compound (34) may be prepared by the method for synthesis of the compound (24) in the above <3>, with the proviso ethyl p-hydroxybenzoate is used in place of ethyl 4'-hydroxybiphenyl-4-carboxylate.

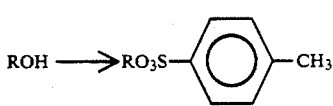

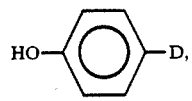

is used in place of the compound (8),

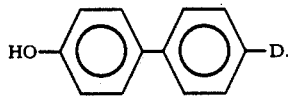

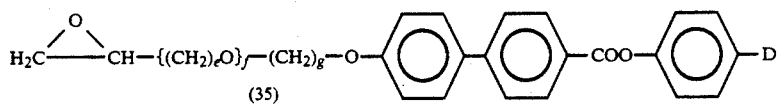
(35)

<7> In case where $R^5$ is

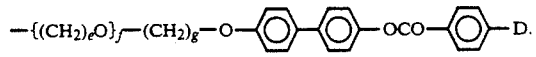

The objective epoxide (36) may be prepared by the method <3> for synthesis of the epoxide wherein $R^5$ is

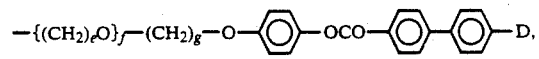

with the proviso biphenyl-4,4'-diol is used in place of hydroquinone, and the above-described compound (30),

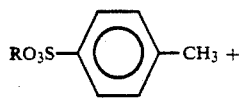

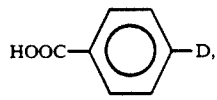

is used in place of the compound (19),

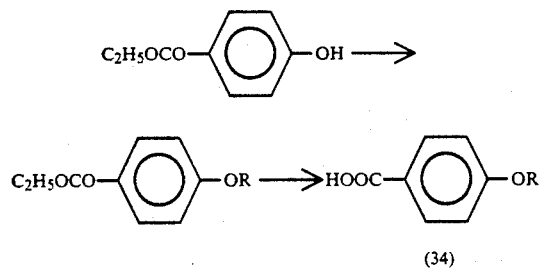
(34)

<6> In case where $R^5$ is

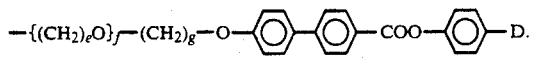

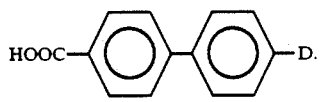

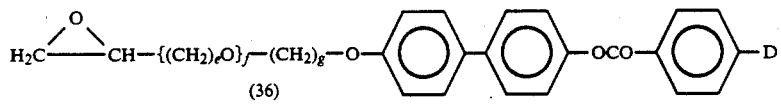
(36)

The objective epoxide (35) may be prepared by the method <2> for synthesis of the epoxide wherein $R_5$ is

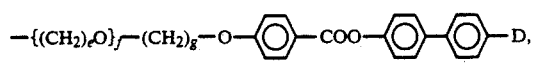

with the proviso ethyl 4'-hydroxybiphenyl-4-carboxylate is used in place of ethyl p-hydroxybenzoate, and the above-described compound (25), The liquid-crystalline polymer of the present invention may be prepared by polymerizing thus obtained one, two or three monomers, and the polymerization can be performed by using known cationic polymerization methods, or the like.

The catalysts that may be used for cationic polymerization in the present invention are known ones including protonic acids, such as sulfuric acid, phosphoric acid or perchloric acid, lewis acids, such as boron trifluoride, aluminum chloride, titanium tetrachloride or stannic chloride, boron trifluoride etherate, etc. Among these catalysts, stannic chloride may be suitably used.

It is also possible to prepare the polymers of the present invention by coordination polymerization by using organic aluminum complexes, etc. as a catalyst. In this case, polymers having number average molecular weights of not less than 30,000 can be obtained.

The polymerization techniques that may be employed in the present invention are bulk polymerization technique, slurry polymerization technique, solution polymerization technique, etc., preferably solution polymerization technique.

The suitable polymerization temperature can be usually from 0° to 30° C., although it is not uniformly specified since it varies depending on the kind of the catalyst.

The suitable polymerization time can be usually from several hours to six days, although it varies depending on the other polymerization conditions including polymerization temperature, etc.

Control of the molecular weight of the copolymers may be conducted by adding a known molecular weight regulator and/or controlling the concentration of catalyst to monomers.

When bulk polymerization technique is employed, the resulting polymers may be directly fixed between a couple of substrates in a state adhering to the substrates by sufficiently mixing the monomers with an initiator, sufficiently de-aerating the mixture, introducing the mixture between two substrates such as glass substrates, and heating the mixture.

The solvents to be used in slurry polymerization and solution polymerization may be any known inert solvent. The illustrative examples of the solvents to be suitably used include hexane, dichloromethane or aromatic solvents, such as benzene, toluene, and xylene.

It is not essential but preferable to replace the atmosphere of the reaction system with an inert gas, such as argon or nitrogen, at the time of polymerization reaction and the above-described epoxidation reaction.

Thus obtained liquid-crystalline polymers of the present invention may be blended with other optically active compounds, and may be used in a form of film by forming them into film by using a known film forming technique, such as casting technique, T-die technique, inflation technique, calender technique, stretching technique or the like. Thus obtained films of the liquid-crystalline polymers of the present invention may be utilized in various optoelectronics fields, including liquid crystal displays, electronic optical shutters, electronic optical diaphragms, and the like, by disposing them between a couple of large glass substrates, curved glass substrates, polyester films, etc., not to mention two usual glass substrates.

Further, the liquid-crystalline polymers may also be directly formed into film adhering to a substrate by dissolving a liquid-crystalline polymer in a suitable solvent, applying the resulting polymer solution to a surface of a substrate, such as glass substrate, and then evaporating the solvent.

It was confirmed that the liquid-crystalline polymers of the present invention exhibit ferroelectricity over a wide temperature range including temperatures around room temperature. It was also confirmed that they perform high speed response to electric field at temperatures around room temperature.

Because the liquid-crystalline polymers of the present invention excel in moldability, they have a large possibility of usage in the fields of integrated optics, optoelectronics, and information memory. For instance, the liquid-crystalline polymers of the present invention may be used for various electronic optical devices, for example, for liquid crystal displays, such as digital displays of various forms, electronic optical shutters, optical-path transfer switches in optical communication systems, electronic optical diaphragms, memory devices, optical modulators, liquid crystal optical printer heads, and varifocal lenses.

At need, the liquid-crystalline polymers of the present invention may be further improved by various treatments well known in this industry, for example, by mixing two or more liquid-crystalline polymers of the present invention, by mixing them with other polymers or other liquid-crystalline compounds, or by addition of additives such as various inorganic or organic compounds or metals, including adhesives, stabilizers, plasticizers, etc.

In order to fully and clearly illustrate the present invention, the following examples are presented. It is intended that the examples be considered illustrative rather than limiting the invention disclosed and claimed herein.

EXAMPLES 1 to 27 AND COMPARATIVE EXAMPLES 1 AND 2

The structures of the liquid-crystalline compounds obtained in the following Examples were identified by NMR spectrum and elementary analysis, and the structures of the liquid-crystalline polymers obtained in the following Examples were identified by NMR spectrum. Since the composition ratio of ethylene oxide unit in copolymers cannot be determined accurately by NMR spectrum, the composition ratio of the ethylene oxide unit in Example 18 was substituted by charging ratio. The average molecular weights Mn of the polymers are shown in polystyrene-conversion values as measured by GPC. Measurement of phase transition temperature and confirmation of phases were conducted by using a DSC and a polarizing microscope, respectively.

Figure 2:
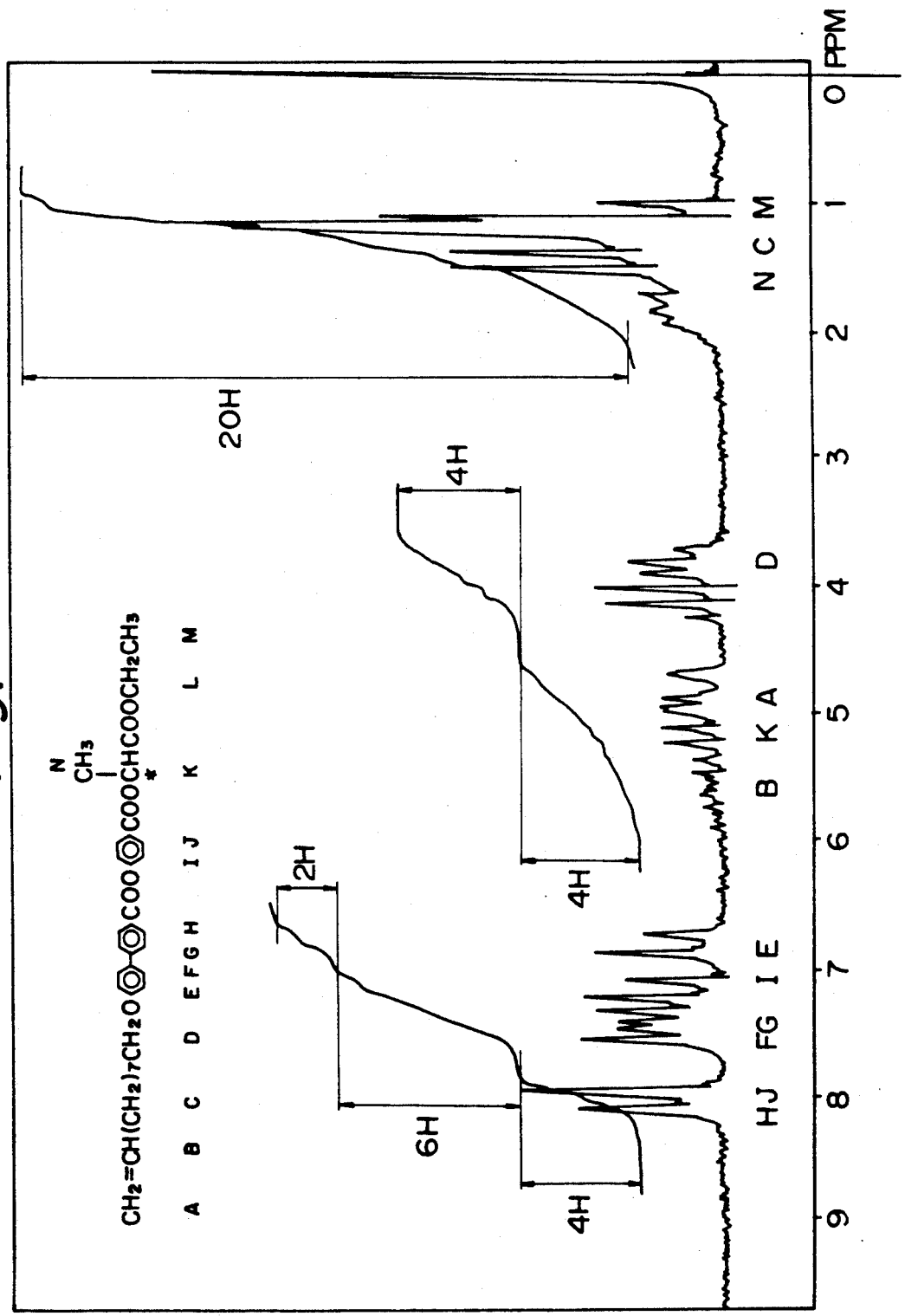
Figure 3:
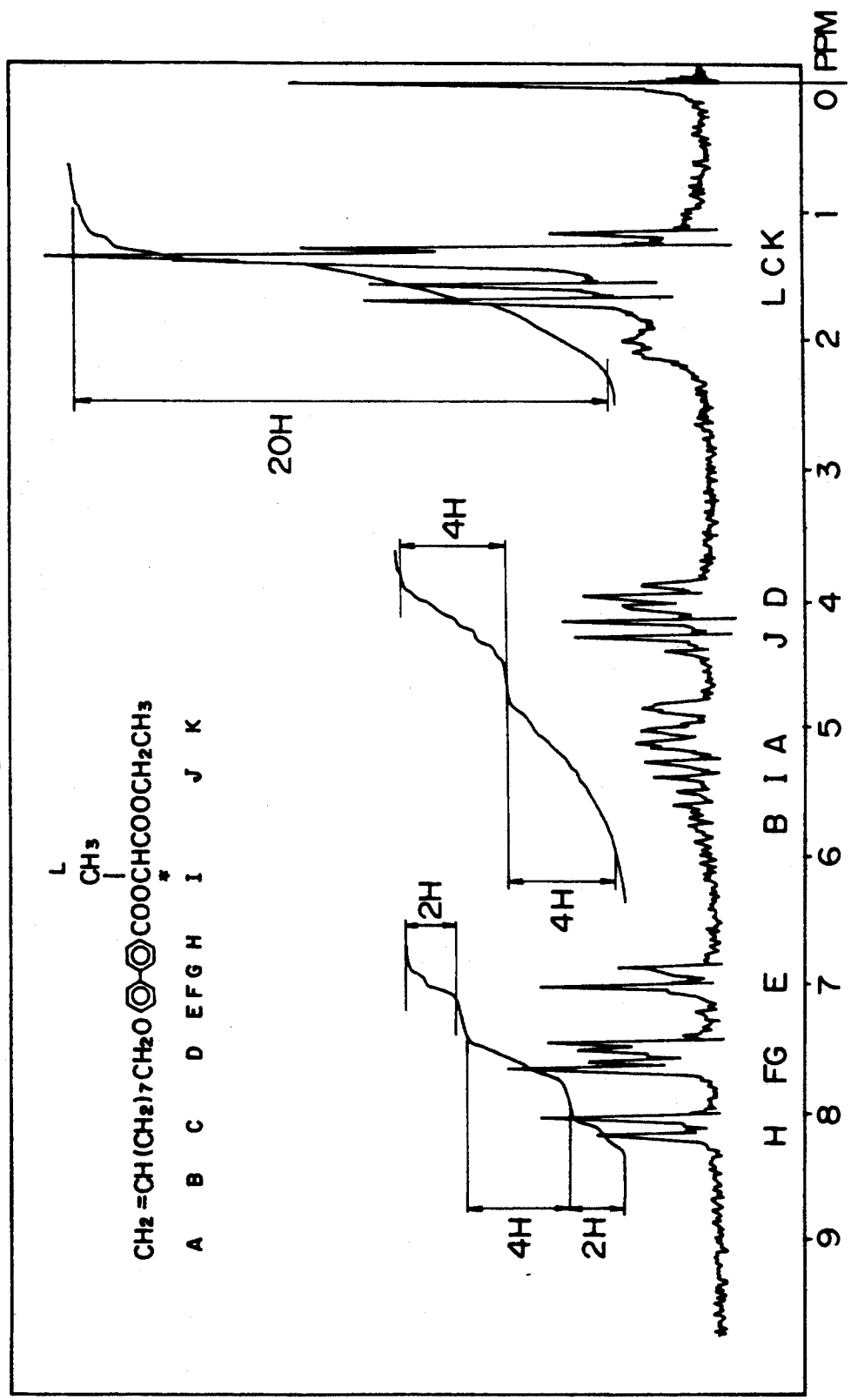
Figure 4:
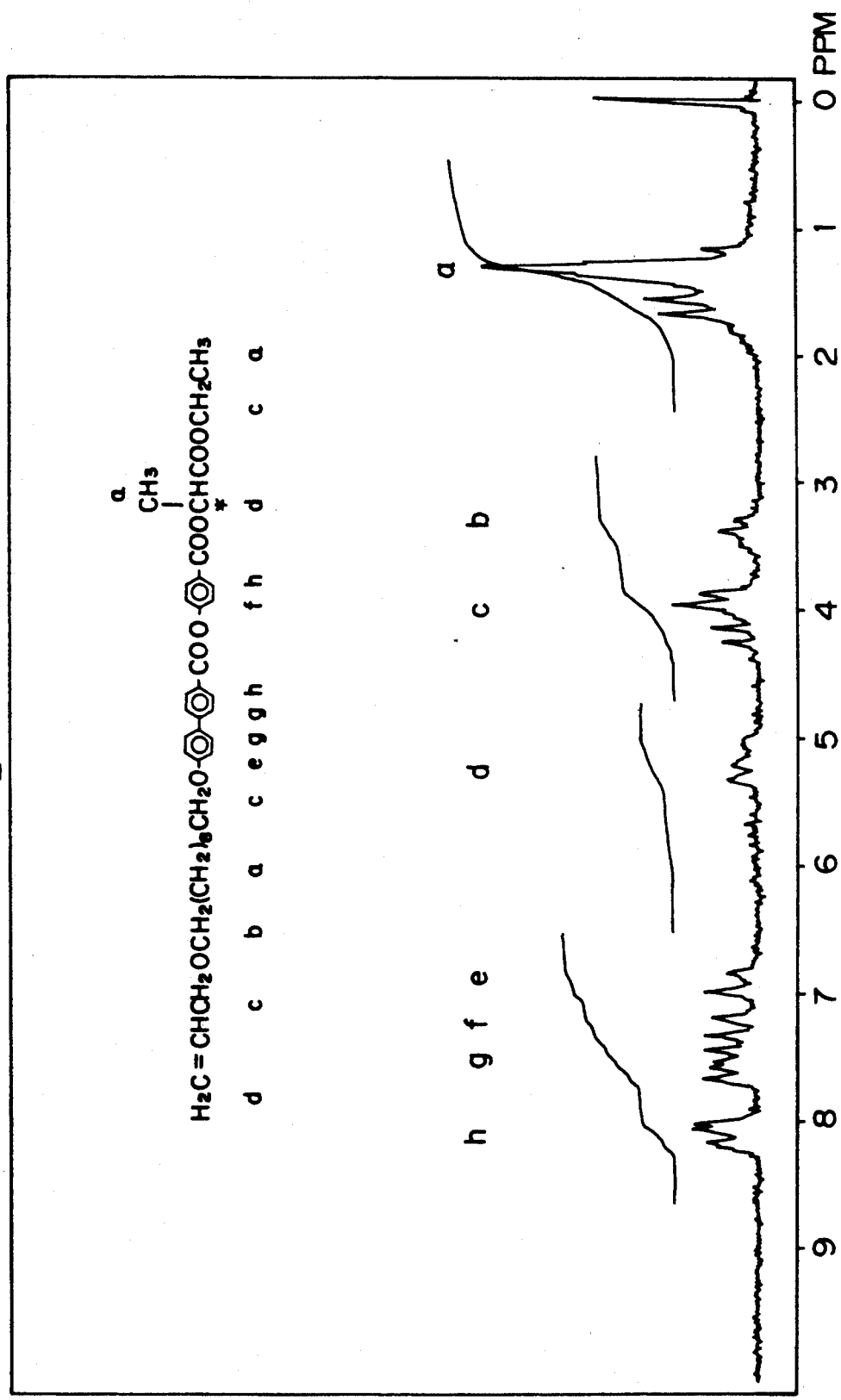
FIGS. 4 to 8 are charts showing $^1$H-NMR spectrum of the liquid-crystalline compounds obtained in Examples 5 to 9, respectively.
Figure 5:
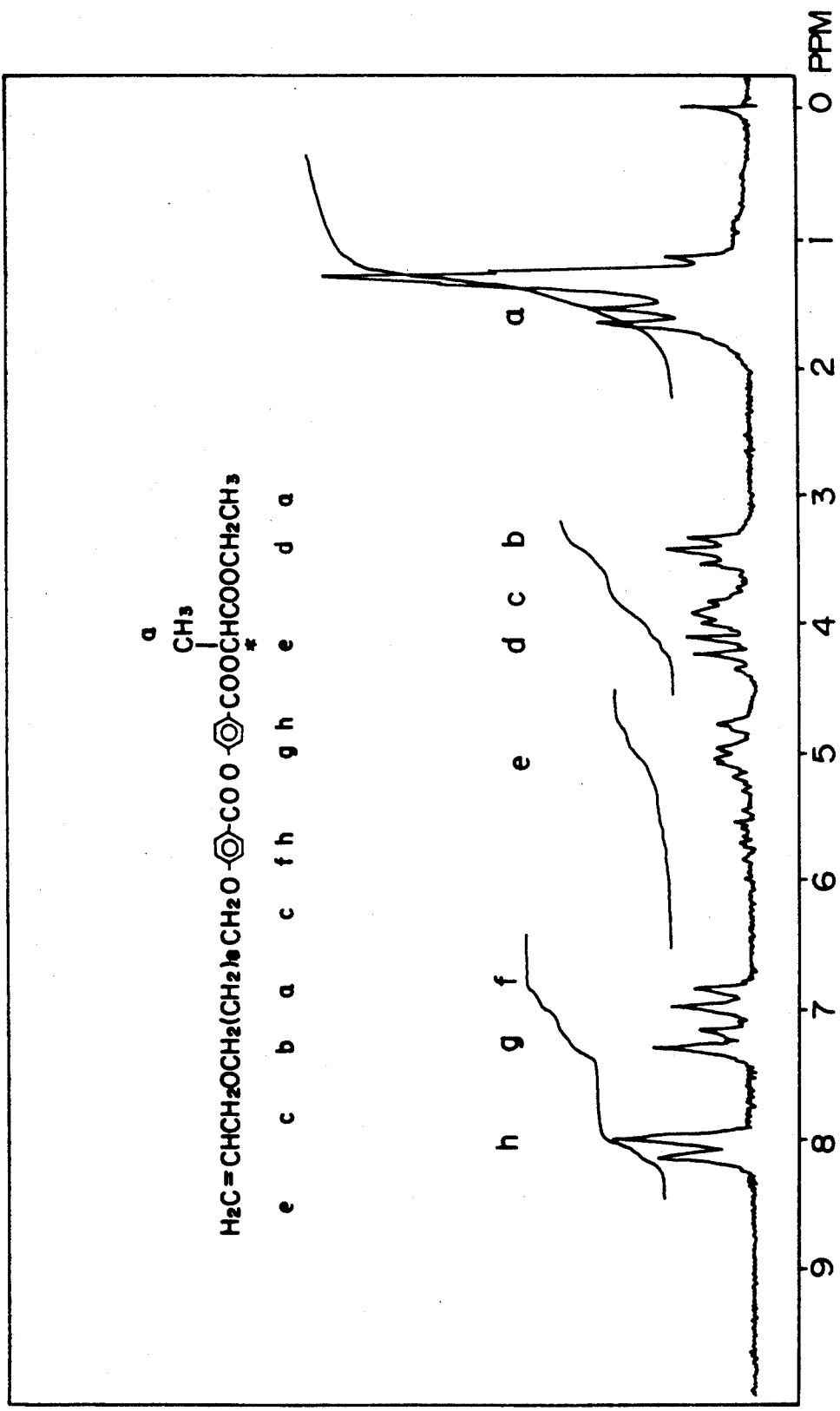
Figure 6:
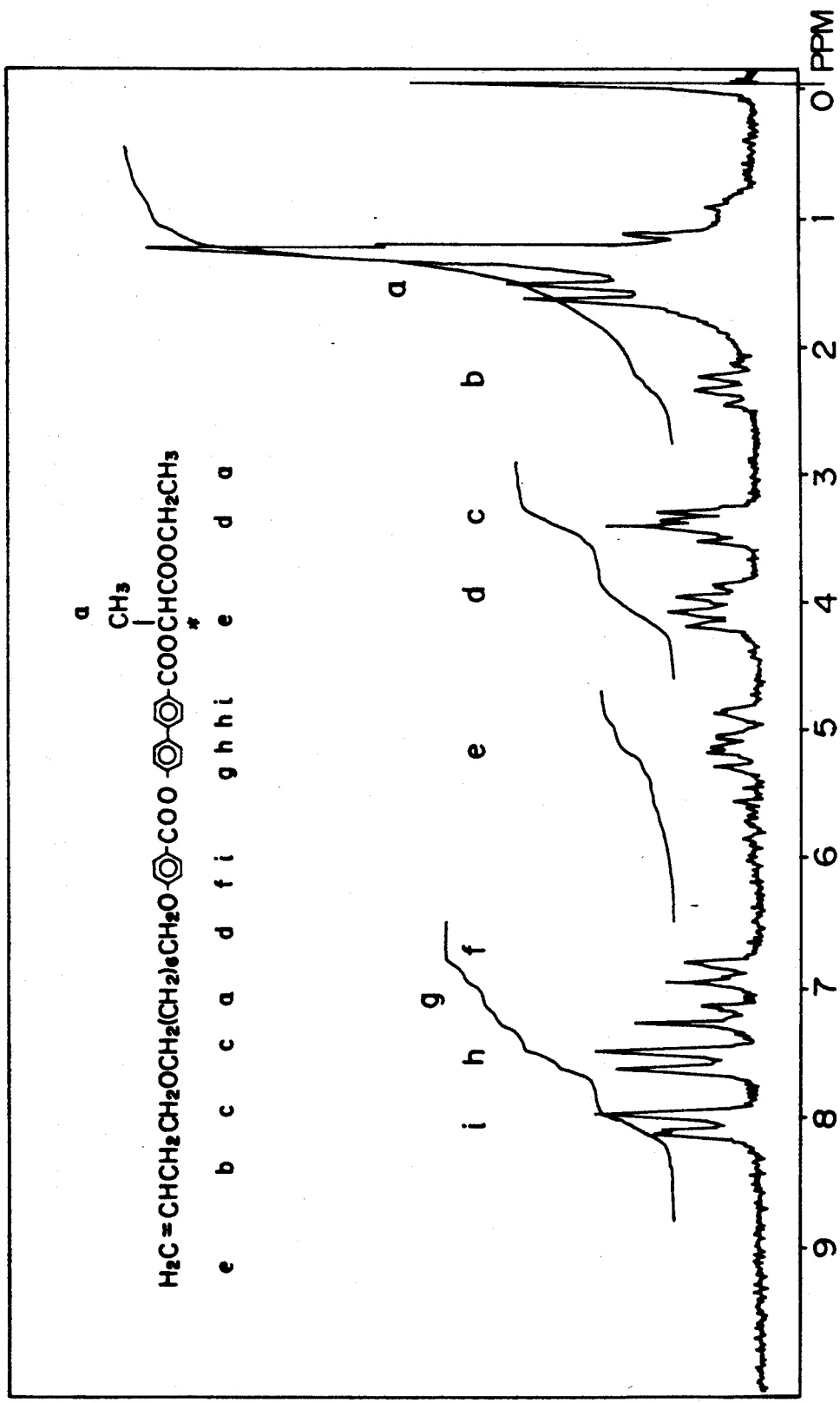
Figure 7:
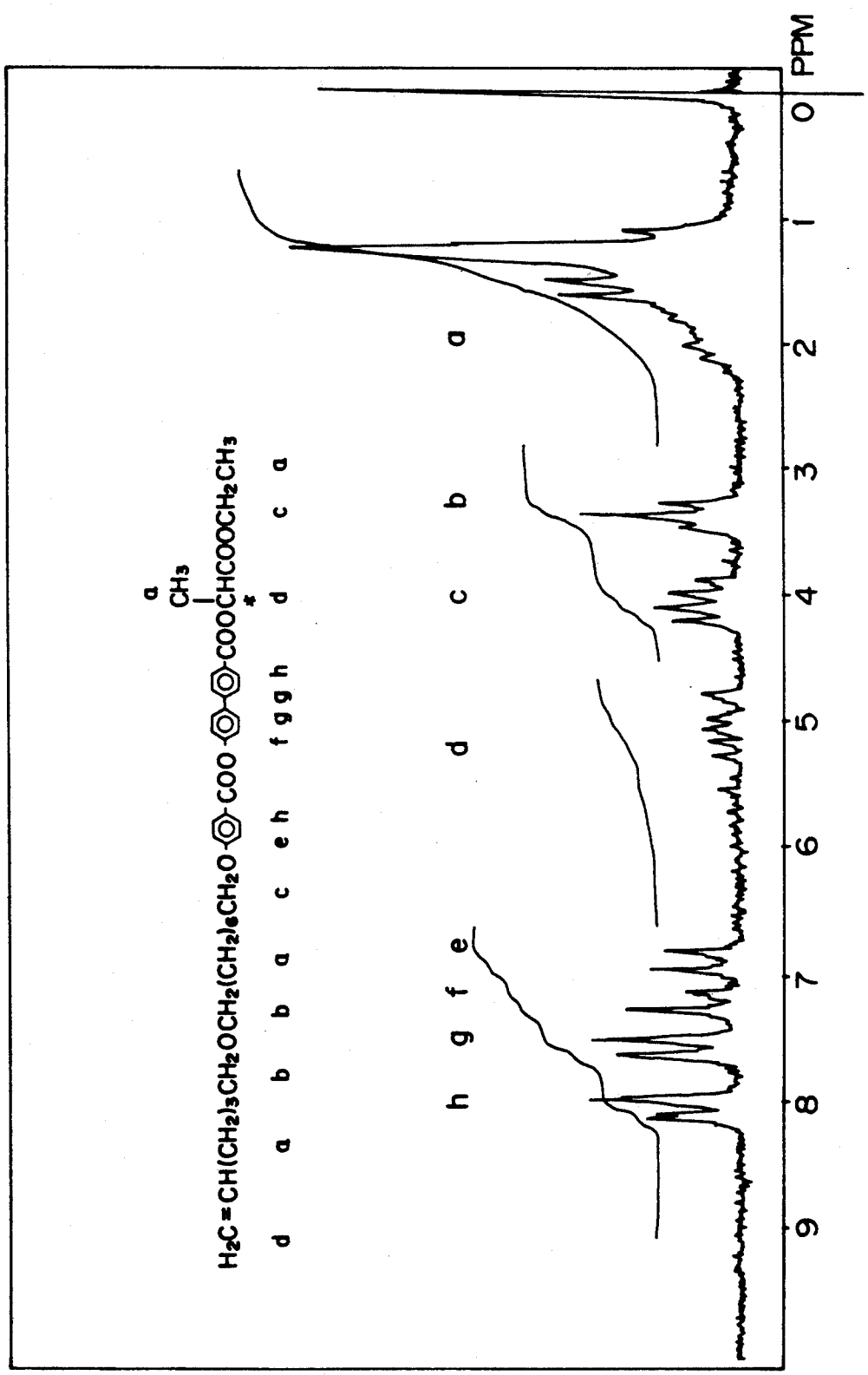
Figure 8:
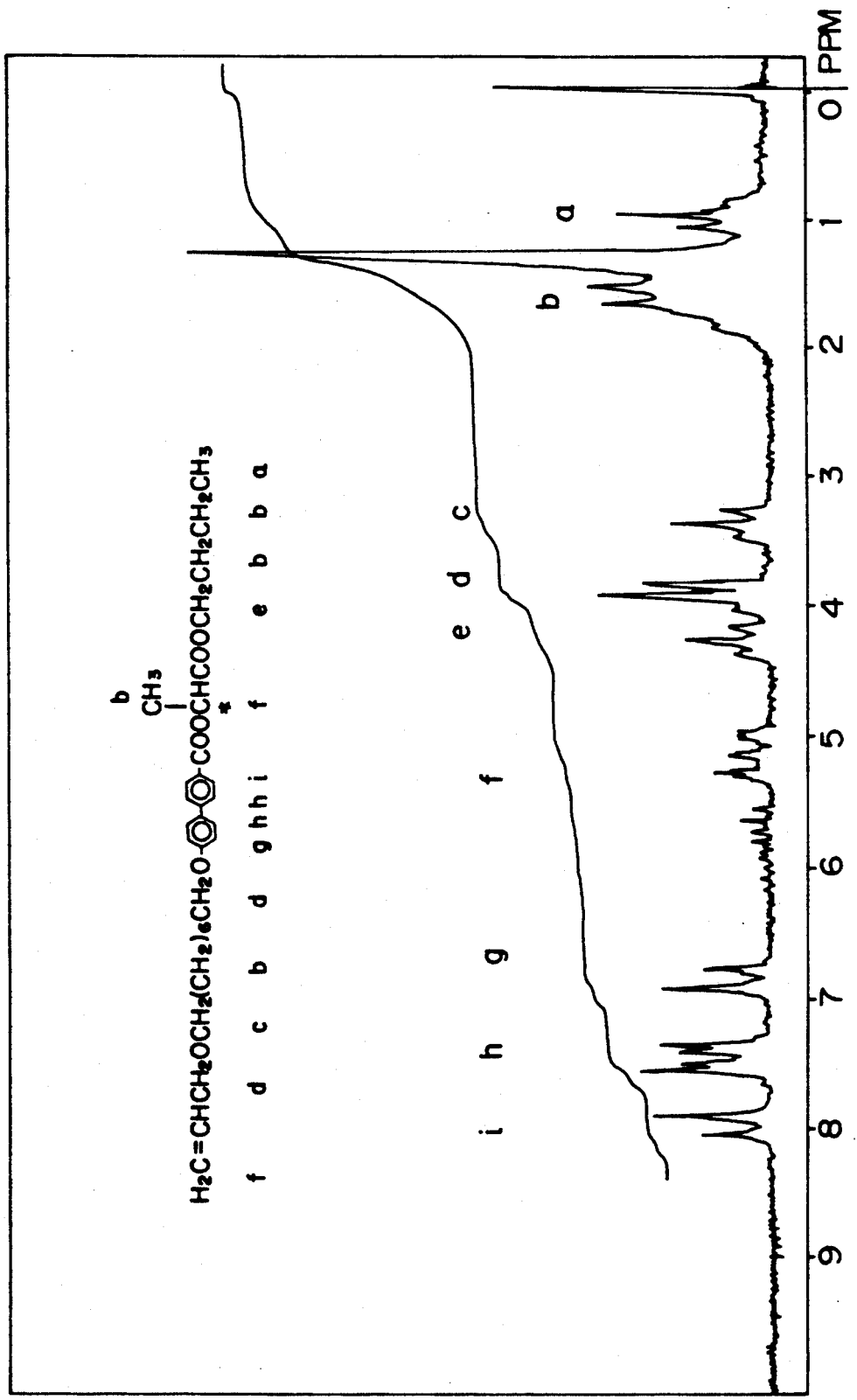
Figure 9:
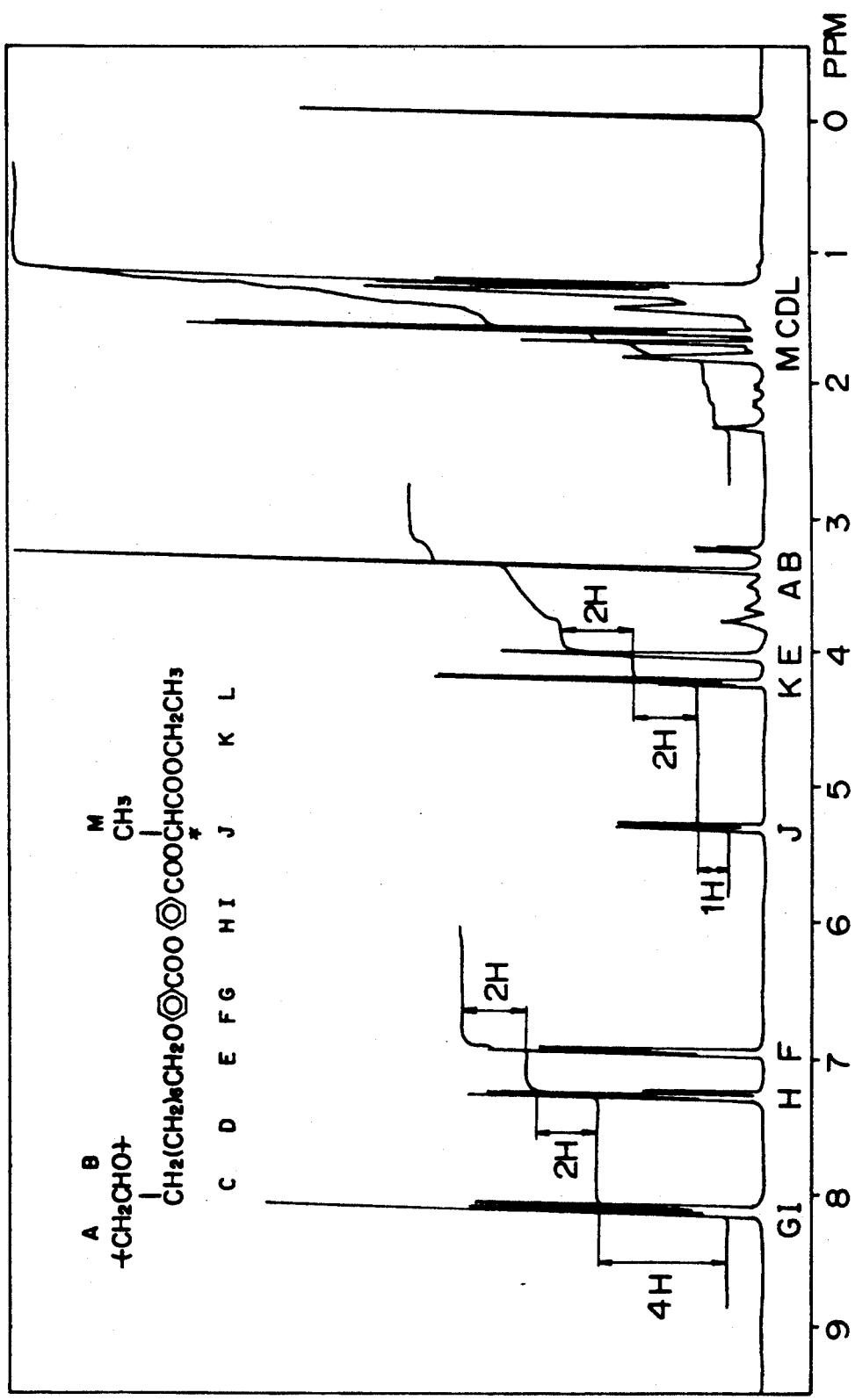
FIGS. 9 to 11 are charts showing $^1$H-NMR spectrum of the liquid-crystalline polymers obtained in Examples 10 to 12, respectively.
Figure 10:
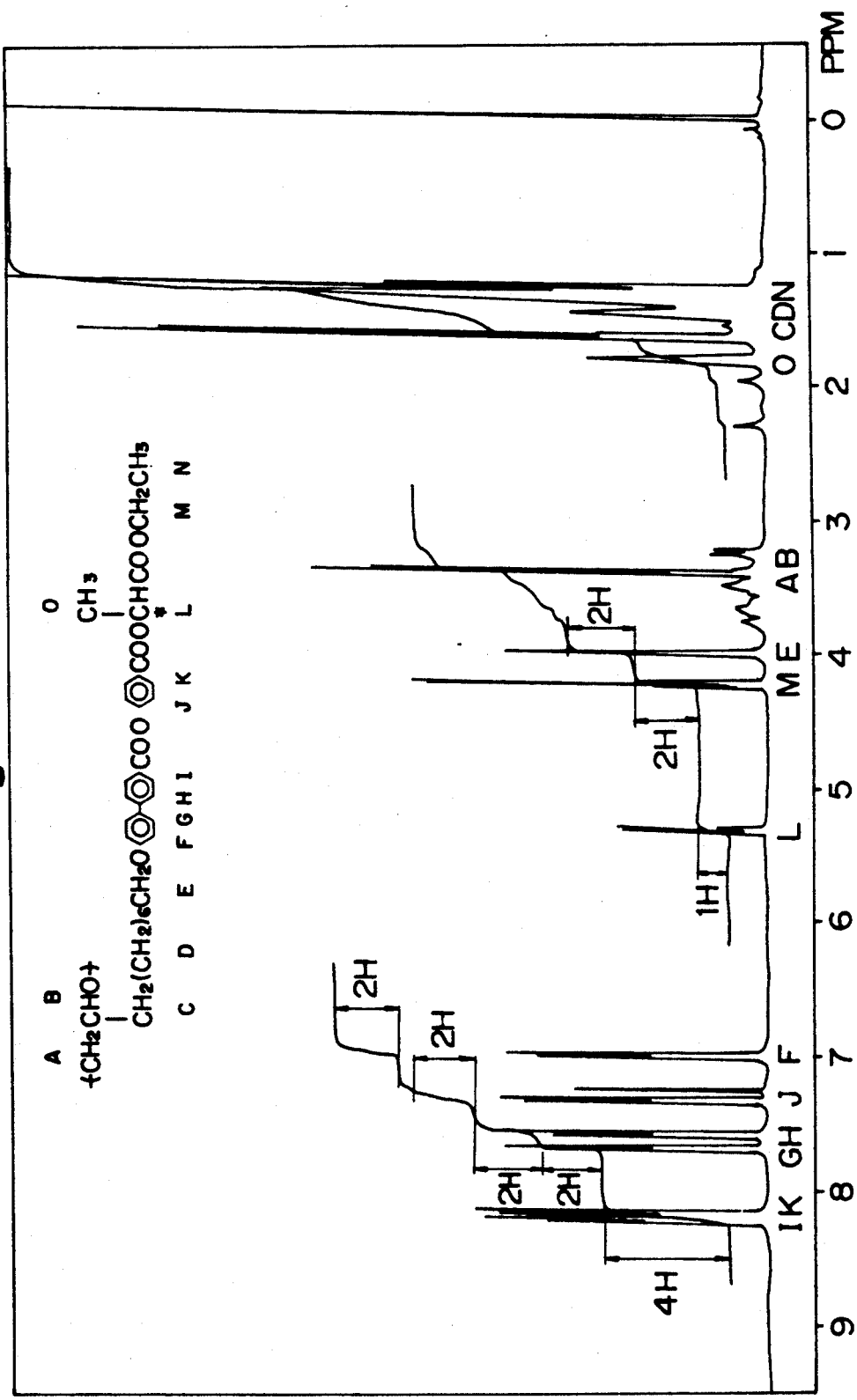
Figure 11:
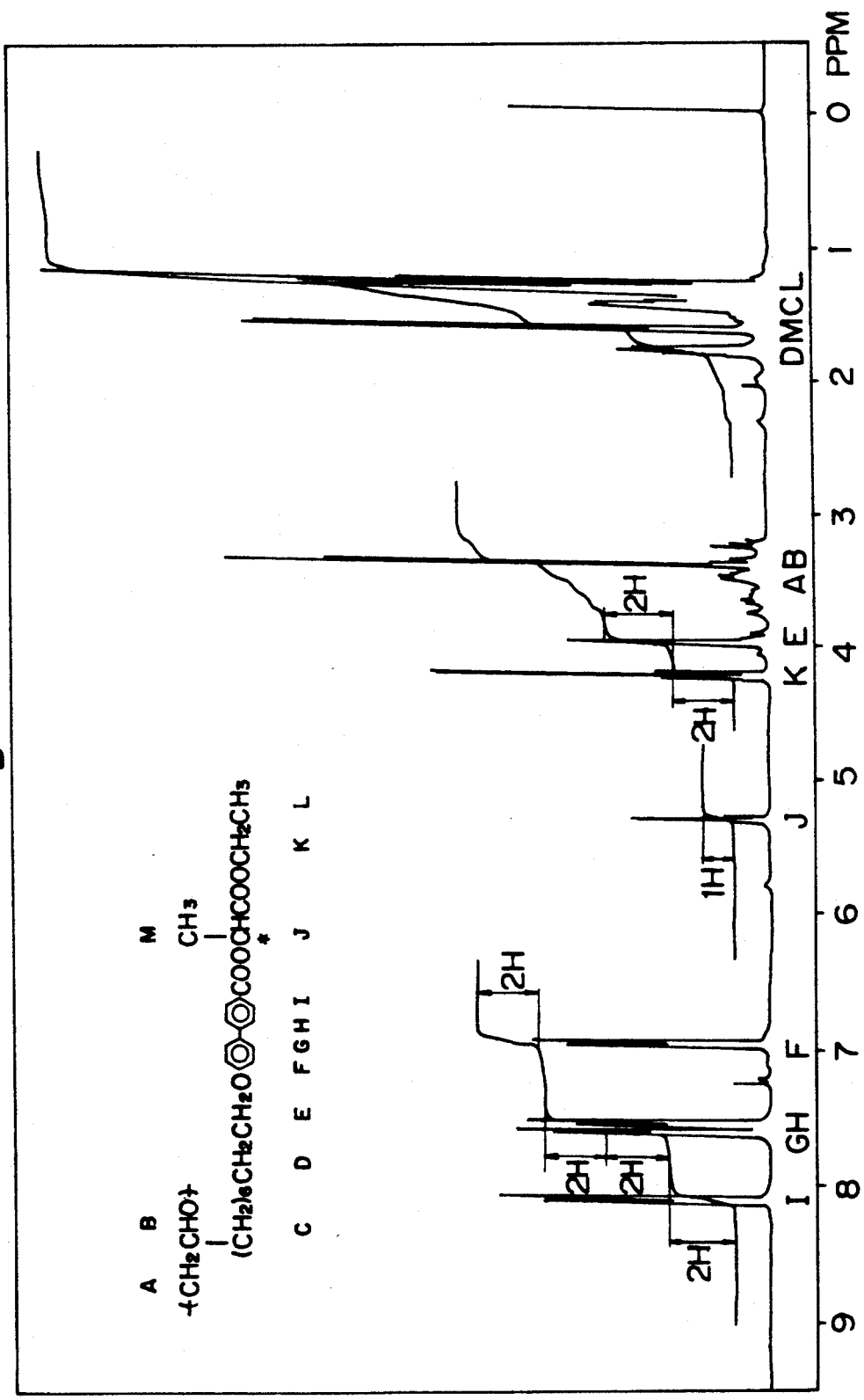
Figure 12:
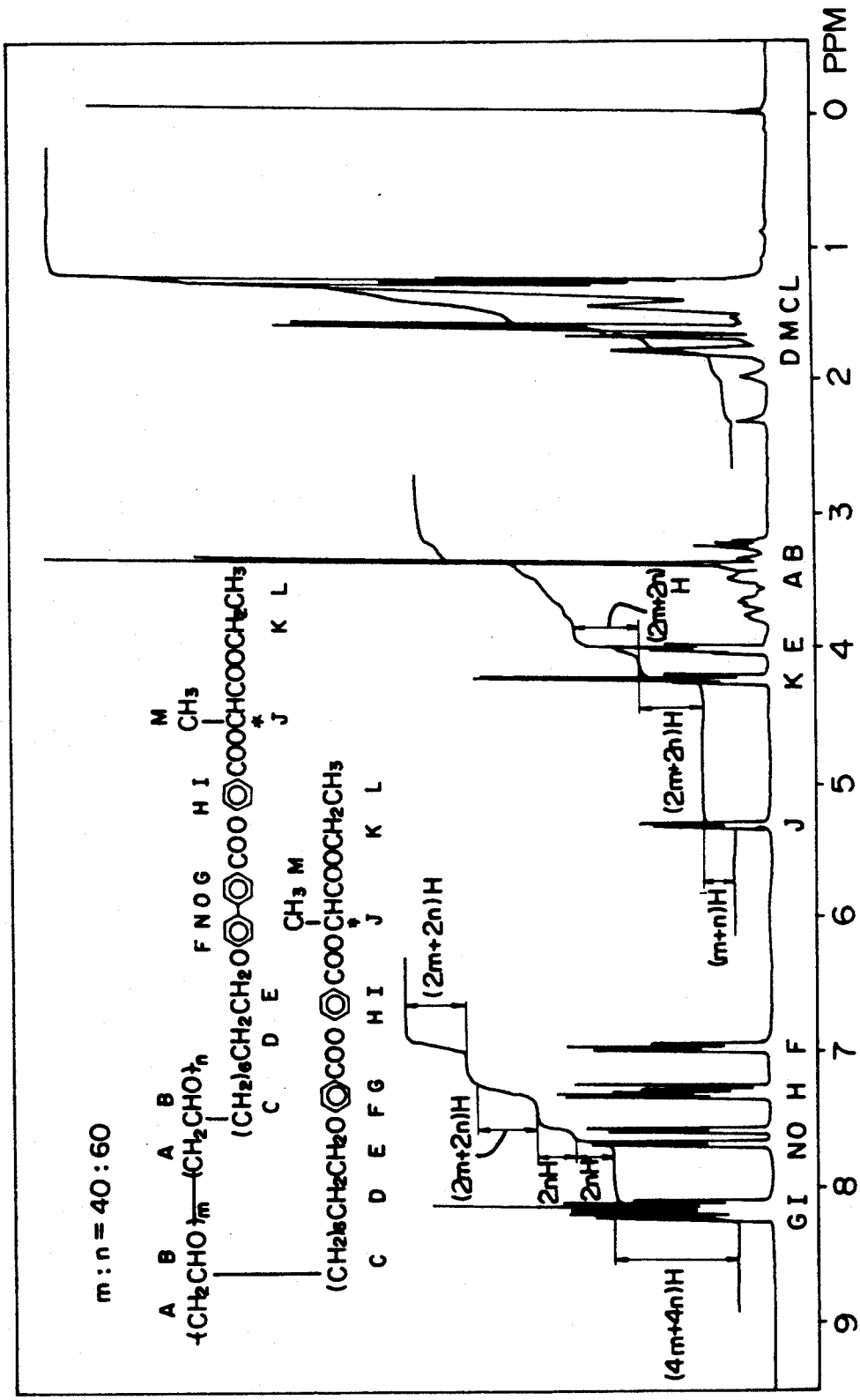
FIGS. 12 to 25 are charts showing $^1$H-NMR spectrum of the liquid-crystalline polymers obtained in Examples 14 to 27, respectively
Figure 13:
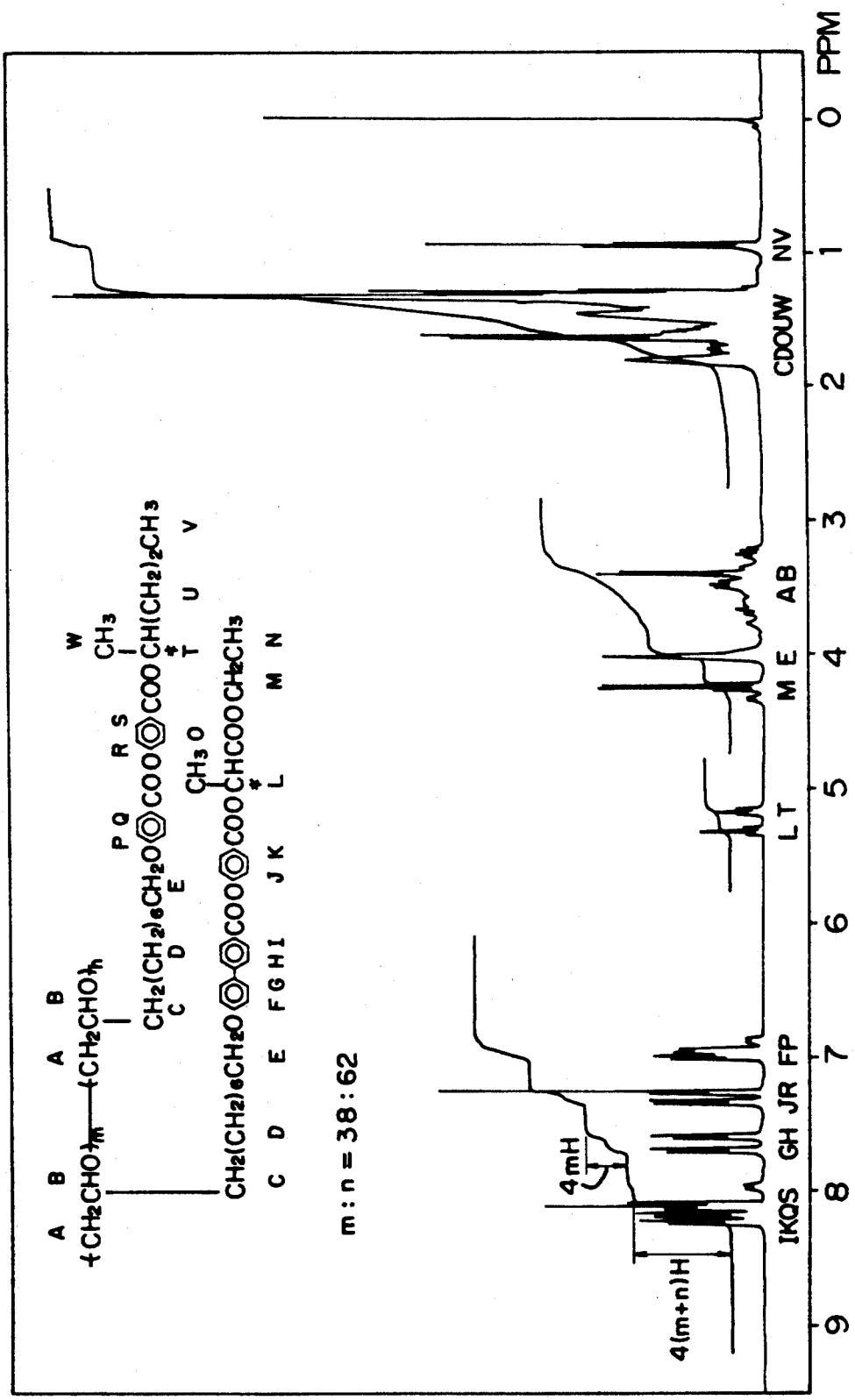
Figure 14:
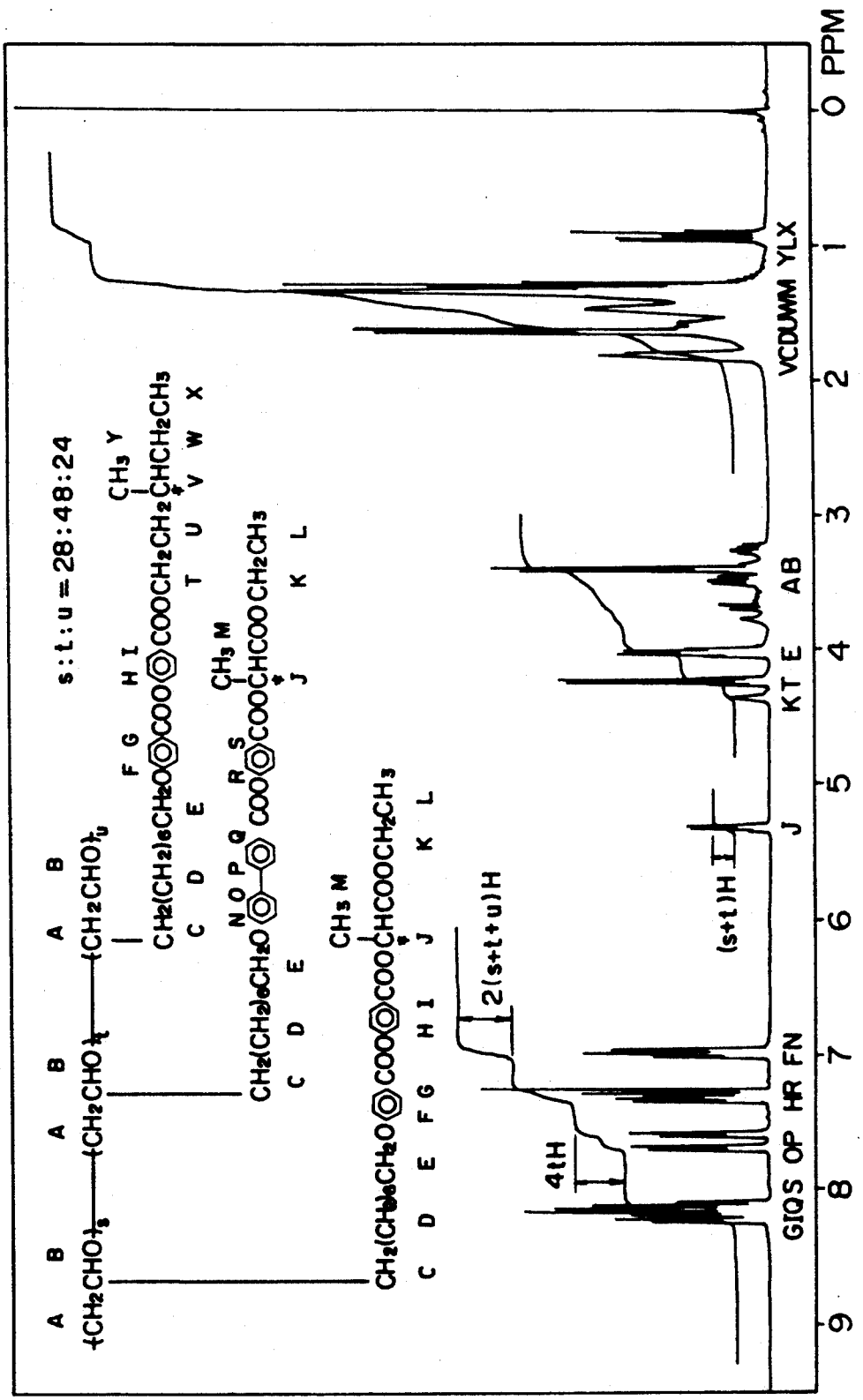
Figure 15:
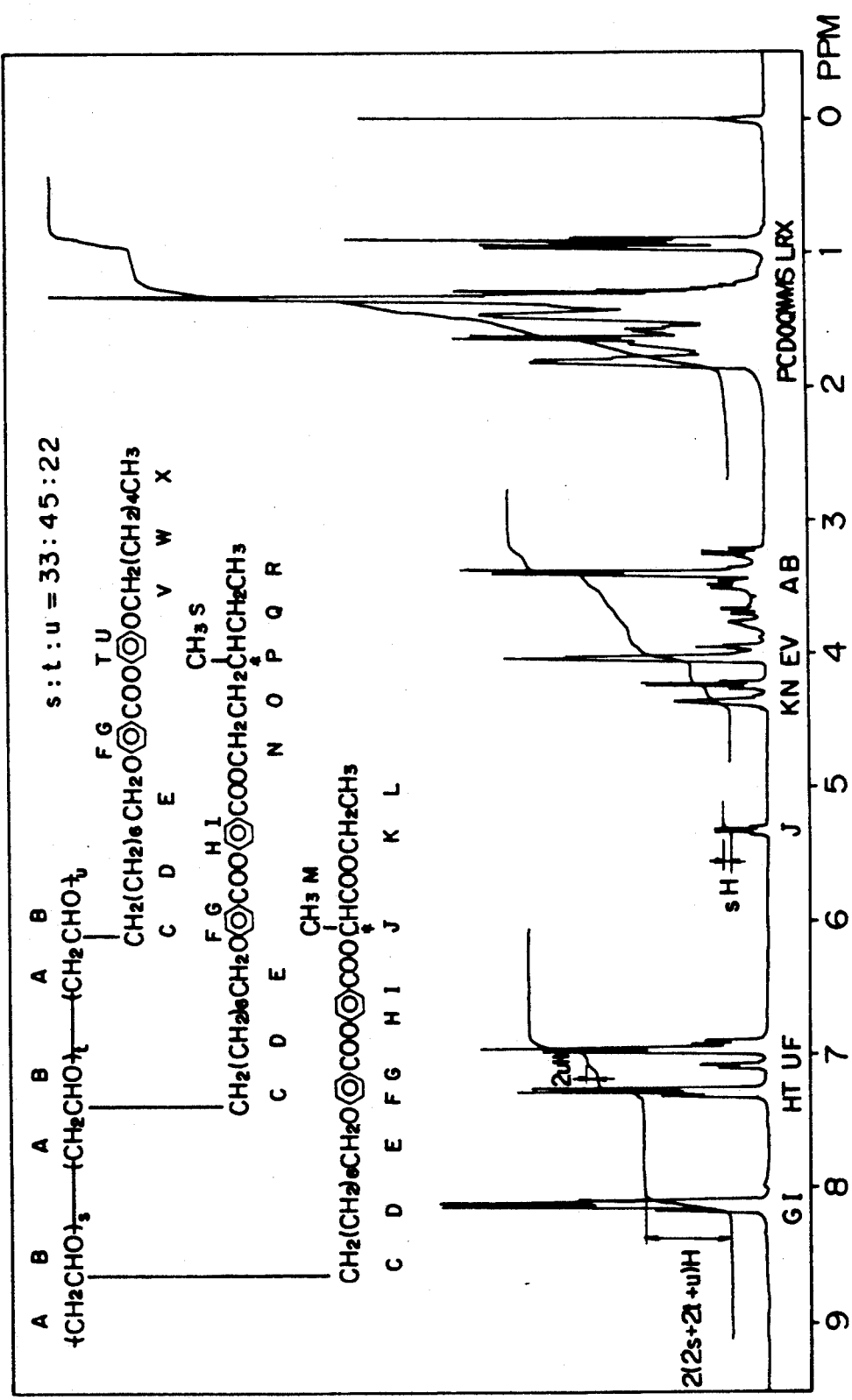
Figure 16:
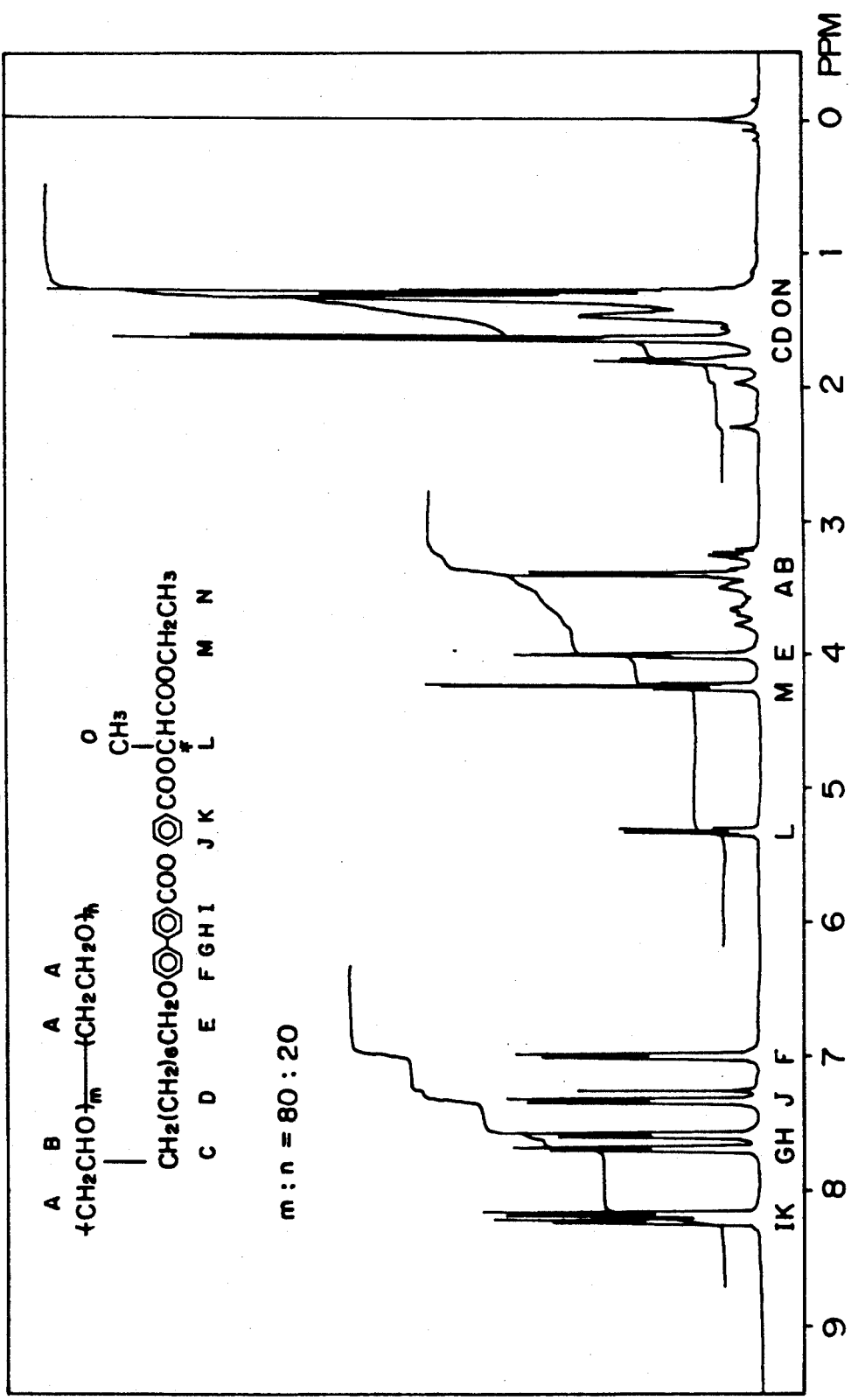
Figure 17:
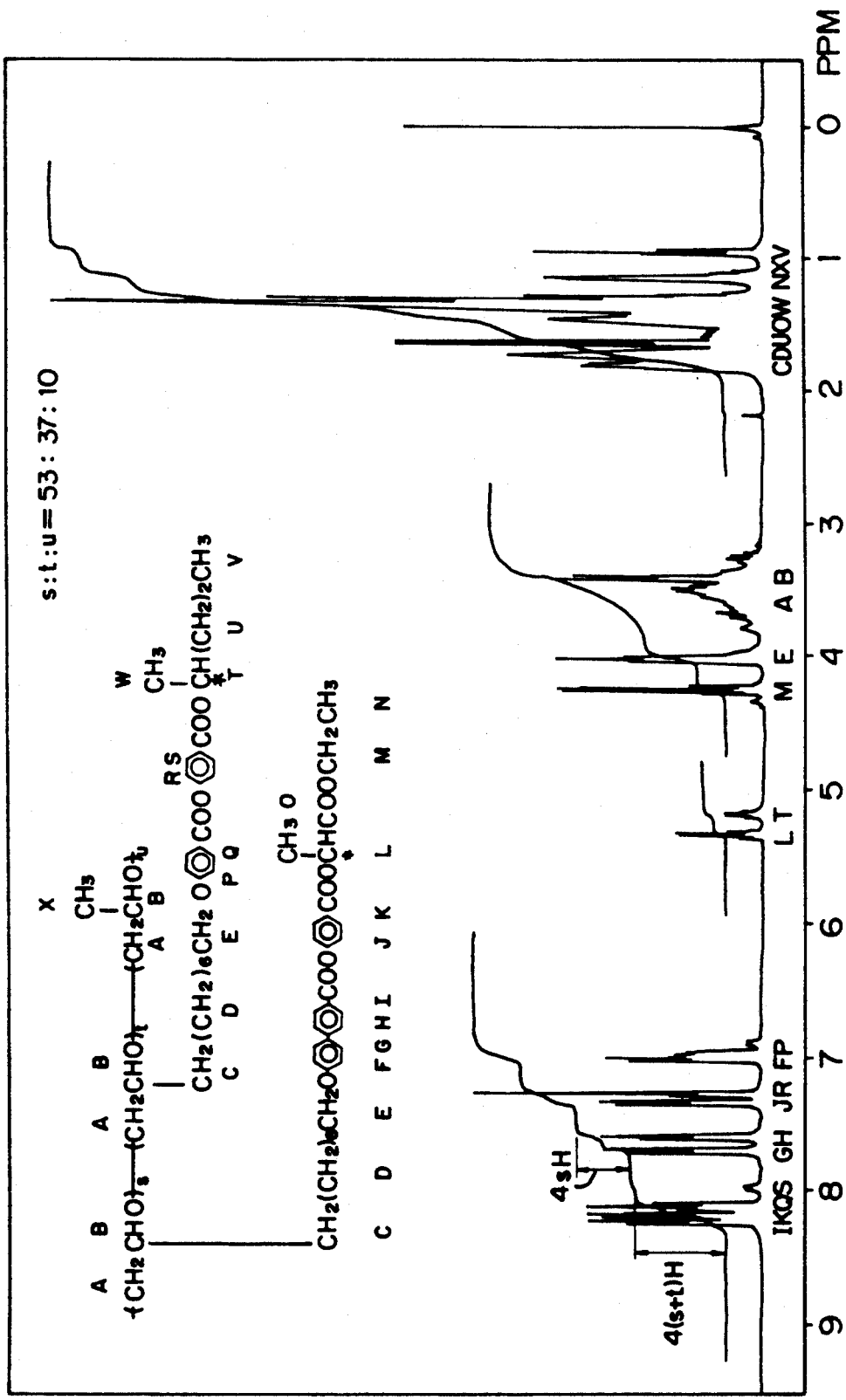
Figure 18:
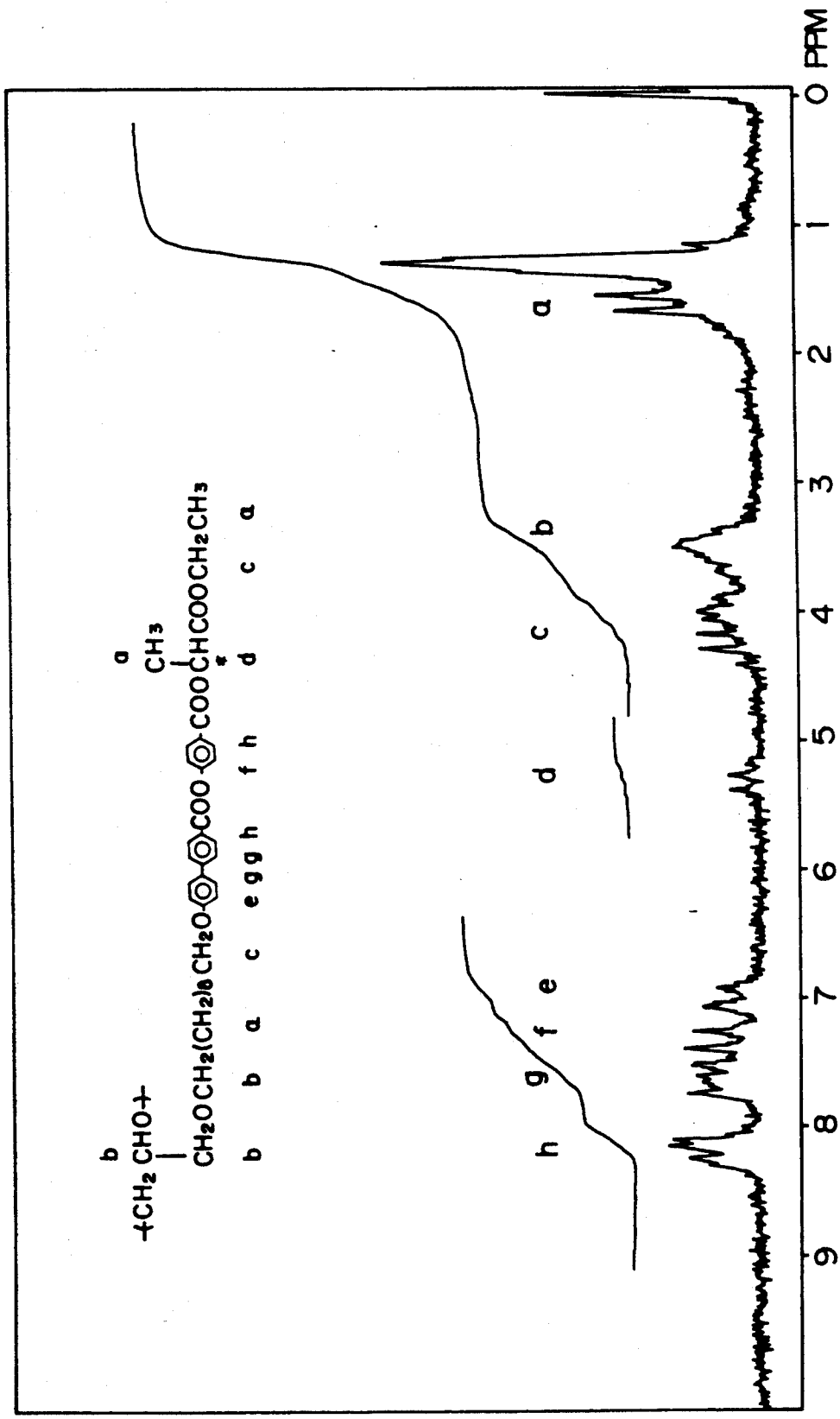
Figure 19:
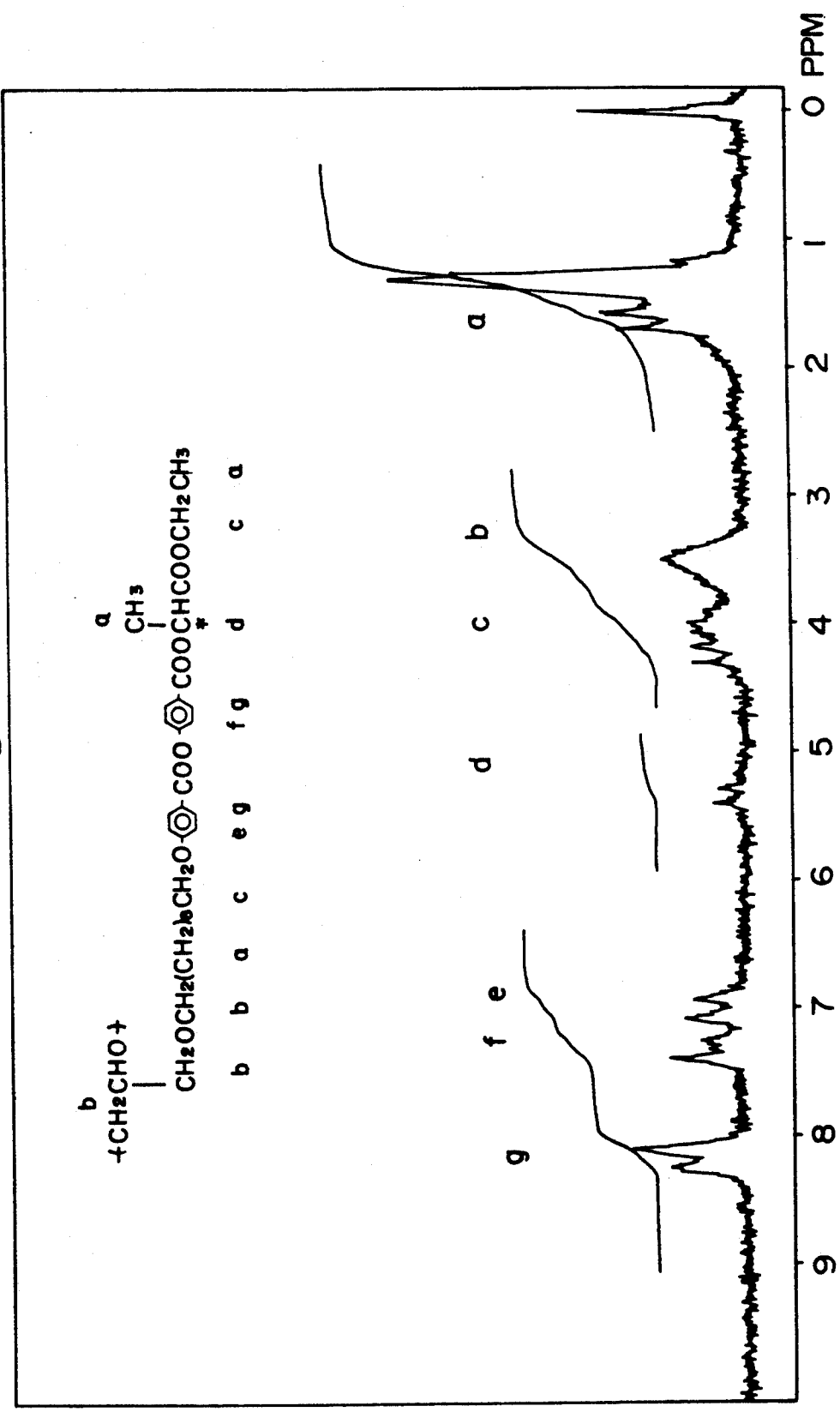
Figure 20:
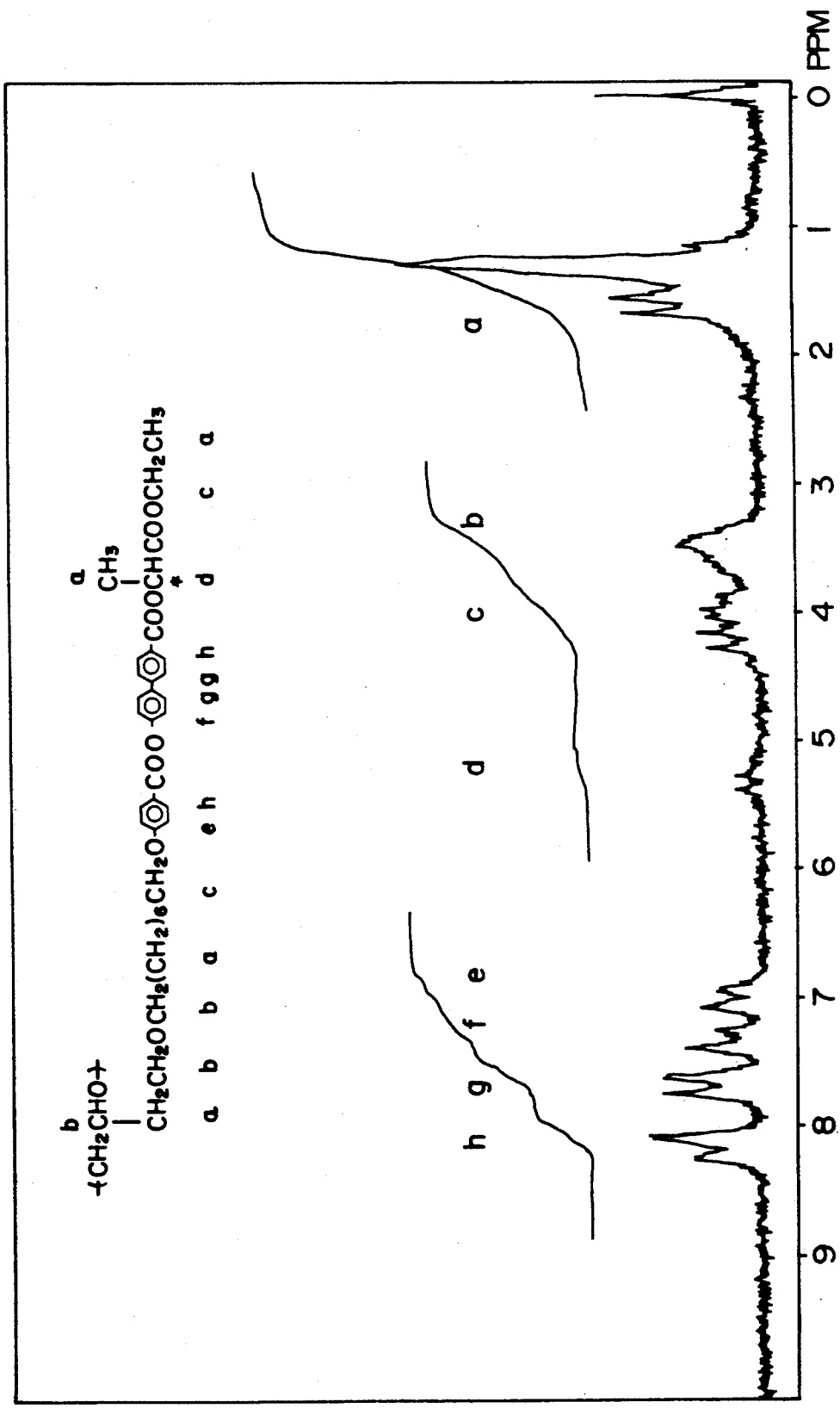
Figure 21:
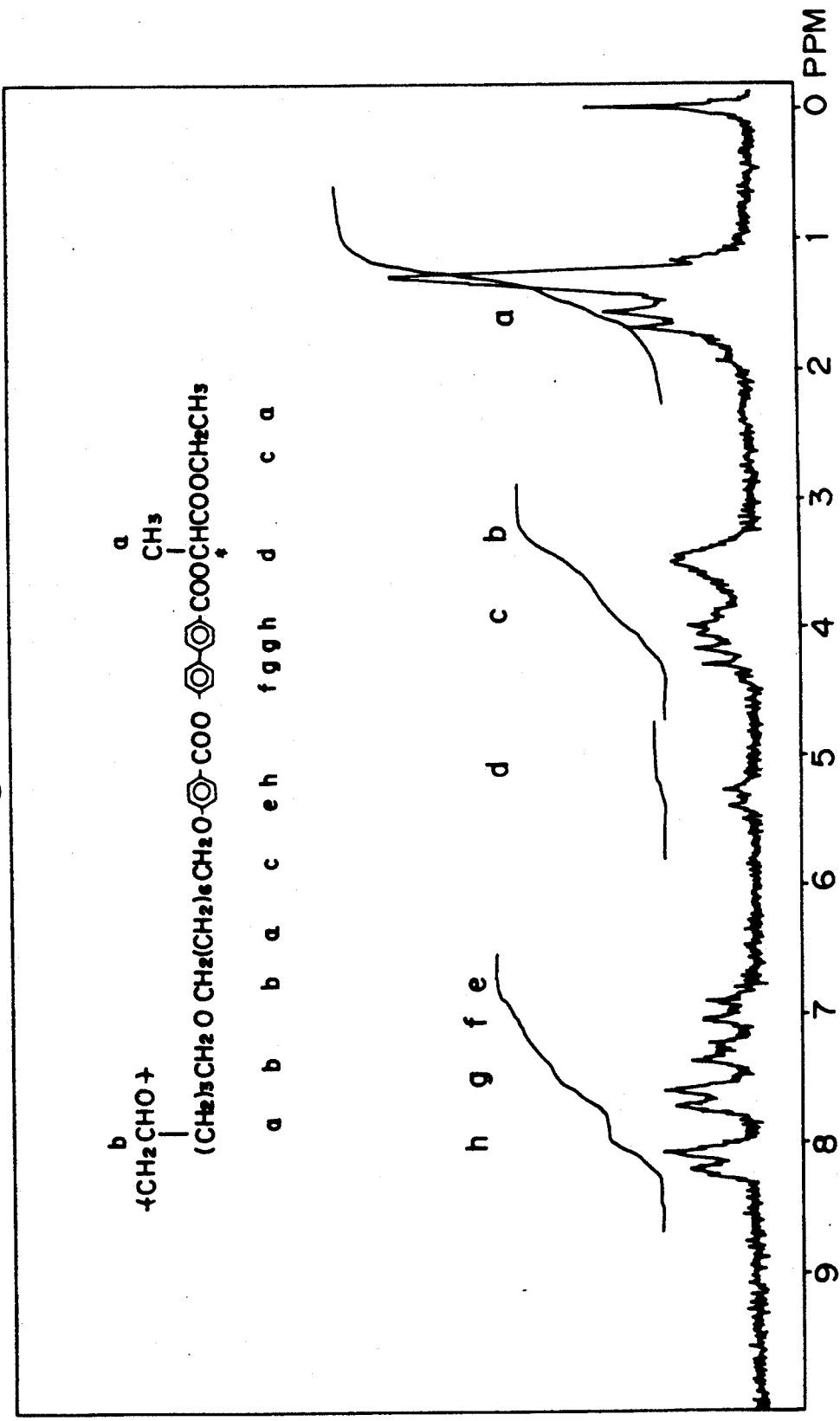
Figure 22:
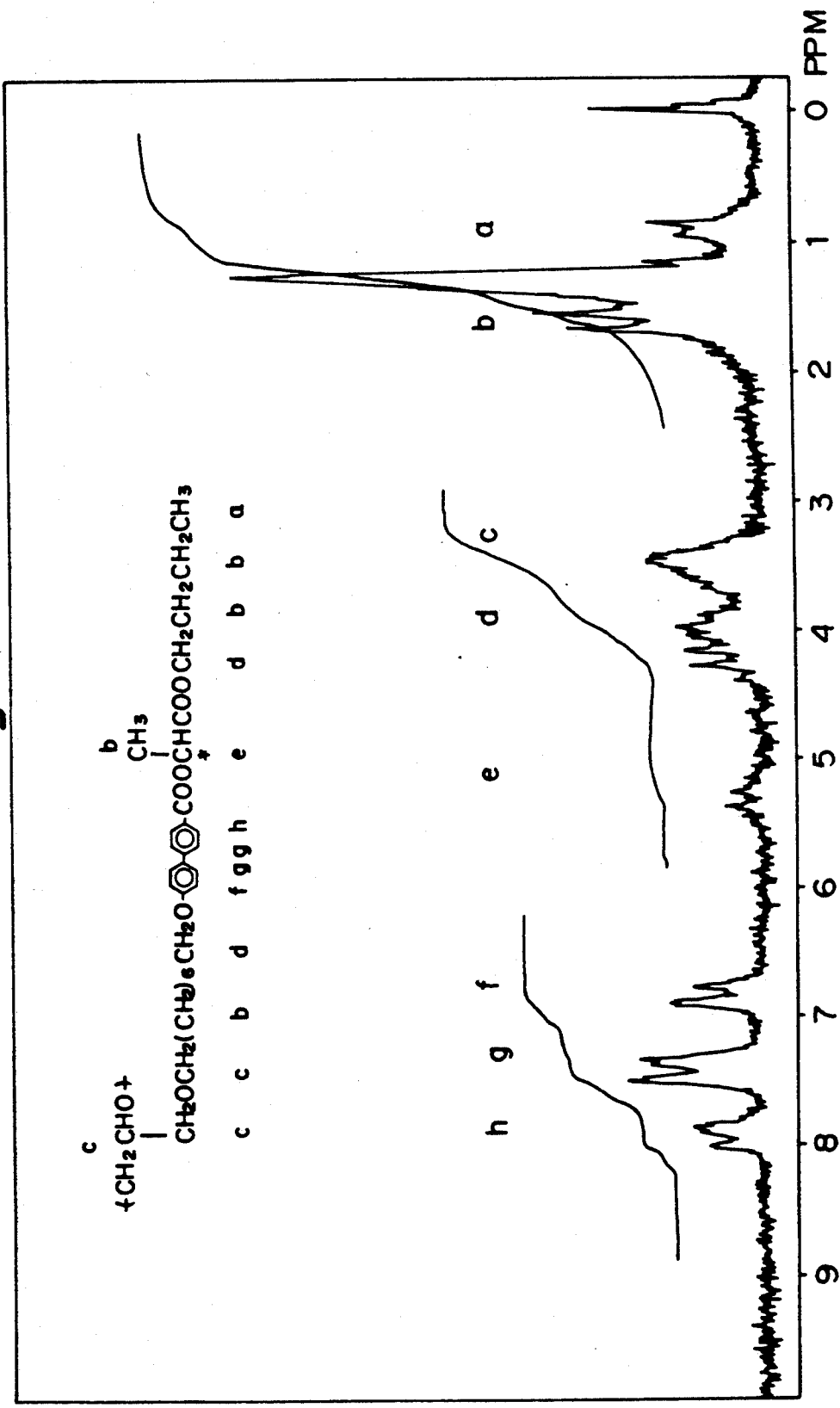
Figure 23:
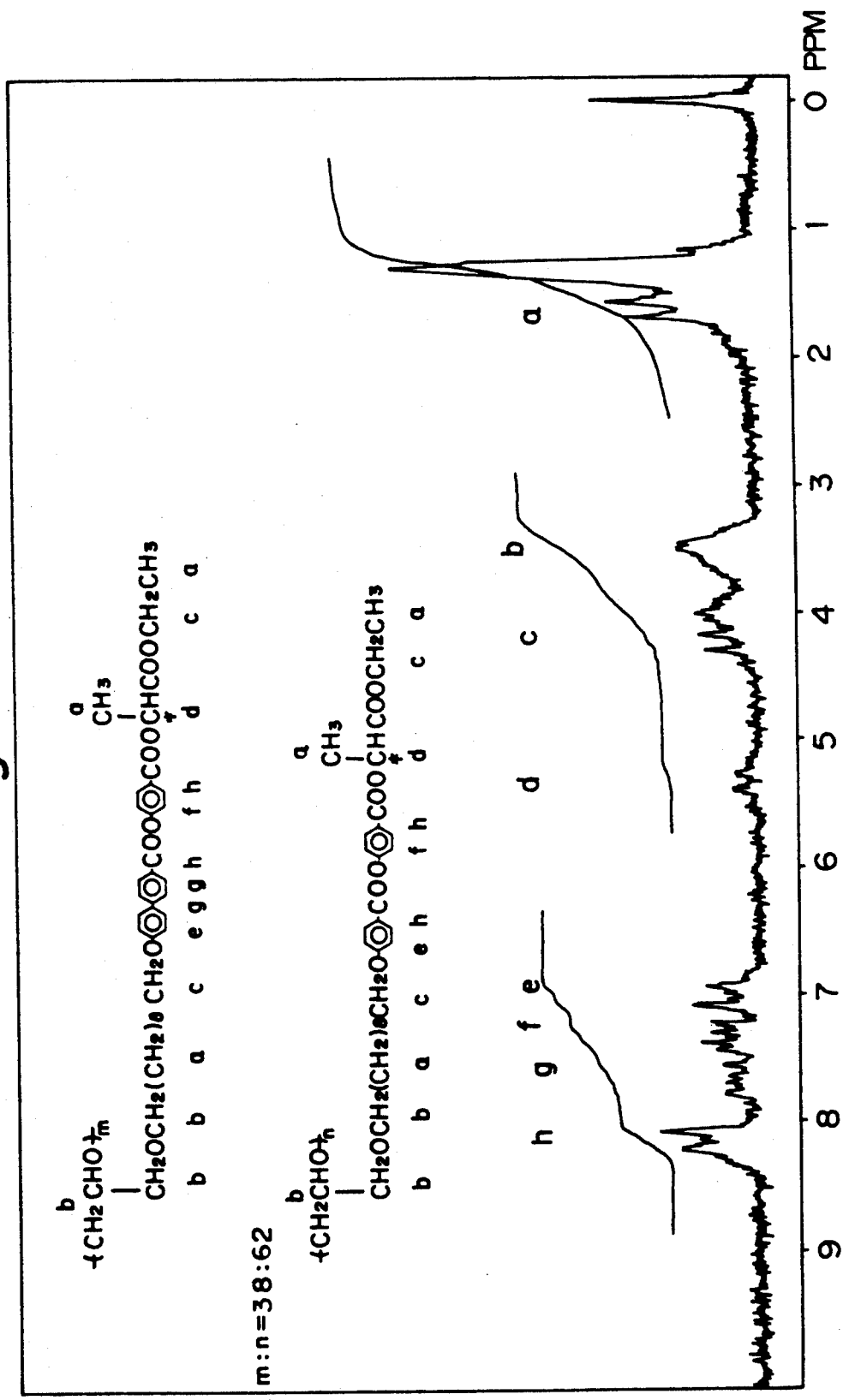
Figure 24:
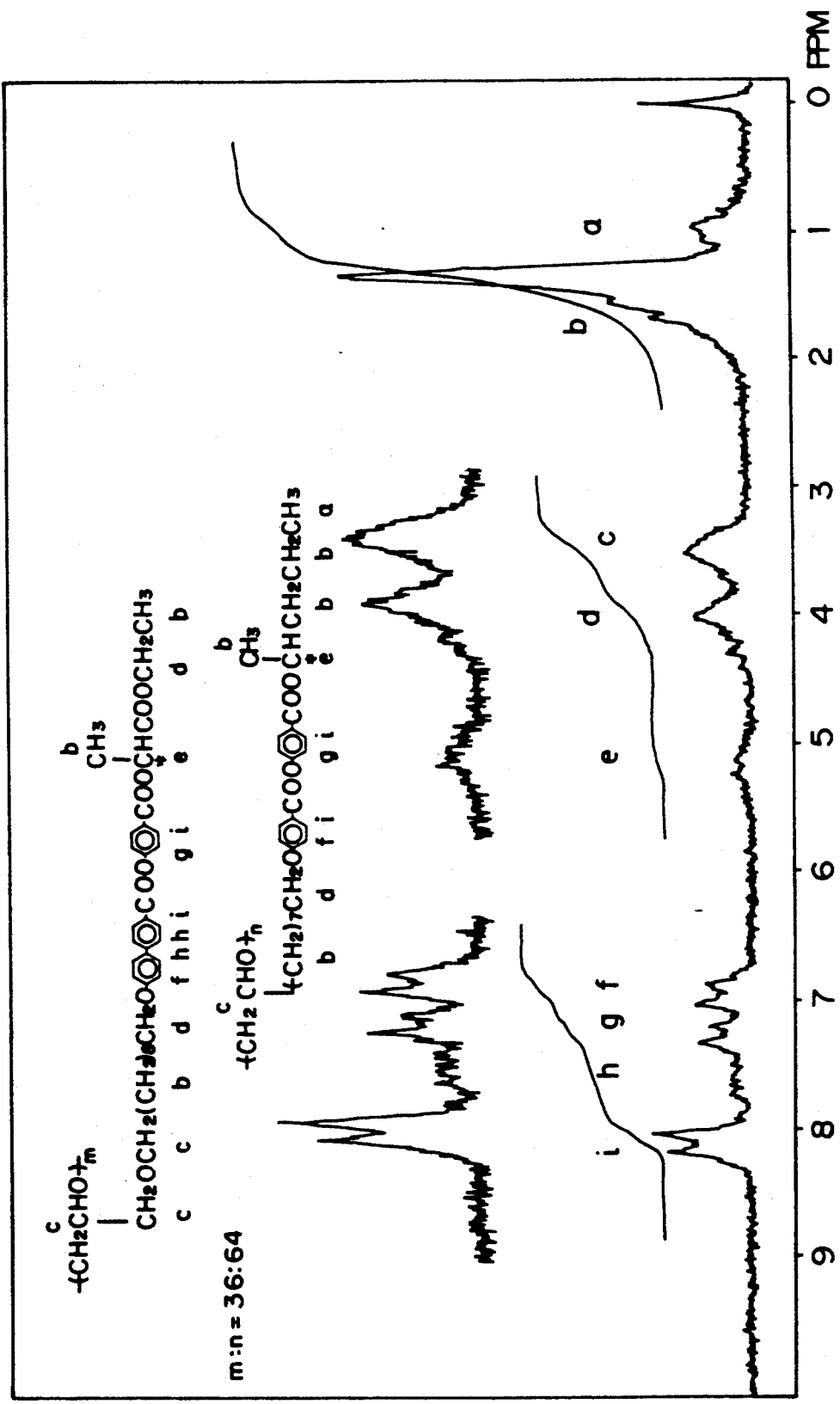
Figure 25:
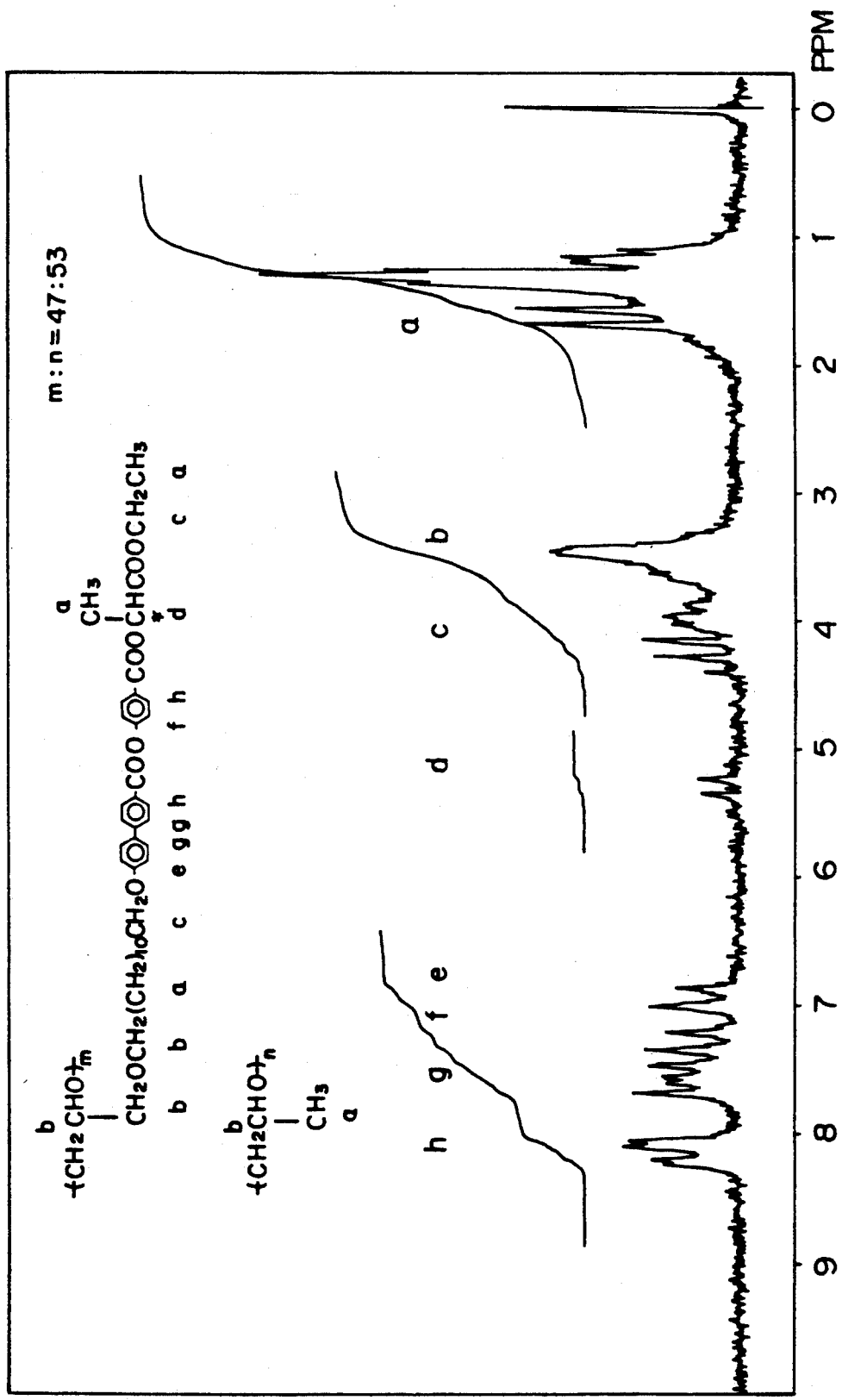

The NMR spectrum charts of the liquid-crystalline compounds and liquid-crystalline polymers obtained in Examples 1 to 3, 5 to 12, and 14 to 27 are shown in FIGS. 1 to 25, respectively.

The phase transition behaviors and electric field response time of the liquid-crystalline compounds obtained in Examples 1 to 9 are shown in Table 2, and the phase transition behaviors, the helical pitches, and the electric field response tome of the liquid-crystalline polymers obtained in Examples 10 to 27 are shown in Table 3. (g: glass state, Cry: crystal state, SmC*: chiral smectic C phase, SmA: smectic A phase, N*: chiral nematic phase, Iso: isotropic phase. The numerals in the phase transition behavior schemes represent phase transition temperatures in °C. unit.)

Measurement of response time to electric field were conducted as follows.

Measurement of response time to electric field

A liquid crystal sample was supported between two ITO substrates of 20×10 mm, and the thickness of the sample was adjusted to 25 μm by spacers. An alternative current of $E = 2 \times 10^6$ V/m was applied on the obtained liquid crystal cell, and the response time required of the light transmittance to change from 0% to 90% was measured.

Helical pitch was estimated by measuring the space between the stripes of the striped pattern which appeared on the fan texture observed in SmC* phase (measuring temperature T: a temperature lower by 10° C. than the phase transition temperature from SmA to SmC* (Tc−T=10° C.)).

EXAMPLE 1

1-ethoxycarbonylethyl 4-{4'-(9-decenyloxy)benzoyloxy}-benzoate

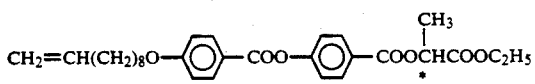

1. (1) Synthesis of 1-ethoxycarbonylethyl 4-acetoxybenzoate

A solution of 30 mmol (5.4 g) of 4-acetoxybenzoic acid and 90 mmol (10.8 g) of thionyl chloride dissolved in 50 ml of toluene was stirred for 2 hours at 80° C., and the reaction solution was then concentrated under reduced pressure, to obtain an acid chloride compound. Into a solution of 20 mmol (2.4 g) of ethyl L-lactate and 5 ml of triethylamine dissolved in 30 ml of THF (tetrahydrofuran) added dropwise was a THF solution of the above-described acid chloride compound, and the mixture was then stirred for 10 hours. After conclusion of the reaction, the reaction solution was concentrated, and was then ether extracted after addition of water. The concentrate of the resulting extract was purified by column chromatography to obtain 3.9 g of the objective acetoxy compound. (Yield: 63%)

1. (2) Synthesis of 1-ethoxycarbonylethyl 4-hydroxybenzoate

Into a solution of 12.5 mmol (3.5 g) of the acetoxy compound obtained in 1.(1) dissolved in 200 ml of ether added was 70 mmol (6.4 g) of benzylamine, and the mixture was stirred for 5 hours. After the reaction solution had been washed with water, the reaction solution was purified by column chromatography, to obtain 1.2 g of the objective hydroxy compound. (Yield: 42%)

1. (3) Synthesis of 1-ethoxycarbonylethyl 4-{4'-(9-decenyloxy)benzoyloxy}benzoate 10.0 g of 10-chloro-1-decene and 25 g of sodium iodide were allowed to react in 2-butanone for 10 hours at 80° C., to iodize 10-chloro-1-decene. After the reaction solution had been washed with water and dried, the solvent was removed from the dried reaction solution. To the residue added were 11.5 g of ethyl p-hydroxybenzoate and 9.6 g of potassium carbonate, and the mixture was refluxed in absolute ethanol for 15 hours. After addition of an aqueous potassium hydroxide solution (containing 4.0 g of potassium hydroxide), the mixture was then further heated at 80° C. for 5 hours. After conclusion of the reaction, the reaction solution was acidified with hydrochloric acid, and the acidified solution was concentrated under reduced pressure. Water was added to the residue to form a suspension, and the insoluble matter was collected and dried, to obtain 9.5 g of 4-(9-decenyloxy)benzoic acid. (Yield: 60%)

Subsequently, a solution of 6 mmol (1.7 g) of 4-(9-decenyloxy)benzoic acid and 18 mmol (2.2 g) of thionyl chloride dissolved in 30 ml of toluene was stirred at 80° C. for 3 hours, and the resulting reaction solution was concentrated under reduced pressure, to obtain an acid chloride compound. A solution of the acid chloride compound dissolved in 5 ml of THF was added dropwise into a solution of 4 mmol (1.0 g) of the hydroxy compound obtained in 1.(2) and 1 ml of triethylamine, and the mixture was then stirred at room temperature for 10 hours. After concentration of the reaction solution, water was added to the concentrate, and the mixture was then extracted with ether. After the extract had been dried and concentrated, the residue was purified by column chromatography, to obtain 1.85 g of the objective liquid-crystalline compound. (Yield: 93%)

EXAMPLE 2

1-ethoxycarbonylethyl 4-[4'-{4''-(9-decenyloxy)phenyl}-benzoyloxy]benzoate

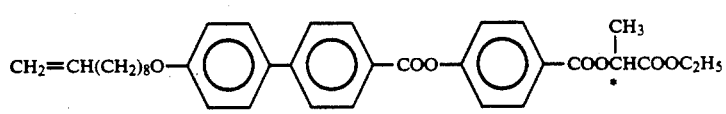

2.(1) Synthesis of 4-{4'-(9-decenyloxy)phenyl}benzonitrile

A suspension of 20 mmol (5.4 g) of 10-iodo-1-decene, 20 mmol (3.9 g) of 4-(4'-hydroxyphenyl)-benzonitrile, and 80 mmol (11 g) of potassium carbonate anhydride in 100 ml of 2-butanone was refluxed for 20 hours with stirring. After filtration and concentration of the reaction solution, the residue was purified by column chromatography, to obtain 4.0 g of the objective nitrile compound. (Yield: 60%)

2.(2) Synthesis of 4-{4'-(9-decenyloxy)phenyl}benzoic acid

A mixture of 10 mmol (3.3 g) of the nitrile compound obtained in 2.(1), 40 mmol (1.3 g) of potassium hydroxide, 10 ml of ethanol, and 2 ml of water was refluxed for 5 hours with stirring, and diluted hydrochloric acid was then added to the mixture to form an acid solution. After water had been added to the acid solution, the resulting mixture was extracted with methylene chloride. The extract was dried and concentrated, to obtain 3.2 g of the objective carboxylic acid compound. (Yield: 91%)

2.(3) Synthesis of 1-ethoxycarbonylethyl 4-[4'-{4''-(9-decenyloxy)phenyl}benzoyloxy]benzoate A solution of 8 mmol (2.8 g) of the carboxylic acid compound obtained in 2.(2) and 24 mmol (2.9 g) of thionyl chloride dissolved in 30 ml of toluene was stirred for 2 hours at 80° C., and the reaction solution was then concentrated under reduced pressure, to obtain an acid chloride compound. A solution of the acid chloride compound dissolved in 3 ml of THF was added dropwise into a solution of 4 mmol (0.95 g) of the hydroxy compound obtained in 1.(2) of Example 1 and 1 ml of triethylamine dissolved in 10 ml of THF, and the mixture was then stirred for 10 hours. After concentration of the reaction solution, water was added to the concentrate, and the mixture was then extracted with ether. After concentration of the extract, the concentrate was purified by column chromatography, to obtain 1.3 g of the objective liquid-crystalline compound. (Yield: 58%)

EXAMPLE 3

1-ethoxycarbonylethyl 4-{4'-(9-decenyloxy)phenyl}benzoate

3.(1) Synthesis of 1-ethoxycarbonylethyl 4-{4'-(9-decenyloxy)phenyl}benzoate

A solution of 8 mmol (2.8 g) of the carboxylic acid compound obtained in 2.(2) of Example 2 and 24 mmol (2.9 g) of thionyl chloride dissolved in 30 ml of toluene was stirred at 80° C. for 2 hours, and the reaction solution was then concentrated under reduced pressure, to obtain an acid chloride compound. A solution of the acid chloride compound dissolved in 3 ml of THF was added dropwise into a solution of 8 mmol (0.94 g) of ethyl L-lactate and 1 ml of triethylamine dissolved in 10 ml of THF, and the mixture was then stirred for 10 hours. After concentration of the reaction solution, water was added to the concentrate, and the mixture was then extracted with ether. After concentration of the extract, the concentrate was purified by column chromatography, to obtain 2.2 g of the objective liquid-crystalline compound. (Yield: 61%)

EXAMPLE 4

1-butoxycarbonylethyl 4-[4'-{4''-(13-tetradecenyloxy)-benzoyloxy}phenyl]benzoate

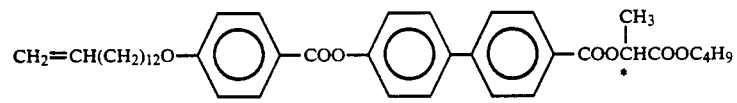

4.(1) Synthesis of 1-butoxycarbonylethyl 4-(4'-acetoxyphenyl)benzoate

A solution of 25 mmol (6.4 g) of 4-(4'-acetoxyphenyl)-benzoic acid obtained by acetylating 4-(4'-hydroxyphenyl)benzoic acid and 75 mmol (9 g) of thionyl chloride dissolved in 50 ml of toluene was stirred at 80° C. for 2 hours, and the reaction solution was then concentrated under reduced pressure, to obtain an acid chloride compound. A THF solution of the acid chloride compound was added dropwise into a solution of 20 mmol (2.9 g) of butyl L-lactate and 5 ml of triethylamine dissolved in 30 ml of THF, and the mixture was then stirred for 10 hours. After concentration of the reaction solution, water was added to the concentrate, and the mixture was then extracted with ether. Concentrate of the extract was purified by column chromatography, to obtain 5.8 g of the objective acetoxy compound. (Yield: 76%)

4.(2) Synthesis of 1-butoxycarbonylethyl 4-(4'-hydroxyphenyl)benzoate

Into a solution of 14.0 mmol (5.4 g) of the acetoxy compound obtained in 4.(1) dissolved in 200 ml of ether added was 80 mmol (7.3 g) of benzylamine, and the mixture was then stirred for 5 hours. The reaction solution was washed with water and was then purified by column chromatography, to obtain 3.4 g of the objective hydroxy compound. (Yield: 71%)

4.(3) Synthesis of 1-butoxycarbonylethyl 4-[4'-{4''-(13-tetradecenyloxy)benzoyloxy}phenyl]benzoate 4-(13-tetradecenyloxy)benzoic acid was synthesized in the same manner as in the synthesis of 4-(9-decenyloxy)benzoic acid in 1.(3) of Example 1. Then, a solution of 6 mmol (2.0 g) of the obtained 4-(13-tetradecenyloxy)benzoic acid and 18 mmol (2.2 g) of thionyl chloride dissolved in 30 ml of toluene was stirred at 80° C. for 3 hours, and the resulting reaction solution was concentrated under reduced pressure, to obtain an acid chloride compound. Subsequently, a solution of the acid chloride compound dissolved in 5 ml of THF was added dropwise into a solution of 4 mmol (1.4 g) of the hydroxy compound obtained in 4.(2) and 1 ml of triethylamine dissolved in 10 ml of THF. The mixture was then stirred at room temperature for 10 hours. After concentration of the reaction solution, water was added to the concentrate, and the mixture was then extracted with ether. After the extract had been dried and concentrated, the concentrate was purified by column chromatography, to obtain 2.0 g of the objective liquid-crystalline compound. (Yield: 76%)

EXAMPLE 5

1-ethyloxycarbonylethyl 4-[4'-{4''-(10-allyloxydecyloxy)phenyl}benzoyloxy]-benzoate

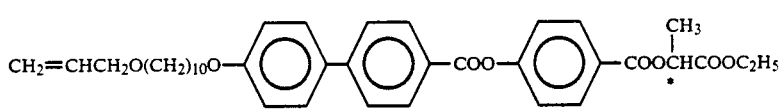

5.(1) Synthesis of 10-iododecyl allyl ether 52 mmol (3.0 g) of allyl alcohol was dissolved in 50 of THF. Into the solution added gradually was 2.3 g of 60% sodium hydride. After the mixture had been stirred for 10 minutes at room temperature, a solution consisting of 127 mmol (50.0 g) of 1,10-diiododecane and 100 ml of THF was added into the mixture dropwise. After conclusion of dropping, the resulting mixture was refluxed for 12 hours. A small amount of water was then added to the reaction solution, to decompose the residual sodium hydride. After THF had been distilled out under reduced pressure, water and dichloromethane were added to the residue, and the mixture was then shaken. The dichloromethane layer was collected and was dried over magnesium sulfate. The dried dichloromethane layer was concentrated under reduced pressure, and the residue was purified by column chromatography, to obtain 13.1 g of the objective ω-haloalkyl allyl ether. (Yield: 78%)

5.(2) Synthesis of 4'-(10-allyloxydecyloxy)biphenyl-4-carboxylic acid 25 mmol (8.2 g) of 10-iododecyloxy allyl ether obtained in 5.(1), 22 mmol (4.8 g) of 4'-hydroxybiphenyl-4- carboxylic acid, 50 mmol (3.3 g) of potassium hydroxide, and 5.0 g of water were allowed to react by refluxing them in 50 ml of methanol for 24 hours. 500 ml of water was added to the resulting reaction solution, and the pH value of the resulting mixture was adjusted to 2 by adding hydrochloric acid dropwise. The precipitate was collected and was dried under reduced pressure. The obtained crude product was recrystallized from 15 acetic acid, to obtain 4.3 g of the objective carboxylic acid compound. (Yield: 53%)

5.(3) Synthesis of 1-ethoxycarbonylethyl 4-acetoxybenzoate

A solution of 30 mmol (5.4 g) of 4-acetoxybenzoic acid and 90 mmol (10.8 g) of thionyl chloride dissolved in 50 ml of toluene was stirred for 2 hours at 80° C. The resulting reaction solution was concentrated under reduced pressure, to obtain an acid chloride compound. A THF solution of the acid chloride compound was added dropwise into a solution of 20 mmol (2.4 g) of ethyl L-lactate and 5 ml of triethylamine dissolved in 30 ml of THF, and the mixture was then stirred for 10 hours. After concentration of the reaction solution, water was added to the concentrate, and the mixture was then extracted with ether. Concentrate of the extract was purified by column chromatography, to obtain 3.9 g of the objective acetoxy compound. (Yield: 63%)

5.(4) Synthesis of 1-ethoxycarbonylethyl 4-hydroxybenzoate

Into a solution of 12.5 mmol (3.5 g) of the acetoxy compound obtained in 5.(3) dissolved in 200 ml of ether added was 70 mmol (6.4 g) of benzylamine, and the mixture was then stirred for 5 hours. After the reaction solution had been washed with water, the resulting solution was purified by column chromatography, to obtain 1.2 g of the objective hydroxy compound. (Yield: 42%)

5.(5) Synthesis of 1-ethoxycarbonylethyl 4-[4'-{4''-(10-allyloxydecyloxy)phenyl}benzoyoxy]benzoate A solution of 8 mmol (3.3 g) of the carboxylic acid compound obtained in 5.(2) and 24 mmol (2.9 g) of thionyl chloride dissolved in 30 ml of toluene was stirred for 2 hours at 80° C., and the resulting reaction solution was concentrated under reduced pressure, to obtain an acid chloride compound. A solution of the acid chloride compound dissolved in 3 ml of THF was added dropwise into a solution of 4 mmol (0.95 g) of the hydroxy compound obtained in 5.(4) and 1 ml of triethylamine dissolved in 10 ml of THF, and the mixture was then stirred for 10 hours. After concentration of the reaction solution, water was added to the concentrate, and the mixture was then extracted with ether. After the extract had been concentrated, the concentrate was purified by column chromatography, to obtain 2.0 g of the objective liquid-crystalline compound. (Yield: 79%)

EXAMPLE 6

1-ethoxycarbonylethyl 4-{4'-(10-allyloxydecyloxy)-benzoyloxy}benzoate

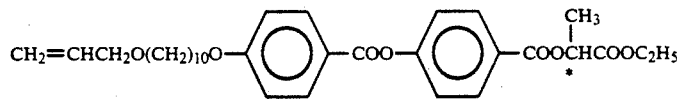

6.(1) Synthesis of 1-ethoxycarbonylethyl 4-{4'-(10-allyloxydecyloxy)benzoyloxy}benzoate 70 mmol (22.7 g) of 10-iododecyl allyl ether, 70 mmol (10.6 g) of methyl p-hydroxybenzoate, and 70 mmol (9.6 g) of potassium carbonate were refluxed in absolute ethanol for 15 hours. After addition of an aqueous potassium hydroxide solution (containing 4.0 g of potassium hydroxide) into the reaction solution, the resulting mixture was further heated at 80° C. for 5 hours. After conclusion of the reaction, the reaction solution was acidified with hydrochloric acid, and the acidified reaction solution was then concentrated under reduced pressure. Water was added to the residue to form a suspension, and the insoluble matter was collected and was then dried, to obtain 18.7 g of 4-(10-allyloxydecyloxy)benzoic acid. (Yield: 80%)

Subsequently, a solution of 10 mmol (3.3 g) of 4-(10-allyloxydecyloxy)benzoic acid and 18 mmol (2.2 g) of thionyl chloride dissolved in 30 ml of toluene was stirred for 3 hours at 80° C., and the resulting reaction solution was concentrated under reduced pressure, to obtain an acid chloride compound. A solution of the acid chloride compound dissolved in 5 ml of THF was added dropwise into a solution of 8 mmol (2.0 g) of 1-ethoxycarbonylethyl 4-hydroxybenzoate and 1 ml of triethylamine dissolved in 10 ml of THF, and the mixture was then stirred for 10 hours at room temperature. After concentration of the reaction solution, water was added to the concentrate, and the mixture was then extracted with ether. After the extract has been dried and concentrated, the concentrate was purified by column chromatography, to obtain 3.2 g of the objective liquid-crystalline compound. (Yield: 73%)

EXAMPLE 7

1-ethoxycarbonylethyl 4'-[4''-{8-(3-butenyloxy)octyloxy}-benzolyloxy]biphenyl-4-carboxylate

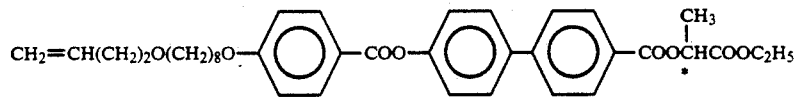

7.(1) Synthesis of 3-butenyl 8-bromooctyl ether 8.4 g of the objective ω-haloalkyl alkenyl ether was prepared in the same manner as in 5.(1) of Example 5, with the proviso 42 mmol (3.0 g) of 3-butene-1-ol, 100 mmol (27.2 g) of 1,8-dibromooctane, and 1.7 g of 60% sodium hydride were used. (Yield: 76%)

7.(2) Synthesis of 4-{8-(3-butenyloxy)octyloxy}benzoic acid 8.1 g of the objective derivative of benzoic acid was prepared in the same manner as in 6(1) of Example 6, with the proviso 30 mmol (7.9 g) of the ether compound obtained in 7.(1), 30 mmol (4.6 g) of methyl 4-hydroxybenzoate, and 30 mmol (4.2 g) of potassium carbonate were used. (Yield: 84%)

7.(3) Synthesis of 1-ethoxycarbonyl 4'-hydroxybiphenyl-4-carboxylate 3.2 g of the objective hydroxy compound was prepared in the same manner as in 5.(3) and 5.(4) of Example 5, with the proviso 30 mmol (7.7) of 4'-hydroxybiphenyl-4-carboxylic acid, 20 mmol (5.4 g) of ethyl L-lactate, and 70 mmol (6.4 g) of benzylamine were used. (Yield: 51%)

7.(4) Synthesis of 1-ethoxycarbonylethyl 4'-[4''-{8-(3-butenyloxy)octyloxy}benzoyloxy]biphenyl-4-carboxylate 30 mmol of thionyl chloride was added into 10 mmol (3.2 g) of the derivative of benzoic acid obtained in 7.(2), and the mixture was then stirred for 2 hours at 80° C. The reaction solution was then concentrated under reduced pressure to obtain an acid chloride compound. Subsequently, a solution of the acid chloride compound dissolved in 5 ml of THF was added dropwise into a solution of 8 mmol (2.5 g) of the hydroxy compound obtained in 7.(3) and 1 ml of triethylamine dissolved in 10 ml of THF, and the mixture was then stirred for one day at room temperature. After concentration of the reaction solution, the concentrate was purified by column chromatography, to obtain 3.5 g of the objective liquid-crystalline compound. (Yield: 71%)

EXAMPLE 8

1-ethoxycarbonylethyl 4'-[4''-{8-(5-hexenyloxy)octyloxy}-benzoyloxy]biphenyl-4-carboxylate

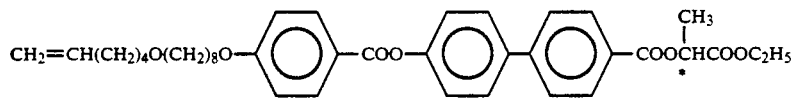

8.(1) Synthesis of 5-hexenyl 8-bromooctyl ether 6.5 g of the objective ω-haloalkyl alkenyl ether was prepared in the same manner as in 5.(1) of Example 5, with the proviso 30 mmol (3.0 g) of 5-hexene-1-ol, 80 mmol of 1,8-dibromooctane, and 1.2 g of 60% sodium hydride were used. (Yield: 75%)

8.(2) Synthesis of 4-{8-(5-hexenyloxy)octyloxy}benzoic acid 5.6 g of the objective derivative of benzoic acid was prepared in the same manner as in 6.(1) of Example 6, with the proviso 20 mmol (5.8 g) of the ether compound obtained in 8.(1), 20 mmol (3.0 g) of methyl 4-hydroxybenzoate, and 20 mmol (2.8 g) of potassium carbonate were used. (Yield: 80%)

8.(3) Synthesis of 1-ethoxycarbonylethyl 4'-[4''-{8-(5-hexenyloxy)octyloxy}benzoyloxy]biphenyl-4-carboxylate 30 ml of thionyl chloride was added into 10 mmol (3.5 g) of the derivative of benzoic acid obtained in 8.(2), and the mixture was then stirred for 2 hours at 80° C. The reaction solution was concentrated under reduced pressure, to obtain an acid chloride compound. Subsequently, a solution of the acid chloride compound dissolved in 5 ml of THF was added dropwise into a solution of 8 mmol (2.5 g) of the hydroxy compound obtained in 7.(3) of Example 7 and 1 ml of triethylamine dissolved in 10 ml of THF, and the mixture was then stirred for one day at room temperature. After concentration of the resulting reaction solution, the concentrate was purified by column chromatography, to obtain 4.1 g of the objective liquid-crystalline compound. (Yield: 79%)

EXAMPLE 9

1-butoxycarbonylethyl 4-{4'-(8-allyloxyoctyloxy)phenyl}-benzoate

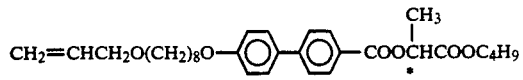

9.(1) Synthesis of 8-bromooctyl allyl ether 8.3 g of the objective ω-haloalkyl allyl ether was prepared in the same manner as in 5.(1) of Example 5, with the proviso 52 mmol (3.0 g) of allyl alcohol, 2.3 g of 60% sodium hydride, and 110 mmol (30.0 g) of 1,8-dibromooctane were used. (Yield: 64%)

9.(2) Synthesis of 4'-(8-allyloxyoctyloxy)biphenyl-4-carboxylic acid 5.5 g of the objective carboxylic acid compound was prepared in the same manner as in 5.(2) of Example 5, with the proviso 25 mmol (6.2 g) of the allyl ether compound obtained in 9.(1), 22 mmol (4.8 g) of 4'-hydroxybiphenyl-4-carboxylic acid, and 60 mmol (3.4 g) of potassium hydroxide were used. (Yield: 66%)

9.(3) Synthesis of 1-butoxycarbonylethyl 4-{4'-(8-allyloxyoctyloxy)phenyl{benzoate 8 mmol (3.1 g) of the carboxylic acid compound obtained in 9.(2) and 20 ml of thionyl chloride were stirred for 3 hours at 80° C., and the reaction solution was then concentrated under reduced pressure, to obtain an acid chloride compound. A THF solution of the acid chloride compound was added dropwise into a solution of 10 mmol (1.5 g) of butyl L-lactate and 3 ml of triethylamine dissolved in 30 ml of THF, and the mixture was then stirred for 8 hours. After concentration of the reaction solution, water was added to the concentrate, and the mixture was then extracted with ethyl acetate. After concentration of the extract, the concentrate was purified by column chromatography, to obtain 2.9 g of the objective liquid-crystalline compound. (Yield: 72%)

The values obtained by the elementary analysis of the liquid-crystalline compounds obtained in Examples 1 to 9 are shown in Table 1.

TABLE 1

| Example No. | C Calculated value (%) | C Experimental value (%) | H Calculated value (%) | H Experimental value (%) |
|---|---|---|---|---|
| 1 | 70.14 | 70.12 | 7.31 | 7.39 |
| 2 | 73.40 | 73.25 | 7.04 | 7.26 |
| 3 | 74.31 | 74.15 | 8.02 | 8.23 |
| 4 | 74.97 | 74.86 | 7.98 | 8.11 |
| 5 | 72.36 | 72.33 | 7.35 | 7.38 |
| 6 | 69.29 | 69.30 | 7.63 | 7.62 |
| 7 | 72.06 | 72.01 | 7.19 | 7.17 |
| 8 | 72.65 | 72.55 | 7.50 | 7.55 |
| 9 | 72.91 | 72.86 | 8.29 | 8.27 |

EXAMPLE 10 poly[1-ethoxycarbonylethyl
4-{4'-(9,10-epoxdecyloxy)-benzoyloxy}benzoate]

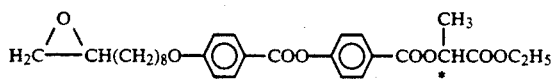

10.(1) Epoxidation

After the atmosphere of reaction apparatus had been replaced with argon, a solution of 1.0 mmol (500 mg) of the ester compound obtained in 1.(3) of Example 1 and 1.5 mmol (260 mg) of m-chloroperbenzoic acid dissolved in 10 ml of methylene chloride was stirred for 5 hours at room temperature, and was then allowed to stand overnight. After the resulting reaction solution had been washed with an aqueous potassium carbonate solution and water successively, the reaction solution was dried and concentrated, to obtain 440 mg of an epoxide monomer A represented by the following formula. (Yield: 86%, twisting direction of helix: L configuration)

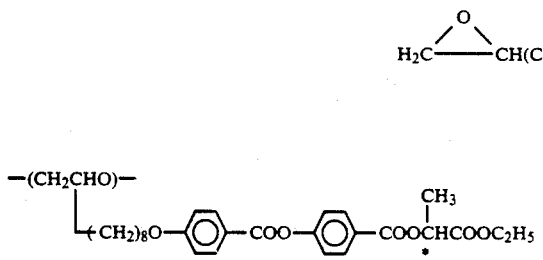

10.(2) Synthesis of polymer

After the atmosphere of reaction apparatus had been replaced with argon, 0.05 mmol (14 mg) of stannic chloride was added into a solution of 0.86 mmol of the epoxide monomer A obtained in 10.(1) dissolved in 10 ml of methylene chloride, and the mixture was then stirred for 5 days at room temperature. After concentration of the reaction solution, the concentrate was purified by column chromatography, to obtain 340 mg of a polymer having the repeating unit represented by the above formula. (Conversion rate: 88%, Mn=2,100)

EXAMPLE 11 poly[1-ethoxycarbonylethyl
4-[4'-{4''-(9,10-epoxydecyloxy)phenyl}benzoyloxy]-benzoate

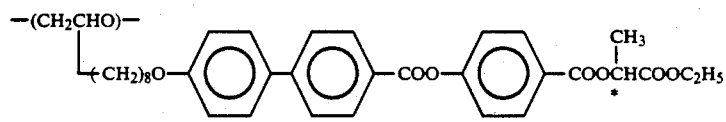

11.(1) Epoxidation

An epoxide monomer B represented by the following formula was prepared in the same manner as in 10.(1) of Example 10, with the proviso 1.0 mmol (570 mg) of the liquid-crystalline compound obtained in 2.(3) of Example 2 was used. (Yield: 94%, twisting direction of helix: L configuration)

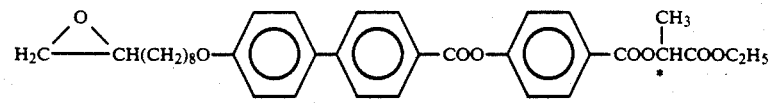

11.(2) Synthesis of polymer

A polymer having the repeating unit represented by the above formula was prepared in the same manner as in 10.(2) of Example 10, with the proviso 0.94 mmol (550 mg) of the epoxide monomer B obtained in 11.(1) was used. (Conversion rate: 92%, Mn=2,900)

EXAMPLE 12 poly[1-ethoxycarbonylethyl
4-{4'-(9,10-epoxydecyloxy)-phenyl}benzoate

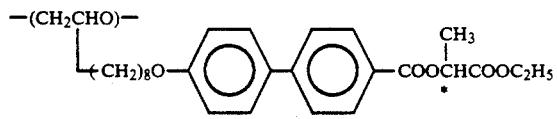

12.(1) Epoxidation

An epoxide monomer C represented by the following formula was prepared in the same manner as in 10.(1) of Example 10, with the proviso 1.0 mmol (450 mg) of the liquid-crystalline compound obtained in 3.(1) of Example 3 was used. (Yield: 94%)

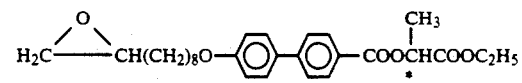

12.(2) Synthesis of polymer

A polymer having the repeating unit represented by the above formula was prepared in the same manner as in 10.(2) of Example 10, with the proviso 0.94 mmol (450 mg) of the epoxide monomer C obtained in 12.(1) was used. (Conversion rate: 81%, Mn=2,000)

EXAMPLE 13 poly[1-butoxycarbonylethyl
4-[4'-{4'''-(13,14-epoxytetradecyloxy)benzoyloxy}-phenyl]benzoate]

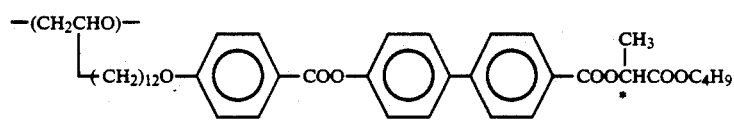

13.(1) Epoxidation

An epoxide monomer D represented by the following formula was prepared in the same manner as in 10.(1) of Example 10, with the proviso 1.0 mmol (660 mg) of the liquid-crystalline compound obtained in 4.(3) of Example 4 was used. (Yield: 90%)

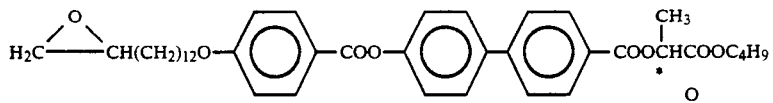

13.(2) Synthesis of polymer

A polymer having the repeating unit represented by the above formula was prepared in the same manner as in 10.(2) of Example 10, with the proviso 0.90 mmol (600 mg) of the epoxide monomer D obtained in 13.(1) was used. (Conversion rate: 84%, Mn=2,800)

EXAMPLE 14

[1-ethoxycarbonylethyl
4-{4'-(9,10-epoxydecyloxy)-benzoyloxy}benzoate]-[1-ethoxycarbonylethyl
4-[4'-{4''-(9,10-epoxydecyloxy)phenyl}benzoyloxy]-benzoate]-copolymer

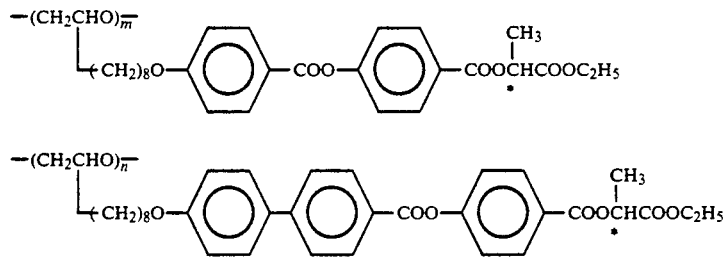

14.(1) Synthesis of polymer

A copolymer having the repeating units represented by the above formulas was prepared in the same manner as in 10.(2) of Example 10, with the proviso a mixture of 0.4 mmol (205 mg) of the epoxide monomer A obtained in 10.(1) of Example 10 and 0.6 mmol (350 mg) of the epoxide monomer B obtained in 11.(1) of Example 11 was used. (Conversion rate: 85%, Mn=2,400, copolymerization ratio m:n=40:60).

EXAMPLE 15

[(S)-1-ethoxycarbonylethyl
4-[4'-{4''-(9,10-epoxydecyloxy)phenyl}benzoyloxy]-benzoate]-[(R)-1-methylbutyl
4-{4'-(9,10-epoxydecyloxy)benzoyloxy}-benzoate]-copolymer

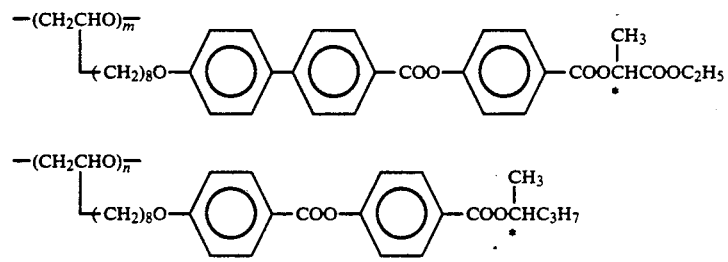

15.I Synthesis of (R)-1-methylbutyl 4-{4'-(9,10-epoxydecyloxy)benzoyloxy}benzoate (Epoxide monomer E)

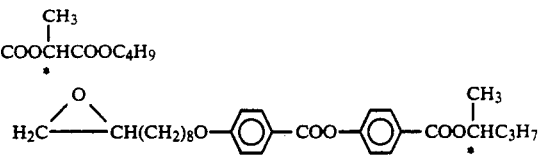

15.I.(1) Synthesis of 1-methylbutyl 4-hydroxybenzoate 25 g of thionyl chloride was added dropwise into 25 g of p-acetoxybenzoic acid. The mixture was heated to 80° C. and was then allowed to react for 3 hours. After conclusion of the reaction, the excessive thionyl chloride was distilled out under reduced pressure, to obtain an acid chloride compound. The acid chloride compound was dissolved in toluene, and the obtained toluene solution was cooled in an ice bath. Into the toluene solution being cooled in the ice bath added dropwise was a toluene solution containing 10.2 g of (R)-(−)-2-pentanol and 11 g of pyridine. The resulting mixture was then stirred overnight at room temperature. After conclusion of the reaction, the reaction solution was washed with water, dried, and concentrated under reduced pressure, and the resulting residue was dissolved in ether. 18 g of benzylamine was added dropwise into the obtained ether solution. The mixture was then stirred for one hour at room temperature. After conclusion of the reaction, the obtained product was washed with water, dried, and concentrated under reduced pressure. The resulting residue was purified by column chromatography, to obtain 20.3 g of the objective ester compound (liquid at room temperature, $[\alpha]_D = -31.4°$ (CHCl$_3$)]. (Yield: 86%)

15.I.(2) Synthesis of 1-methylbutyl 4-[4'-(9-decenyloxy)-benzoyloxy]benzoate

Toluene was added into 12.7 g of p-(9-decenyloxy)-benzoic acid, and the resulting mixture was cooled in an ice bath. Into the mixture being cooled added dropwise was 8.2 g of thionyl chloride. Reaction was then carried out for 7 hours at 80° C. After conclusion of the reaction, the reaction solution was concentrated, to obtain an acid chloride compound. On the other hand, 10.0 g of 1-methylbutyl 4-hydroxybenzoate obtained in 15.I.(1) and 3.8 g of pyridine were dissolved in toluene, and the resulting toluene solution was cooled in an ice bath. Into the toluene solution being cooled added dropwise was a toluene solution of the above-described

EXAMPLE 16

[(S)-1-ethoxycarbonylethyl 4-{4'-(9,10-epoxydecyloxy)-benzoyloxy}benzoate]-[(S)-1-ethoxycarbonylethyl 4-[4'-}4''-(9,10-epoxydecyloxy)phenyl}benzoyloxy]-benzoate]-[(S)-3-methylpentyl 4-{4'-(9,10-epoxydecyloxy)benzoyloxy}benzoate]-copolymer

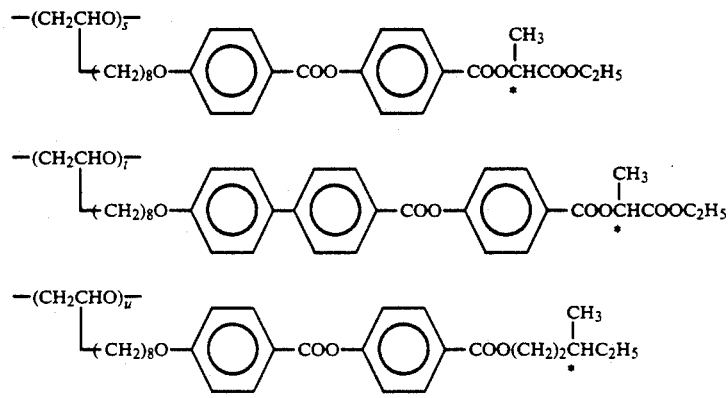

acid chloride compound. Reaction was then carried out for 5 hours at 50° C. After conclusion of the reaction, the product was washed with water and was dried over 16.I Synthesis of (S)-3-methylpentyl 4-{4'-(9,10-epoxydecyloxy)benzoyloxy}benzoate (Epoxide monomer F)

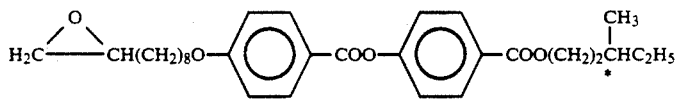

magnesium sulfate. The solvent was then distilled out from the dried product under reduced pressure. The resulting residue was purified by column chromatography, to obtain 15.1 g of the objective ester compound. (Yield: 71%)

15.I.(3) Epoxidation 15.1 g of the ester compound obtained in 15.I.(2) and m-chloroperbenzoic acid were dissolved in dichloromethane. After the atmosphere had been replaced with argon, the resulting solution was stirred for one day at room temperature. After conclusion of the reaction, the reaction solution was washed with an aqueous potassium carbonate solution, and was then washed with water. After the resulting reaction solution had been dried over magnesium sulfate, the solvent was distilled out under reduced pressure, to obtain 14.7 g of the objective epoxide monomer E represented by the above formula. (Yield: 94%, twisting direction of helix: R configuration)

15.II Synthesis of polymer

After the atmosphere of reaction apparatus had been replaced with argon, 0.05 mmol of stannic chloride was added into a solution of a mixture of 0.4 mmol (235 mg) of the epoxide monomer B obtained in 11.(1) of Example 11 and 0.6 mmol (289 mg) of the epoxide monomer E obtained in 15.I dissolved in 10 ml of methylene chloride, and the resulting mixture was then stirred for 5 days at room temperature. After concentration of the reaction solution, the concentrate was purified by column chromatography, to obtain 495 mg of the objective copolymer. (Yield: 94%, Mn=2,800, copolymerization ratio m:n=38:62)

16.I.(1) Synthesis of (S)-3-methylpentyl 4-hydroxybenzoate

A solution of 30 mmol (4.1 g) of 4-hydroxybenzoic acid, 30 mmol (3.1 g) of (S)-(+)-3-methylpentanol, and 0.2 ml of concentrated sulfuric acid dissolved in 30 ml of toluene was refluxed for 20 hours with stirring, and the resulting reaction solution was concentrated under reduced pressure, to obtain 6.5 g of the objective ester compound. [Yield: 98%, [α]$_D$= +7.8° (CHCl$_3$)]

16.I.(2) Synthesis of (S)-3-methylpentyl 4-{4'-(9-decenyloxy)benzoyloxy}benzoate A solution of 30 mmol (8.3 g) of 4-(9-decenyloxy)benzoic acid and 60 mmol of thionyl chloride dissolved in 50 ml of toluene was refluxed for 2 hours with stirring, and the reaction solution was then concentrated under reduced pressure, to obtain an acid chloride compound. Subsequently, a solution of the acid chloride compound dissolved in 10 ml of THF was added dropwise into a solution of 25 mmol (5.6 g) of the ester compound obtained in 16.I.(1) and 5 ml of triethylamine dissolved in 50 ml of THF, and the resulting mixture was stirred for 10 hours at room temperature. After concentration of the reaction solution, the concentrate was purified by column chromatography, to obtain 10.3 g of the objective ester compound. [Yield: 86%, [α]$_D$= +4.4° (CHCl$_3$)]

16.I.(3) Epoxidation

After the atmosphere of reaction apparatus had been replaced with argon, a methylene chloride solution containing 1 mmol (500 mg) of the ester compound obtained in 16.I.(2) and 1.5 mmol of m-chloroperbenzoic acid was stirred for 5 hours at room temperature, and was then allowed to stand overnight. After the reaction solution was washed with an aqueous potassium carbonate solution and water successively, the resulting reaction solution was dried and concentrated, to obtain 440 mg of the objective epoxide monomer F. (Yield: 88%, twisting direction of helix: L configuration)

16.II Synthesis of polymer 450 mg of the objective copolymer was prepared in the same manner as in 15.II of Example 15, with the proviso a mixture of 0.3 mmol (134 mg) of the epoxide monomer A obtained in 10.(1) of Example 10, 0.4 mmol (235 mg) of the epoxide monomer B obtained in 11.(1) of Example 11, and 0.3 mmol (149 mg) of the epoxide monomer F obtained in 16.I.(3) was used. (Yield: 87%, Mn=2,600, copolymerization ratio s:t:u=28:48:24)

EXAMPLE 17

[(S)-1-ethoxycarbonylethyl 4-{4'-(9,10-epoxydecyloxy)-benzoyloxy}benzoate]-[(S)-3-methylpentyl 4-{4'-(9,10-epoxydecyloxy)benzoyloxy}benzoate]-[4'-hexyloxyphenyl 4-(9,10-epoxydecyloxy)benzoate]-copolymer

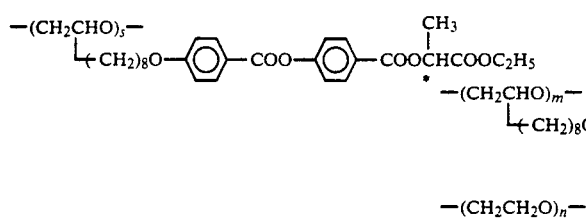

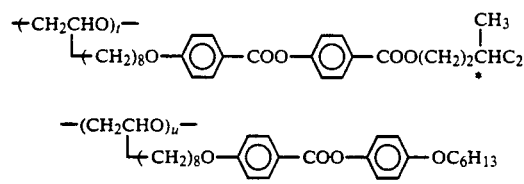

17.I Synthesis of 4'-hexyloxyphenyl 4-(9,10-epoxydecyloxy)benzoate (Epoxide monomer G)

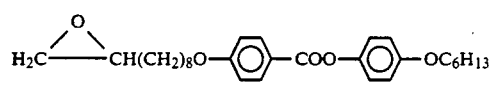

17.I.(1) Synthesis of 4'-hexyloxyphenyl 4-(9-decenyloxy)benzoate 10.9 g of the objective ester compound was prepared in the same manner as in 16.I.(1) and 16.I.(2) of Example 16, with the proviso 30 mmol (8.3 g) of 4-(9-decenyloxy)benzoic acid and 25 mmol (4.9 g) of 4-hexyloxyphenol were used. (Yield: 86%)

17.I.(2) Epoxidation 480 mg of an epoxide monomer G was prepared in the same manner as in 16.II of Example 16, with the proviso 1 mmol (479 mg) of the ester compound obtained in 17.I.(1) was used. (Yield: quantitative yield)

17.II Synthesis of polymer 380 mg of the objective copolymer was prepared in the same manner as in 15.II of Example 15, with the proviso a mixture of 0.3 mmol (153 mg) of the epoxide monomer A obtained in 10.(1) of Example 10, 0.4 mmol (200 mg) of the epoxide monomer F obtained in 16.I.(3) of Example 16, and 0.3 mmol (140 mg) of the epoxide monomer G obtained in 17.I was used. (Yield: 77%, Mn=2,600, copolymerization ratio s:t:u=33:45:22)

EXAMPLE 18

[(S)-1-ethoxycarbonylethyl 4-[4'-{4''-(9,10-epoxydecyloxy)phenyl}benzoyloxy]-benzoate]-[ethylene oxide]-copolymer

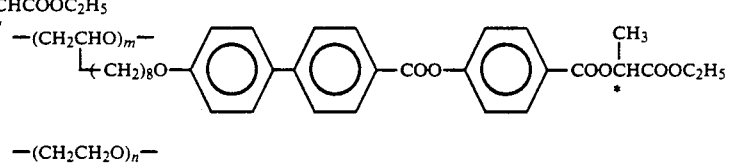

18.I Synthesis of polymer 370 mg of the objective copolymer was prepared in the same manner as in 15.II of Example 15, with the proviso 0.8 mmol (470 mg) of the epoxide monomer B obtained in 11.(1) of Example 11 and 0.2 mmol (9 mg) of ethylene oxide were used. (Yield: 77%, Mn=3,000, copolymerization ratio m:n=80:20)

EXAMPLE 19

[(S)-1-ethoxycarbonylethyl 4-[4'-{4''-(9,10-epoxydecyloxy)phenyl}benzoyloxy]-benzoate]-[(S)-1-methylbutyl 4-{4'-(9,10-epoxydecyloxy)benzoyloxy}-benzoate]-[propylene oxide]-copolymer

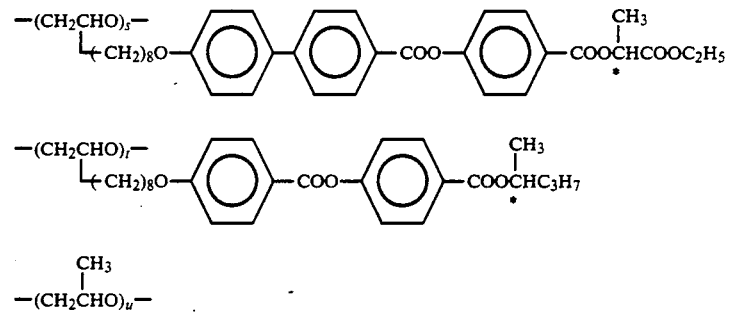

19.I Synthesis of polymer 400 mg of the objective copolymer was prepared in the same manner as in 15.II of Example 15, with the proviso 0.5 mmol (294 mg) of the epoxide monomer B obtained in 11.(1) of Example 11, 0.4 mmol (193 mg) of the epoxide monomer E obtained in 15.I of Example 15, and 0.1 mmol (6 mg) of propylene oxide were used. (Yield: 81%, Mn=2,900, copolymerization ratio s:t:u=53:37:10)

EXAMPLE 20 poly[1-ethoxycarbonylethyl 4-[4'-{4''-(10-glycidyldecyloxy)phenyl}benzoyloxy]-benzoate

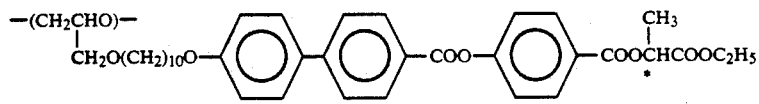

20.(1) Epoxidation

After the atmosphere of reaction apparatus had been replaced with argon, a solution of 1.0 mmol (630 mg) of the liquid-crystalline compound obtained in 5.(5) of Example 5 and 1.5 mmol (260 mg) of m-chloroperbenzoic acid dissolved in 10 ml of methylene chloride was stirred for 5 hours at room temperature, and was then allowed to stand overnight. After the reaction solution was washed with an aqueous potassium carbonate solution and water successively, the resulting reaction solution was dried and concentrated, to obtain 610 mg of an epoxide monomer H represented by the following formula. (Yield: 94%, twisting direction of helix: L configuration)

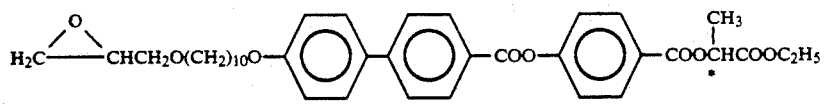

20.(2) Synthesis of polymer

After the atmosphere of reaction apparatus was replaced with argon, 0.05 mmol (14 mg) of stannic chloride was added into a solution of 0.94 mmol of the epoxide monomer H obtained in 20.(1) dissolved in 10 ml of methylene chloride, and the mixture was then stirred for 5 days at room temperature. After concentration of the reaction solution, the concentrate was purified by column chromatography, to obtain 320 mg of a polymer having the repeating unit represented by the above formula. (Conversion rate: 52%, Mn=3,200)

EXAMPLE 21 poly[1-ethoxycarbonylethyl 4-{4'-(10-glycidyldecyloxy)benzoyloxy}benzoate

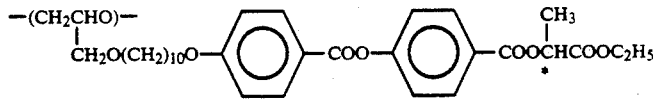

21.(1) Epoxidation

An epoxide monomer I represented by the following formula was prepared in the same manner as in 20.(1) of Example 20, with the proviso 1.0 mmol (550 mg) of the liquid-crystalline compound obtained in 6.(1) of Example 6 was used. (Yield: 94%, twisting direction of helix: L configuration)

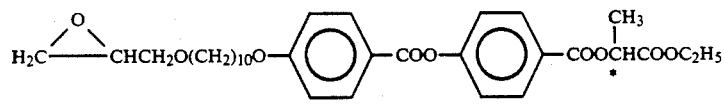

21.(2) Synthesis of polymer

A polymer having the repeating unit represented by the above formula was prepared in the same manner as in 20.(2) of Example 20, with the proviso 0.94 mmol (540 mg) of the epoxide monomer I obtained in 21.(1) was used. (Conversion rate: 85%, Mn=2,700)

EXAMPLE 22 poly[1-ethoxycarbonylethyl 4'-[4''-{8-(3,4-epoxybutyloxyoctyloxy)benzoyloxy]-biphenyl-4-carboxylate]

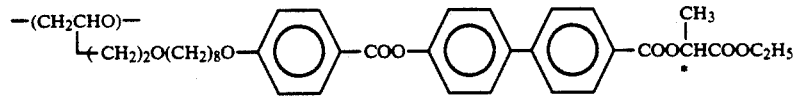

22.(1) Epoxidation

An epoxide monomer J represented by the following formula was prepared in the same manner as in 20.(1) of Example 20, with the proviso 1.0 mmol (620 mg) of the liquid-crystalline compound obtained in 7.(4) of Example 7 was used. (Yield: 94%, twisting direction of helix: L configuration)

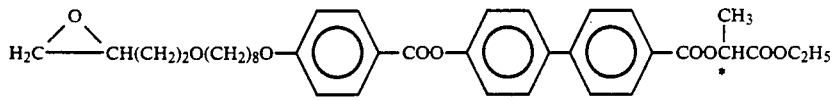

22.(2) Synthesis of polymer

A polymer having the repeating unit represented by the above formula was prepared in the same manner as in 20.(2) of Example 20, with the proviso 0.94 mmol (590 mg) of the epoxide monomer J obtained in 22.(1) was used. (Conversion rate: 75%, Mn=5,600)

EXAMPLE 23 poly[1-ethoxycarbonylethyl 4'-{8-(5,6-epoxyhexyloxy)octyloxy}benzoyloxy]biphenyl-4-carboxylate]

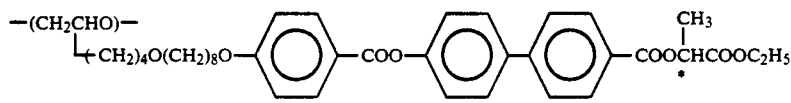

23.(1) Epoxidation

A epoxide monomer K represented by the following formula was prepared in the same manner as in 20.(1) of Example 20, with the proviso 1.0 mmol (640 mg) of the liquid-crystalline compound obtained in 8.(3) of Example (8) was used. (Yield: 93%)

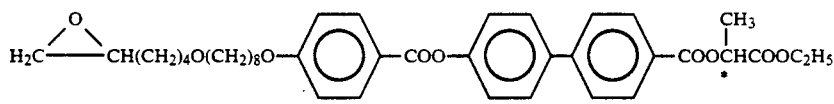

23.(2) Synthesis of polymer

A polymer having the repeating unit represented by the above formula was prepared in the same manner as in 20.(2) of Example 20, with the proviso 0.93 mmol (610 mg) of the epoxide monomer K obtained in 23.(1) was used. (Conversion rate: 86%, Mn=5,400)

EXAMPLE 24 poly[1-butoxycarbonylethyl 4-{4'-(8-glycidyloctyloxy)-phenyl}benzoate]

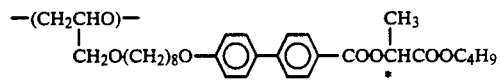

24.(1) Epoxidation

An epoxide monomer L represented by the following formula was prepared in the same manner as in 20.(1) of Example 20, with the proviso 1.0 mmol (510 mg) of the liquid-crystalline compound obtained in 9.(3) of Example 9 was used. (Yield: 97%)

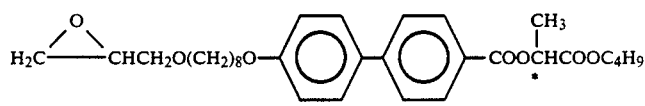

24.(2) Synthesis of polymer

A polymer having the repeating unit represented by the above formula was prepared in the same manner as in 20.(2) of Example 20, with the proviso 0.97 mmol (510 mg) of the epoxide monomer L obtained in 24.(1) was used. (Conversion rate: 77%, Mn=2,900)

EXAMPLE 25

[1-ethoxycarbonylethyl 4-[4'-{4''-(10-glycidyldecyloxy)-phenyl}benzoyloxy]-benzoate]-[1-ethoxycarbonylethyl 4-{4'-(10-glycidyldecyloxy)benzoyloxy}benzoate]-copolymer

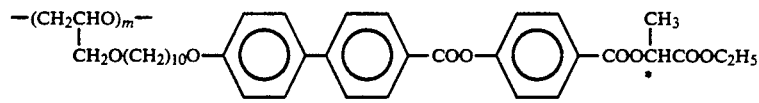

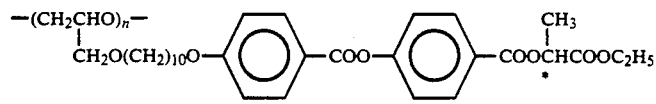

25.(1) Synthesis of polymer

A copolymer having the repeating units represented by the above formulas was prepared in the same manner as in 20.(2) of Example 20, with the proviso a mixture of 0.4 mmol (260 mg) of the epoxide monomer H obtained in 20.(1) of Example 20 and 0.6 mmol (340 mg) of the epoxide monomer I obtained in 21.(1) of Example 21 was used. (Conversion rate: 81%, Mn=3,800, copolymerization ratio m:n=38:62)

EXAMPLE 26

[1-ethoxycarbonylethyl 4-[4'-{4''-(10-glycidyldecyloxy)-phenyl}benzoyloxy]-benzoate]-[(R)-1-methylbutyl 4-{4''-(9,10-epoxydecyloxy)benzoyloxy}benzoate]-copolymer

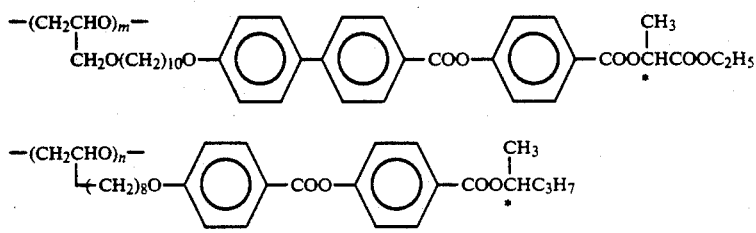

26.(1) Synthesis of polymer

A copolymer having the repeating units represented by the above formulas was prepared in the same manner as in 20.(2) of Example 20, with the proviso a mixture of 0.3 mmol (190 mg) of the epoxide monomer H obtained in 20.(1) of Example 20 and 0.7 mmol (340 mg) of the epoxide monomer E obtained in 15.I in Example 15 was used. (Conversion rate: 80%, Mn=3,600, copolymerization ratio m:n=36:64)

EXAMPLE 27

[1-ethoxycarbonylethyl 4-[4'-{4''-(10-glycidyldecyloxy)-phenyl}benzoyloxy]-benzoate]-[propylene oxide]-copolymer

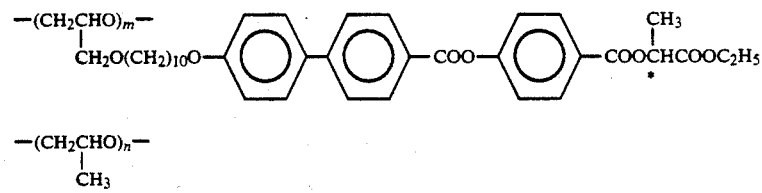

27.(1) Synthesis of polymer

A copolymer having the repeating units represented by the above formulas was prepared in the same manner as in 20.(2) of Example 20, with the proviso a mixture of 0.6 mmol (380 mg) of the epoxide monomer H obtained in 20.(1) of Example 20 and 0.4 mmol (23 mg) of propylene oxide was used. (Conversion rate: 83%, Mn=4,200, copolymerization ratio m:n=47:53)

COMPARATIVE EXAMPLE 1

A polymer having the repeating unit represented by the following formula was prepared in the same manner as in 20.(2) of Example 20, with the proviso the epoxide monomer E obtained in 15.I of Example 15 was used. (Mn=2,900)

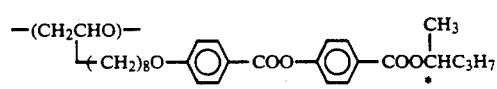

COMPARATIVE EXAMPLE 2

A polymer having the repeating unit represented by the following formula was prepared in the same manner as in 20.(2) of Example 20, with the proviso the epoxide monomer F obtained in 16.I of Example 16 was used. (Mn=2,300)

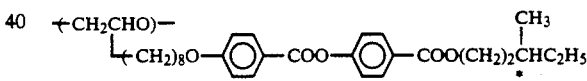

TABLE 2

| Example No. | Structure | Phase transition behavior (°C.) | Response time (ms) [measuring temperature(°C.)] |
|---|---|---|---|
| 1 | CH₂=CH(CH₂)₈O—⟨○⟩—COO—⟨○⟩—COO—⟨○⟩—COOCHCOOC₂H₅ (CH₃, *) | Cry ⇌(−36/−36) SmC* ⇌(6/−3) SmA ⇌(26/25) N* ⇌(29/27) Iso | 5 [−5] |
| 2 | CH₂=CH(CH₂)₈O—⟨○⟩—⟨○⟩—COO—⟨○⟩—COOCHCOOC₂H₅ (CH₃, *) | Cry ⇌(30/10) SmC* ⇌(117/116) SmA ⇌(147/146) Iso | 0.05 [100] |
| 3 | CH₂=CH(CH₂)₈O—⟨○⟩—⟨○⟩—⟨○⟩—COOCHCOOC₂H₅ (CH₃, *) | Cry ⇌(48/29) Iso ⇌(39/27/25) SmA | — |
| 4 | CH₂=CH(CH₂)₁₂O—⟨○⟩—⟨○⟩—COO—⟨○⟩—COOCHCOOC₄H₉ (CH₃, *) | Cry ⇌(25/19) SmC* ⇌(105/101) SmA ⇌(139/136) Iso | 0.04 [90] |
| 5 | CH₂=CHCH₂O(CH₂)₁₀O—⟨○⟩—⟨○⟩—COO—⟨○⟩—COOCHCOOC₂H₅ (CH₃, *) | Cry ⇌(23/20) SmC* ⇌(90/90) SmA ⇌(127/125) Iso | 0.05 [70] |
| 6 | CH₂=CHCH₂O(CH₂)₁₀O—⟨○⟩—⟨○⟩—COOCHCOOC₂H₅ (CH₃, *) | Cry ⇌(−17/−20) SmA ⇌(24/20) Iso | — |
| 7 | CH₂=CH(CH₂)₂O(CH₂)₈O—⟨○⟩—⟨○⟩—COO—⟨○⟩—COOCHCOOC₂H₅ (CH₃, *) | Cry ⇌(30/21) SmC* ⇌(83/76) SmA ⇌(118/118) Iso | 0.09 [70] |
| 8 | CH₂=CH(CH₂)₄O(CH₂)₈O—⟨○⟩—⟨○⟩—COO—⟨○⟩—COOCHCOOC₂H₅ (CH₃, *) | Cry ⇌(28/20) SmC* ⇌(60/58) SmA ⇌(177/106) N* ⇌(111/109) Iso | 0.45 [50] |
| 9 | CH₂=CHCH₂O(CH₂)₈O—⟨○⟩—⟨○⟩—COOCHCOOC₄H₉ (CH₃, *) | Cry ⇌(10/5) SmA ⇌(20/20) Iso | — |

TABLE 3

| Example No. | Repeating unit | Phase transition behavior (°C.) | Helical pitch (μm) | Response time (ms) [measuring temperature (°C.)] |
|---|---|---|---|---|
| 10 | +CH$_2$CHO+ / +CH$_2$)$_8$O- [structure with CH$_3$, COOCHCOOC$_2$H$_5$] | g $\xleftrightarrow{8/-10}$ SmC* $\xleftrightarrow{21/19}$ SmA $\xleftrightarrow{29/23}$ Iso | 1.0 | 30 [15] |
| 11 | +CH$_2$CHO+ / +CH$_2$)$_8$O- [structure with CH$_3$, COOCHCOOC$_2$H$_5$] | g $\xleftrightarrow{15/12}$ SmC* $\xleftrightarrow{133/130}$ SmA $\xleftrightarrow{160/156}$ Iso | 1.1 | 1000 [25] / 40 [50] / 0.2 [120] |
| 12 | +CH$_2$CHO+ / +CH$_2$)$_8$O- [structure with CH$_3$, COOCHCOOC$_2$H$_5$] | g $\xleftrightarrow{3/0}$ SmC* $\xleftrightarrow{32/30}$ SmA $\xleftrightarrow{58/54}$ Iso | 0.8 | 30 [25] |
| 13 | +CH$_2$CHO+ / +CH$_2$)$_{12}$O- [structure with CH$_3$, COOCHCOOC$_4$H$_9$] | g $\xleftrightarrow{11/5}$ SmC* $\xleftrightarrow{117/115}$ SmA $\xleftrightarrow{144/140}$ Iso | 1.0 | 40 [40] / 0.3 [100] |
| 14 | +CH$_2$CHO+$_m$ / +CH$_2$)$_8$O-$_n$ m:n = 40:60 [structure with CH$_3$, COOCHCOOC$_2$H$_5$] | g $\xleftrightarrow{-6/-10}$ SmC* $\xleftrightarrow{77/76}$ SmA $\xleftrightarrow{119/112}$ Iso | 1.0 | 50 [25] / 0.5 [60] |
| 15 | +CH$_2$CHO+$_m$ / +CH$_2$)$_8$O-$_n$ m:n = 38:62 [structure with CH$_3$, COOCHCOOC$_2$H$_5$] | g $\xleftrightarrow{-16/-20}$ SmC* $\xleftrightarrow{64/61}$ SmA $\xleftrightarrow{95/92}$ Iso | 5.4 | 20 [51] |
| 16 | +CH$_2$CHO+$_s$ / +CH$_2$)$_8$O-$_t$ s:t:u = 28:48:24 [structure with CH$_3$, COOCHCOOC$_2$H$_5$, COOCHCH$_3$C$_3$H$_7$] | g $\xleftrightarrow{10/-13}$ SmC* $\xleftrightarrow{106/104}$ SmA $\xleftrightarrow{144/104}$ Iso | 1.7 | 80 [25] |

TABLE 3-continued

| | Repeating unit | Phase transition behavior (°C.) | Helical pitch (μm) | Response time (ms) [measuring temperature (°C.)] |
|---|---|---|---|---|
| 17 | -(CH₂CHO)₇-<br>  \|<br>  (CH₂)₈O-⬡-⬡-COO-⬡-COOCHCOOC₂H₅<br>                                              \|<br>                                              CH₃ * | g ⇌ -10/-15 ⇌ SmC* ⇌ 50/47 ⇌ SmA ⇌ 68/67 ⇌ Iso | 3.1 | 20 [25] |
| 18 | s:t:u = 33:45:22<br>-(CH₂CHO)₅- -(CH₂CHO)₇- -(CH₂CHO)ᵤ-<br>  \|                 \|                 \|<br>  (CH₂)₈O-⬡-COO-⬡-⬡-COO(CH₂)₂CHC₂H₅   (similarly)   OC₆H₁₃<br>                                               \|<br>                                               CH₃ *<br><br>m:n = 80:20<br>-(CH₂CHO)ₘ-<br>  \|<br>  (CH₂)₈O-⬡-⬡-COO-⬡-COOCHCOOC₂H₅<br>                                              \|<br>                                              CH₃ *<br>-(CH₂CH₂O)ₙ- | g ⇌ -11/-15 ⇌ SmC* ⇌ 85/82 ⇌ SmA ⇌ 105/101 ⇌ Iso | 1.4 | 60 [25] |
| 19 | s:t:u = 53:37:10<br>-(CH₂CHO)₅- -(CH₂CHO)₇- -(CH₂CHO)ᵤ-<br>  \|                 \|                 \|<br>  (CH₂)₈O-⬡-⬡-COO-⬡-COOCHCOOC₂H₅   similar with COOCHC₃H₇   CH₃<br>                                              \|                                  \|<br>                                              CH₃ *                              -(CH₂CHO)ᵤ- | g ⇌ -14/-17 ⇌ SmC* ⇌ 71/69 ⇌ SmA ⇌ 99/95 ⇌ Iso | >10 | 30 [25] |
| 20 | -(CH₂CHO)-<br>  \|<br>  CH₂O(CH₂)₁₀O-⬡-⬡-COO-⬡-COOCHCOOC₂H₅<br>                                                  \|<br>                                                  CH₃ * | g ⇌ 25/25 ⇌ SmC* ⇌ 127/124 ⇌ SmA ⇌ 160/158 ⇌ Iso | 1.1 | 20 [50]<br>0.2 [120] |

TABLE 3-continued

| | Repeating unit | Phase transition behavior (°C.) | Helical pitch (μm) | Response time (ms) [measuring temperature (°C.)] |
|---|---|---|---|---|
| 21 | ‡CH₂CHO)̄<br>　　│<br>　　CH₂O(CH₂)₁₀O—⟨Ph⟩—COO—⟨Ph⟩—COO—CHCH₃—COOCHCH₃—COOC₂H₅ * | g ⇌(-24/-24) SmC* ⇌(34/30) SmA ⇌(41/39) Iso | 1.0 | 30 [25] |
| 22 | ‡CH₂CHO)̄<br>　　│<br>　　(CH₂)₂O(CH₂)₈O—⟨Ph⟩—COO—⟨Ph⟩—⟨Ph⟩—COOCHCH₃—COOC₂H₅ * | g ⇌(25/25) SmC* ⇌(137/134) SmA ⇌(170/168) Iso | 1.0 | 33 [50]<br>0.3 [120] |
| 23 | ‡CH₂CHO)̄<br>　　│<br>　　(CH₂)₄O(CH₂)₈O—⟨Ph⟩—COO—⟨Ph⟩—⟨Ph⟩—COOCHCH₃—COOC₂H₅ * | g ⇌(20/20) SmC* ⇌(90/89) SmA ⇌(141/140) Iso | 1.1 | 25 [50]<br>0.4 [80] |
| 24 | ‡CH₂CHO)̄<br>　　│<br>　　CH₂O(CH₂)₈O—⟨Ph⟩—⟨Ph⟩—COOCHCH₃—COOC₄H₉ * | g ⇌(-10/-15) SmC* ⇌(5/33) SmA ⇌(55/53) Iso | 0.8 | 20 [30]<br>0.2 [120] |
| 25 | ‡CH₂CHO)̄ₘ  m:n = 38:62<br>　　│<br>　　CH₂O(CH₂)₁₀O—⟨Ph⟩—COO—⟨Ph⟩—⟨Ph⟩—COOCHCH₃—COOC₂H₅ * | g ⇌(-5/-10) SmC* ⇌(79/75) SmA ⇌(110/104) Iso | 1.2 | 15 [30]<br>0.5 [70] |
| 26 | ‡CH₂CHO)̄ₙ  m:n = 36:64<br>　　│<br>　　CH₂O(CH₂)₁₀O—⟨Ph⟩—COO—⟨Ph⟩—⟨Ph⟩—COOCHCH₃—COOC₂H₅ * | g ⇌(-20/-25) SmC* ⇌(63/58) SmA ⇌(90/88) Iso | 5.2 | 15 [30]<br>0.5 [70] |
| 27 | ‡CH₂CHO)̄ₘ  m:n = 47:53<br>　　│<br>　　CH₂O(CH₂)₈O—⟨Ph⟩—COO—⟨Ph⟩—COOCHC₃H₇ *<br>‡CH₂CHO)̄ₙ<br>　　│<br>　　CH₂O(CH₂)₁₀O—⟨Ph⟩—COO—⟨Ph⟩—⟨Ph⟩—COOCHCH₃—COOC₂H₅ * | g ⇌(0/0) SmC* ⇌(110/100) SmA ⇌(137/129) Iso | 1.8 | 35 [30]<br>0.2 [90] |

TABLE 3-continued

| Comparative Example No. | Repeating unit | Phase transition behavior (°C.) | Helical pitch (μm) | Response time (ms) [measuring temperature (°C.)] |
|---|---|---|---|---|
| 1 | ‑(CH$_2$CHO)$_n$‑<br>  \|<br>  (CH$_2$)$_8$O—⟨○⟩—COO—⟨○⟩—COOCHC$_3$H$_7$<br>                                           \|<br>                                          CH$_3$ * | g $\underset{-22}{\overset{-20}{\leftrightarrows}}$ SmC* $\underset{17}{\overset{21}{\leftrightarrows}}$ Iso | 1.1 | 1.0 [15] |
| 2 | ‑(CH$_2$CHO)$_n$‑<br>  \|<br>  (CH$_2$)$_8$O—⟨○⟩—COO—⟨○⟩—COO(CH$_2$)$_2$CHC$_2$H$_5$<br>                                                \|<br>                                               CH$_3$ * | g $\underset{-34}{\overset{-29}{\leftrightarrows}}$ SmC* $\underset{33}{\overset{36}{\leftrightarrows}}$ SmA $\underset{48}{\overset{63}{\leftrightarrows}}$ Iso | 1.6 | 120 [30] |

What is claimed is:

1. A liquid-crystalline polymer having the repeating units represented by the following general formula (II):

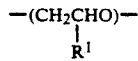 (II)

wherein
R¹ is

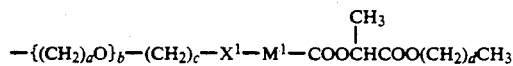

wherein
a is an integer having a value of 1 to 10,
b is an integer having a value of 0 or 1,
c is an integer having a value of 1 to 30,
X¹ is —COO, —O— or a single bond,
M¹ is

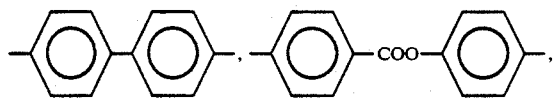

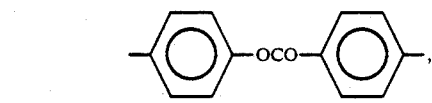

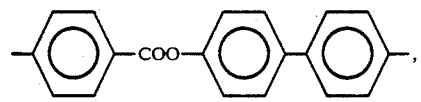

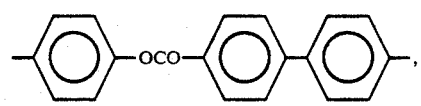

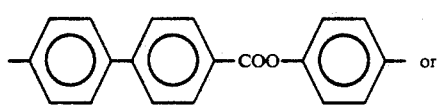 or

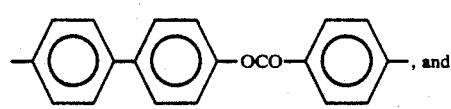, and d is an integer having a value of 1 to 5.

2. The liquid-crystalline polymer as claimed in claim 1, wherein a is an integer having a value of 1 to 5, b is an integer having a value of 1, and c is an integer having a value of 6 to 12.

3. The liquid-crystalline polymer as claimed in claim 2, wherein

X¹ is —O— and
M¹ is

,

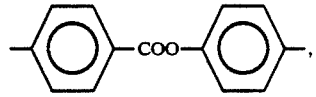,

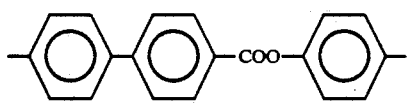, or

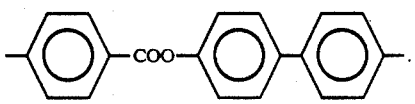.

4. The liquid-crystalline polymer as claimed in claim 3, wherein d is an integer having a value of 1 or 3.

5. A liquid-crystalline copolymer having the repeating units represented by the following general formula (II) and the repeating units represented by the following general formula (III), the molar ratio between the repeating units (II) and the repeating units (III), m:n, is from 99:1 to 1:99,

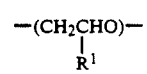 (II)

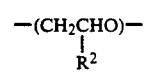 (III)

wherein
R¹ is

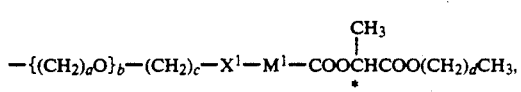

R² is

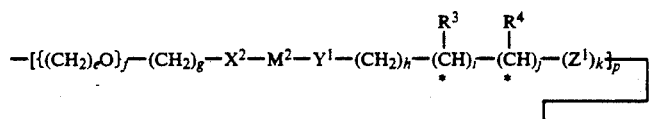

wherein
X¹ is —COO, —O— or a single bond,
X² and Y¹ are each independently —COO—, —OCO—, —O— or a single bond,
M¹ and M² are each independently

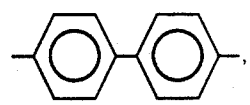,

-continued $-\langle\bigcirc\rangle-COO-\langle\bigcirc\rangle-,$ $-\langle\bigcirc\rangle-OCO-\langle\bigcirc\rangle-,$ $-\langle\bigcirc\rangle-COO-\langle\bigcirc\rangle-\langle\bigcirc\rangle-,$ $-\langle\bigcirc\rangle-OCO-\langle\bigcirc\rangle-\langle\bigcirc\rangle-,$ $-\langle\bigcirc\rangle-\langle\bigcirc\rangle-COO-\langle\bigcirc\rangle-$ or $-\langle\bigcirc\rangle-\langle\bigcirc\rangle-OCO-\langle\bigcirc\rangle-,$ $Z^1$ is —COO—, —OCO— or —O—,
$R^3$ and $R^4$ are each independently —CH$_3$, —CF$_3$, —CN or a halogen group,
a and e are each independently an integer having a value of 1 to 10,
q is an integer having a value of 0 to 10,
c and g are each independently an integer having a value of 1 to 30,
d is an integer having a value of 1 to 5,
h is an integer having a value of 0 to 5, and b, f, i, j, k, and p are each independently an integer having a value of 0 or 1,
with the proviso that $M^1 \neq M^2$ when a=e and b=f and k=p=1 and $Z^1$=—COO—.

6. A liquid-crystalline copolymer having the repeating units represented by the following general formula (II), the repeating units represented by the following general formula (IV), and the repeating units represented by the following general formula (V), the molar ratio between the repeating units (II), the repeating units (IV), and the repeating units (V), s:t:u, is 98:1:1-1:98:1-1:1:98, $$-(CH_2CHO)-\atop R^1 \qquad (II)$$

$$-(CH_2CHO)-\atop R^5 \qquad (IV)$$

$$-(CH_2CHO)-\atop R^6 \qquad (V)$$

wherein $R^1$ is $$-\{(CH_2)_aO\}_b-(CH_2)_c-X^1-M^1-COOCH(CH_3)COO(CH_2)_dCH_3,$$

$R^5$ is $$-\{(CH_2)_eO\}_f-(CH_2)_g-X^2-M^2-Y^1-(CH_2)_h-(CH)_i-(CH)_j-(Z^1)_k-$$
$$\qquad\qquad\qquad\qquad\qquad\qquad R^3 \quad R^4$$
$$\qquad\qquad\qquad\qquad\qquad\qquad\qquad\qquad -(CH_2)_qH,$$

$R^6$ is $$-\{(CH_2)_rO\}_v-(CH_2)_w-X^3-M^3-Y^2-(CH_2)_x-(CH)_y-(CH_2)_AH,$$
$$\qquad\qquad\qquad\qquad\qquad\qquad\qquad R^7$$

wherein
$X^1$ is —COO, —O— or a single bond,
$X^2, X^3, Y^1$, and $Y^2$ are each independently —COO—, —OCO—, —O— or a single bond,
$M^1, M^2$, and $M^3$ are each independently $-\langle\bigcirc\rangle-\langle\bigcirc\rangle-,\quad -\langle\bigcirc\rangle-COO-\langle\bigcirc\rangle-,$ $-\langle\bigcirc\rangle-OCO-\langle\bigcirc\rangle-,$ $-\langle\bigcirc\rangle-COO-\langle\bigcirc\rangle-\langle\bigcirc\rangle-,$ $-\langle\bigcirc\rangle-OCO-\langle\bigcirc\rangle-\langle\bigcirc\rangle-,$ $-\langle\bigcirc\rangle-\langle\bigcirc\rangle-COO-\langle\bigcirc\rangle-$ or $-\langle\bigcirc\rangle-\langle\bigcirc\rangle-OCO-\langle\bigcirc\rangle-,$ and $Z^1$ is —COO—, —OCO— of —O—,
$R^3, R^4$, and $R^7$ are each independently —CH$_3$, —CF$_3$, —CN or a halogen group,
a, e, and r are each independently an integer having a value of 1 to 10,
q and A are each independently an integer having a value of 0 to 10,
c, g, and w are each independently an integer having a value of 1 to 30,
d is an integer having a value of 1 to 5, h and x are each independently are an integer having a value of 0 to 5, and b, f, v, i, j, k, y, and z are each independently an integer having a value of 0 or 1, with the proviso that $M^1 \neq M^2$ when $a=e$ and $b=f$ and $k=1$ and $Z^1=$—COO—, and that $(h+q) \neq (x+A)$ when $e=r$ and $f=v$ and $k=0$ and $z=1$.

7. The liquid-crystalline polymer as claimed in claim 1, wherein b is an integer having a value of 0, and c is an integer having a value of 6 to 12.

8. The liquid-crystalline polymer as claimed in claim 7, wherein $X^1$ is —O— and $M^1$ is

,

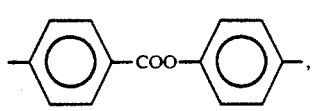,

-continued

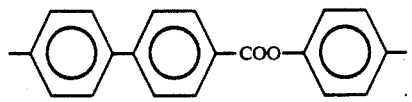

or

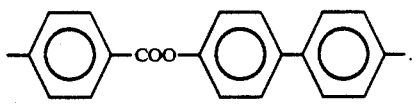

9. The liquid-crystalline polymer as claimed in claim 8, wherein c is an integer having a value of 8 to 12, and d is an integer having a value of 1 to 3.

10. The liquid-crystalline polymer as claimed in claim 9, wherein c is an integer having a value of 8, d is an integer having a vlaue of 1, and $M^1$ is

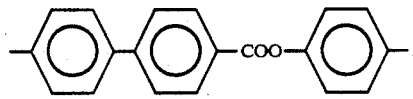.

* * * * *